US012765918B2

(12) United States Patent
Greenhalgh et al.

(10) Patent No.: US 12,765,918 B2
(45) Date of Patent: Oct. 20, 2026

(54) DECOMPRESSION SYSTEM AND METHODS OF USE

(71) Applicant: Travis Greenhalgh, Boca Raton, FL (US)

(72) Inventors: Travis Greenhalgh, Boca Raton, FL (US); Bryan Hellriegel, Boynton Beach, FL (US)

(73) Assignee: Travis Greenhalgh, Boca Raton, FL (US)

( * ) Notice: Subject to any disclaimer, the term of this patent is extended or adjusted under 35 U.S.C. 154(b) by 0 days.

(21) Appl. No.: 19/294,037

(22) Filed: Aug. 7, 2025

(65) Prior Publication Data

US 2026/0041459 A1 Feb. 12, 2026

Related U.S. Application Data

(60) Provisional application No. 63/680,457, filed on Aug. 7, 2024.

(51) Int. Cl.

| | |
|---|---|
| ***A61B 17/56*** | (2006.01) |
| ***A61B 17/00*** | (2006.01) |
| ***A61B 17/17*** | (2006.01) |
| ***A61B 90/00*** | (2016.01) |
| ***A61B 90/30*** | (2016.01) |

(52) U.S. Cl.
CPC ........ *A61B 17/56* (2013.01); *A61B 17/00234* (2013.01); *A61B 17/1757* (2013.01); *A61B 90/03* (2016.02); *A61B 90/30* (2016.02); *A61B 2017/00238* (2013.01); *A61B 2017/00367* (2013.01); *A61B 2090/034* (2016.02); *A61B 2090/036* (2016.02)

(58) Field of Classification Search
CPC ............ A61B 17/7071; A61B 17/1757; A61B 17/1604; A61B 17/1611; A61B 17/1605; A61B 17/1606; A61B 17/1607; A61B 17/1608; A61B 17/1671; A61B 17/1613
See application file for complete search history.

(56) References Cited

U.S. PATENT DOCUMENTS 5,961,522 A * 10/1999 Mehdizadeh ...... A61B 17/1604 606/84
6,929,606 B2 * 8/2005 Ritland .............. A61B 17/1757 600/210
7,799,033 B2 9/2010 Assell
7,896,879 B2 3/2011 Solsberg
8,048,080 B2 11/2011 Bleich (Continued)

FOREIGN PATENT DOCUMENTS

WO WO 2008/027923 3/2008
WO WO 2016/177271 A1 11/2016
WO WO 2022/207105 A1 10/2022

*Primary Examiner* — Matthew J Lawson
(74) *Attorney, Agent, or Firm* — Knobbe, Martens, Olson & Bear, LLP

(57) ABSTRACT

A decompression surgery system includes a cannula configured to engage a lamina, the cannula including a lumen. The system further includes a guide configured to be received by the cannula, the guide including a guide lumen that is offset from the central longitudinal axis of the guide. The guide can be rotated to multiple positions so the guide lumen can be used to access different parts of the lamina. Instruments for laminar decompression such as a drill bit can be advanced through the guide lumen.

18 Claims, 67 Drawing Sheets

(56) References Cited

U.S. PATENT DOCUMENTS

| | | | | |
|---|---|---|---|---|
| 8,221,424 | B2 | 7/2012 | Cha | |
| 8,491,585 | B2 | 7/2013 | Hannani | |
| 8,827,900 | B1 | 9/2014 | Pimenta | |
| 8,870,890 | B2 | 10/2014 | Aschmann | |
| 8,882,772 | B2 | 11/2014 | Solsberg | |
| 9,084,641 | B2 | 7/2015 | Chang | |
| 9,168,033 | B2 | 10/2015 | Hess | |
| 9,168,047 | B2 | 10/2015 | To | |
| 9,204,906 | B2 * | 12/2015 | Cannestra | A61B 17/1757 |
| 9,320,535 | B2 | 4/2016 | Zaretzka | |
| 9,414,884 | B2 | 8/2016 | Faehndrich | |
| 9,700,427 | B2 | 7/2017 | Assell | |
| 9,907,568 | B2 | 3/2018 | Ahmad | |
| 9,962,170 | B2 | 5/2018 | Jansen | |
| 10,143,486 | B2 | 12/2018 | Lauchner | |
| 10,568,641 | B1 | 2/2020 | Karasic | |
| 11,331,091 | B2 | 5/2022 | Jung | |
| 12,201,309 | B2 | 1/2025 | Greenhalgh | |
| 2002/0022704 | A1 | 2/2002 | Geibeler | |
| 2002/0022764 | A1 | 2/2002 | Smith | |
| 2005/0171549 | A1 | 8/2005 | Boehm | |
| 2005/0197661 | A1 * | 9/2005 | Carrison | A61B 17/32002 606/170 |
| 2005/0261692 | A1 * | 11/2005 | Carrison | A61B 17/1631 606/79 |
| 2006/0004369 | A1 * | 1/2006 | Patel | A61B 17/320783 606/79 |
| 2006/0235452 | A1 | 10/2006 | Schomer | |
| 2007/0093841 | A1 | 4/2007 | Hoogland | |
| 2008/0033465 | A1 | 2/2008 | Schmitz | |
| 2008/0103504 | A1 | 5/2008 | Schmitz | |
| 2009/0018507 | A1 | 1/2009 | Schmitz | |
| 2009/0276048 | A1 | 11/2009 | Chirico | |
| 2010/0286695 | A1 * | 11/2010 | Hannani | A61B 17/1671 606/86 A |
| 2011/0028978 | A1 | 2/2011 | Li | |
| 2012/0143206 | A1 | 6/2012 | Wallace | |
| 2012/0197320 | A1 | 8/2012 | Bereczki | |
| 2012/0221007 | A1 | 8/2012 | Batten | |
| 2013/0289399 | A1 * | 10/2013 | Choi | A61B 17/1608 606/86 R |
| 2014/0114315 | A1 | 4/2014 | Leguidleguid | |
| 2014/0142379 | A1 | 5/2014 | Faehndrich | |
| 2014/0275992 | A1 * | 9/2014 | Choi | A61B 17/1671 600/424 |
| 2014/0276848 | A1 | 9/2014 | Leguidleguid | |
| 2015/0265319 | A1 | 9/2015 | Ferree | |
| 2016/0095503 | A1 | 4/2016 | Davis | |
| 2017/0319244 | A1 | 11/2017 | Galino | |
| 2018/0028130 | A1 | 2/2018 | Choi | |
| 2018/0064471 | A1 | 3/2018 | Lee | |
| 2018/0271574 | A1 * | 9/2018 | Ammerman | A61B 17/7071 |
| 2019/0125329 | A1 | 5/2019 | Simonson | |
| 2019/0216486 | A1 | 7/2019 | Weitzman | |
| 2019/0254768 | A1 | 8/2019 | Lieberman | |
| 2020/0155205 | A1 * | 5/2020 | Tanaka | A61B 17/1757 |
| 2020/0229829 | A1 | 7/2020 | Ahrens | |
| 2020/0281621 | A1 | 9/2020 | Gill | |
| 2020/0330160 | A1 | 10/2020 | Dace | |
| 2021/0220146 | A1 | 7/2021 | Fabian | |
| 2021/0298843 | A1 | 9/2021 | Rezach | |
| 2021/0378689 | A1 | 12/2021 | Tyndall | |
| 2021/0386434 | A1 * | 12/2021 | Tanaka | A61B 90/39 |
| 2021/0393408 | A1 | 12/2021 | Ginn | |
| 2022/0071663 | A1 | 3/2022 | Grob | |
| 2022/0071679 | A9 | 3/2022 | Naraghi | |
| 2022/0160375 | A1 | 5/2022 | Chin | |
| 2022/0211393 | A1 | 7/2022 | Messinger | |
| 2022/0265258 | A1 | 8/2022 | Choi | |
| 2022/0265285 | A1 | 8/2022 | Weitzman | |
| 2022/0304716 | A1 | 9/2022 | Cho | |
| 2022/0346822 | A1 | 11/2022 | Tran | |
| 2023/0104335 | A1 | 4/2023 | Choi | |
| 2024/0260975 | A1 * | 8/2024 | Greenhalgh | A61B 17/1671 |
| 2024/0299045 | A1 * | 9/2024 | Neary | A61B 17/320016 |
| 2025/0366868 | A1 | 12/2025 | Greenhalgh | |

* cited by examiner

DECOMPRESSION SYSTEM AND METHODS OF USE

INCORPORATION BY REFERENCE TO ANY PRIORITY APPLICATIONS

The present application claims priority benefit of Provisional Patent Application No. 63/680,457, entitled "DECOMPRESSION SYSTEM AND METHODS OF USE," filed Aug. 7, 2024, the entire disclosure of which is hereby expressly incorporated by reference. Any and all applications for which a foreign or domestic priority claim is identified in the Application Data Sheet as filed with the present application are hereby incorporated by reference under 37 CFR 1.57.

BACKGROUND

Field of the Invention

The present application relates to spinal surgery in general, and more particularly, to methods, systems, and apparatuses for decompression.

Description of the Related Art

Spinal stenosis is the narrowing of one or more spaces within the spine and can occur in the central canal surrounding the spinal cord or the lateral recess surrounding a peripheral nerve root. Reduction of space within the spine means a reduction in space available for the spinal cord and nerves that branch from the spinal cord. A tightened space can cause the spinal cord or nerves to become irritated, compressed, or pinched, which may result in back pain, weakness, and sciatica.

Spinal stenosis usually develops slowly over time, and it is most commonly caused by osteoarthritic changes that naturally occur in the spine as it ages. Depending on the location and severity of the stenosis, patients may feel pain, numbing, tingling, and/or weakness in the neck, back, arms, legs, hands, or feet.

More specifically, lumbar stenosis is the narrowing of the spinal canal or the tunnels through which nerves and other structures communicate with the lower back. Narrowing of the spinal canal usually occurs due to changes associated with aging that decrease the size of the spinal canal, including the movement of one of the vertebrae out of alignment.

Narrowing of the spinal canal or the side canals that protect the nerves often results in a pinching of the nerve root of the spinal cord. The nerves become increasingly irritated as the diameter of the canal becomes narrower. Spinal cord compression can lead to weakness or paralysis if left untreated.

Spinal stenosis can develop in anyone, but it is most common in men and women over the age of fifty. Younger individuals may be born with a congenital narrow spinal canal which can also result in spinal stenosis. Other conditions that affect the spine, such as cancer, scoliosis, or injury to the spine can put people at risk for developing spinal stenosis.

The spine consists of 24 vertebra plus the fused bones of the sacrum and coccyx, beginning at the base of the skull and ending at the pelvis. The spine supports an individual's body weight and protects the spinal cord and nerve roots. Each vertebrae consists of a body with a central opening (the spinal canal), flat areas (facet joints) where one vertebrae comes into contact with others above and below it, and bone protrusions along the sides of the vertebrae (transverse processes). Back portions, called the laminae, surround the cord and form a covering to the spinal canal. The part of the lamina where both sides come together creates a protrusion called the spinous process. Between each vertebrae body is a flat, round, soft cushion called an intervertebral disk that serves as a shock absorber. Ligaments are the strong fiber bands that hold the vertebrae together, keeping the spine stable and protecting the disks.

The spinal cord connects to the brain stem and sends and receives messages between the body and the brain. The spinal cord runs through the center of each vertebra of the spinal canal and is completely surrounded by the bony parts of the spine. Peripheral nerves roots are the initial segment of a bundle of nerve fibers that come off the spinal cord and exit the spinal column through side spaces between the vertebrae called the neural foramen. The nerve roots innervate and control all parts of the body.

Spinal stenosis has many causes. Degeneration of the structure of the spine can cause narrowing of the space around your spinal cord and nerves roots that exit through the neuro foramen. If the spinal cord and/or nerve roots become compressed or pinched, a variety of symptoms may appear including back pain, numbness, tingling, or weakness.

Osteoarthritis or bone growth/spurs is a condition that breaks down cartilage in the joints, including the spine. Cartilage is the protective covering of joints, and as it wears away, the bones begin to rub against each other like sandpaper. The body responds by growing new bone, but bone spurs or an overgrowth of the bone commonly occurs. Bone spurs on the vertebrae may extend into the spinal canal narrowing the openings and pinching nerves in the spine.

The narrowing of the spinal canal is usually a slow process and worsens over time. Although spinal stenosis can happen anywhere along the spinal column, the lower back and neck are common areas. When stenosis becomes worse there are many treatment options that can be sought, usually starting with the most conservative. Due to the complexity of spinal stenosis and the delicate nature of the spine, surgery is often considered when all other treatment options have failed or when symptoms become intolerable.

Surgery options include removing portions of bone, bony growths, facets, or disks that are crowding the spinal canal and pinching spinal nerves.

The most common type of surgery for spinal stenosis is laminectomy depression surgery which involves removing the lamina, the portion of the vertebra that covers and protects the spinal cord. Some ligaments and bone spurs may also be removed. The procedure creates room for the spinal cord and nerves, relieving the symptoms. Currently, this procedure requires a large incision and is performed open. This procedure also destabilizes the motion segment by removing the posterior tension band ligaments and structure which can later lead to instability and a need for spinal fusion.

Laminotomy is a partial laminectomy where only a small part of the lamina is removed in the area causing the most pressure on the nerve. This procedure can be performed open or minimally invasively.

Laminoplasty is a procedure performed in the neck (cervical) area only. Part of the lamina is removed to provide more canal space, then metal plates and screws are used to create a bridge across the area where bone was removed.

A foraminotomy is a procedure that opens the foramen, the area in the vertebrae where the nerve roots exit. Then, bone or tissue in this area is removed to provide more space for the nerve roots.

SUMMARY

Current surgical procedures have inherent risks, including nerve or spinal cord damage while performing the decompression. Instruments such as kerrisons, rongeurs, and pituitarys are used to extract bone and soft tissues to create more space for the neural elements. One such injury resulting from surgery is a dural tear which can cause pain and require arduous repair and results from tearing of the membrane that surrounds the spinal cord. Although the procedures have been performed for years, there continues to be injuries and risks. Systems, apparatuses, and methods for decompression are disclosed herein that can create an optimal surgical outcome in a minimally invasive fashion with decreased risk to the patient.

Also provided herein is a decompression surgery system. The system includes an instrument shuttle configured to engage a first side of a target anatomical location and a working channel configured to couple to and advance along the instrument shuttle to the target anatomical location. The working channel includes a distal end configured to engage a second side of the target anatomical location so that the target anatomical location is positioned between a portion of the instrument shuttle and the distal end of the working channel.

The instrument shuttle can include a guard having a guard plate configured to contact the first side of the target anatomical location. The guard plate can be pivotable about a pivot point of the instrument shuttle. The instrument shuttle can include a knob configured to rotate to change an angle of the guard plate. The guard can include a guard body and a pivot arm, wherein the knob is configured to rotate to cause axial movement of the pivot arm, wherein axial movement of the pivot arm is configured to cause the guard plate to pivot about the pivot point. The instrument shuttle can include a hook configured to engage the first side of the target anatomical location. The system can further include guard having a guard plate, wherein the guard plate is configured to contact the target anatomical location to secure the target anatomical location between the guard plate and the distal end of the working channel. The instrument shuttle can include a track, wherein the working channel is configured to couple to and advance along the track to the target anatomical location. The track can include a plurality of grooves, and the working channel can include a plurality of track arms having tips configured to releasably engage the plurality of grooves of the track. The system can include a multi-channel guide configured to be received within the working channel, the multi-channel guide having a plurality of channels configured to receive one or more instruments therethrough. The target anatomical location can be a lamina.

Also provided herein is a method of performing a decompression surgery. The method includes advancing an instrument shuttle to a target anatomical location through an incision, engaging a portion of the instrument shuttle with a first side of the target anatomical location, coupling a working channel to the instrument shuttle, and advancing the working channel to the target anatomical location along the instrument shuttle so that a distal end of the working channel engages a second side of the target anatomical location so that the target anatomical location is positioned between the portion of the instrument shuttle and the distal end of the working channel.

The method can include advancing an instrument through the working channel to the target anatomical location and cutting the target anatomical location using the instrument. The instrument can include a reamer, a trephine, a burr, or a drill. The method can include, prior to advancing the instrument through the working channel, inserting a multi-channel guide within the working channel, wherein advancing the instrument to the target anatomical location includes advancing the instrument through a channel of a plurality of channels of the multi-channel guide. The method can include, prior to advancing the instrument shuttle to the target anatomical location, making the incision with a scalpel, the scalpel including a blade coupled to a scalpel guide, wherein making the incision with the scalpel includes advancing the scalpel along a guide wire positioned within a slot of the scalpel guide. The instrument shuttle can include a hook configured to engage the first side of the target anatomical location. The method can include advancing a guard having a guard plate to the target anatomical location, and engaging the target anatomical location with the guard plate so that the target anatomical location is secure between the guard plate and the distal end of the working channel. The instrument shuttle can include a guard having a guard plate. Engaging the portion of the instrument shuttle with the first side of the target anatomical location can include engaging the guard plate with the first side of the target anatomical location. Advancing the working channel to the target anatomical location along the instrument shuttle so that the distal end of the working channel engages the second side of the target anatomical location can include securing the target anatomical location between the guard plate and the distal end of the working channel. The instrument shuttle can include a track. The method can include coupling the working channel to the track, wherein advancing the working channel to the target anatomical location along the instrument shuttle comprises advancing the instrument shuttle along the track.

In some embodiments, the decompression surgery systems described herein can include: a cannula configured to engage a lamina of a patient, the cannula including a lumen; and a guide configured to be removably received within the lumen of the cannula and including a guide lumen configured to receive one or more instruments therethrough, wherein the guide lumen is offset from a central longitudinal axis of the guide; wherein the guide is configured to move relative to the cannula to multiple positions and be received within the cannula at the multiple positions so that the guide lumen of the guide aligns with a different section of the lamina at each of the multiple positions.

In some embodiments, the cannula includes a plurality of slots, wherein the guide includes at least one protrusion, wherein the at least one protrusion is configured to be received within a different one of the plurality of slots at each position of the guide. In some embodiments, the systems can include a stabilizer configured to couple to the cannula to restrict movement of the cannula, wherein the stabilizer includes a plurality of legs configured to contact a skin surface of the patient or a drape positioned over the skin surface of the patient. In some embodiments, each of the plurality of legs of the stabilizer includes one or more non-slip surface features configured to engage the patient. In some embodiments, the stabilizer includes a central body, wherein the plurality of legs are configured to rotate about the central body. In some embodiments, the plurality of legs are configured to rotate about a longitudinal axis of the cannula and to rotate about one or more axes perpendicular with the longitudinal axis of the cannula. In some embodiments, the stabilizer includes a knob that can be actuated transition the stabilizer between an unlocked state in which the plurality of legs are rotatable and locked state in which the plurality of legs are locked in position relative to the central body. In some embodiments, the stabilizer is configured to secured at multiple axial positions along the cannula to adjust a height of the plurality of legs relative to a body of the patient. In some embodiments, the guide is rotatable between four rotatable positions within the cannula. In some embodiments, the systems can include a light source configured to couple with a proximal end of the cannula. In some embodiments, the cannula includes a body and a cap, wherein the cap is adjustable with respect to the body. In some embodiments, the cannula includes a superior guard portion configured to contact a posterior surface of the lamina, an inferior guard configured to contact an anterior surface of the lamina, and a recess between the superior guard portion and inferior guard portion configured to receive an inferior edge of the lamina therein. In some embodiments, the inferior guard portion has a greater length than the superior guard portion. In some embodiments, the systems can include a laminar locator having a pair of protrusions and a recess extending between the pair of protrusions and configured to receive an inferior edge of the lamina therein. In some embodiments, the laminar locator includes one or more angled surfaces shaped to shave bone overgrowth while the laminar locator is advanced to the lamina.

In some embodiments, the methods for performing decompression surgery described herein can include: engaging a cannula with a lamina of a patient, the cannula including a lumen; positioning a guide within the lumen of the cannula in a first position, the guide including a guide lumen offset from a central longitudinal axis of the guide; advancing an instrument through the guide lumen to the lamina and removing a first portion of the lamina using the instrument; moving the guide to a second position within the cannula so that the guide lumen aligns with a second portion of the lamina; and advancing the instrument through the guide lumen to the lamina and removing the second portion of the lamina using the instrument.

In some embodiments, the methods can include: prior to engaging the cannula with the lamina of the patient, engaging a laminar locator with a cannula of the patient; advancing a dilator over the laminar locator; and advancing the cannula over the dilator. In some embodiments, the laminar locator includes one or move angled edges, wherein the method includes translating the laminar locator back and forth to shave bone overgrowth by the angled edges. In some embodiments, the methods can include coupling a stabilizer to the cannula, the stabilizer including a plurality of legs configured to contact a skin surface of the patient or a drape positioned over the skin surface of the patient. In some embodiments, the methods can include rotating the plurality of legs about a plurality of axes.

BRIEF DESCRIPTION OF THE DRAWINGS

FIGS. 281-28J show an embodiment of the cannula 2820 of FIG. 28G with a cap 2828 shown as transparent.

DETAILED DESCRIPTION

Disclosed herein are instruments and methods for use in a decompression procedure. For example, in certain embodiments, the instruments and methods described herein can be used in a laminotomy. The instruments and methods described herein may be used to minimize risk during a decompression procedure (for example, when removing the lamina or portions thereof). For example, the instruments and methods described herein may prevent nerve or spinal cord damage during a surgical procedure.

In certain embodiments, a scalpel may be used in the systems and methods described herein. During a surgical procedure, the scalpel can be used to make an incision to cut through the skin, tissue, and muscle, for example, to access a target area. The incision can be used to create a tissue path to the target area. In some embodiments, the scalpel can be used in a laminectomy procedure. For example, the scalpel can be used to create an incision to a lamina. In some embodiments, a standard scalpel may be used. In other embodiments, the scalpel can be configured to be docked with a guide pin or guidewire. For example, in some embodiments, the scalpel can include or be coupled to a guide configured to couple with a guide pin or guidewire.

Figure 1A:
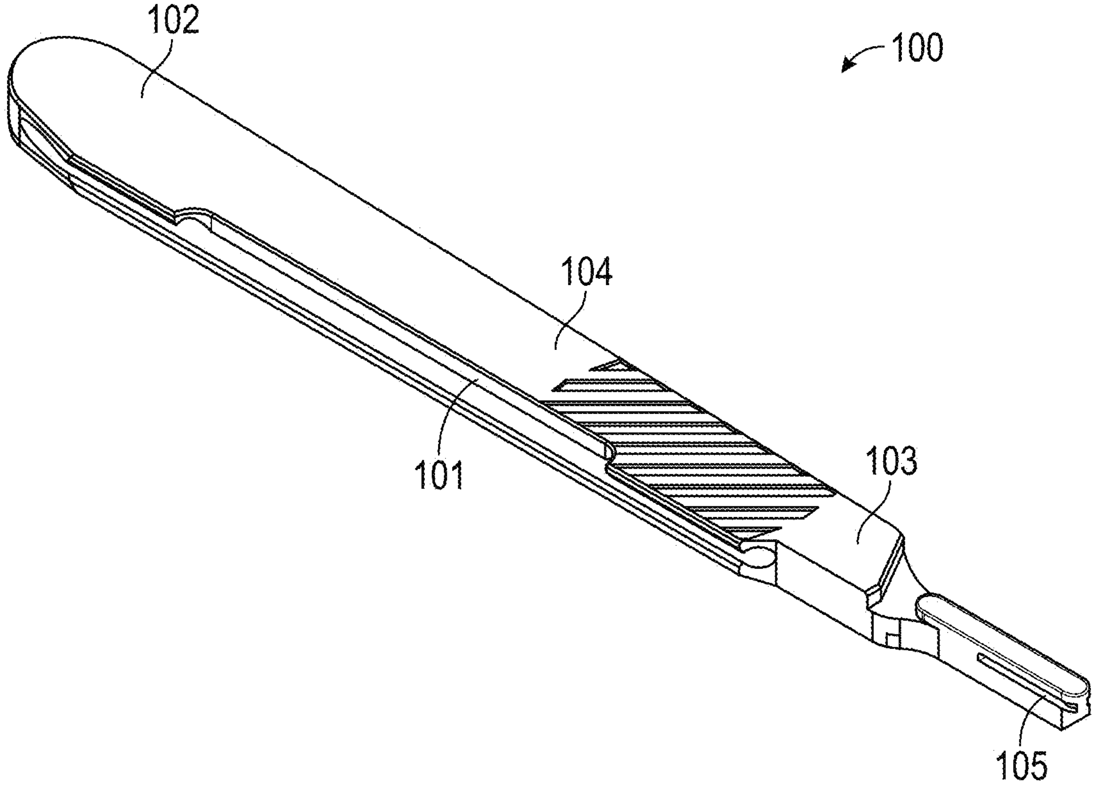
FIG. 1A depicts a perspective view of an embodiment of a scalpel guide.
Figure 1B:
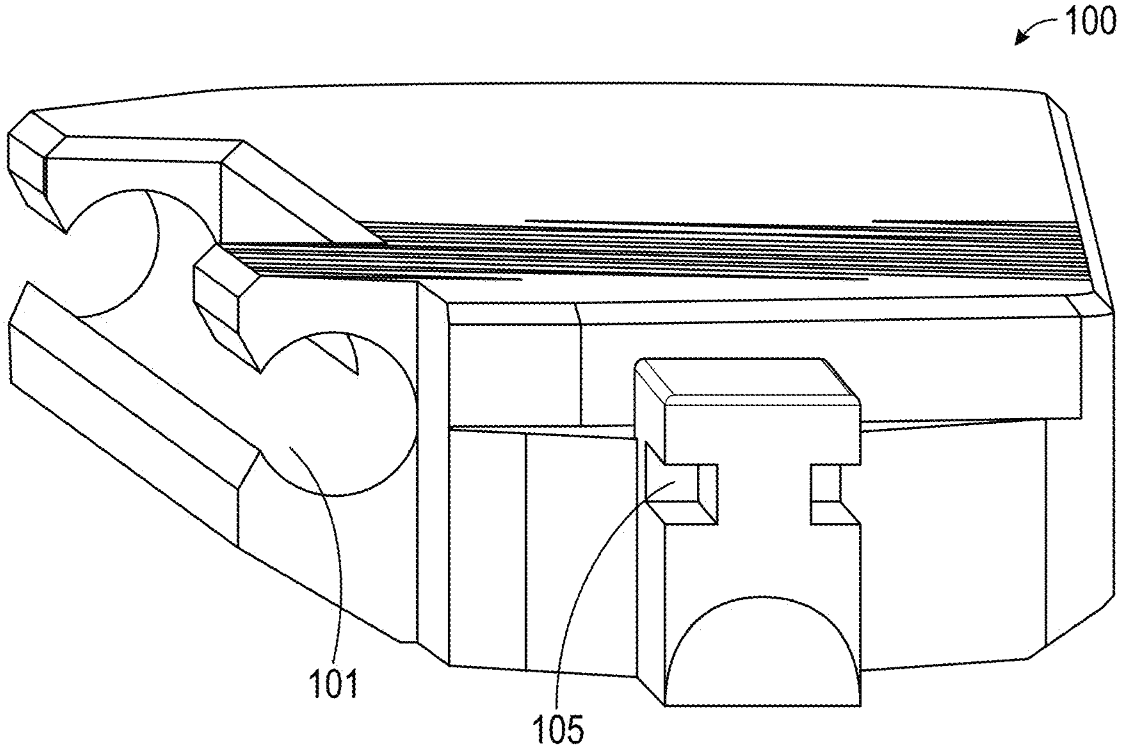
FIG. 1B depicts a front view of the scalpel guide of FIG. 1A.

FIG. 1A depicts a perspective view of a scalpel guide 100. FIG. 1B depicts a front view of the scalpel guide 100. In certain embodiments, the scalpel guide 100 may couple to a guide pin or guidewire. In certain embodiments, the scalpel guide 100 can include a channel or slot 101. The slot 101 can facilitate coupling of the guide 100 with other instruments. For example, in certain embodiments, the slot 101 can be configured to couple with a guide pin or guidewire. The scalpel guide 100 can include a handle 104. In certain embodiments, the slot 101 can extend between a proximal end 102 and a distal end 103 of the handle 104.

In certain embodiments, the scalpel guide 100 can include an attachment mechanism 105. In some embodiments, the attachment mechanism 105 can extend from the distal end 103 of the handle 104. The attachment mechanism 105 can be coupled to a blade or similar. In some embodiments, the attachment mechanism 105 can be configured to clip, strap, snap, receive, or otherwise engage a blade. For example, the attachment mechanism 105 can be a slot or recess configured to receive a blade. When a blade is coupled to the attachment mechanism 105, the guide 100 and blade can together form a scalpel.

In other embodiments, the attachment mechanism 105 can be configured to couple to (e.g., clip, strap, snap, receive or otherwise engage) a scalpel. In other embodiments, the blade can be provided with, integrally formed with, or irremovably connected to the guide 100, forming a scalpel.

Figure 2:
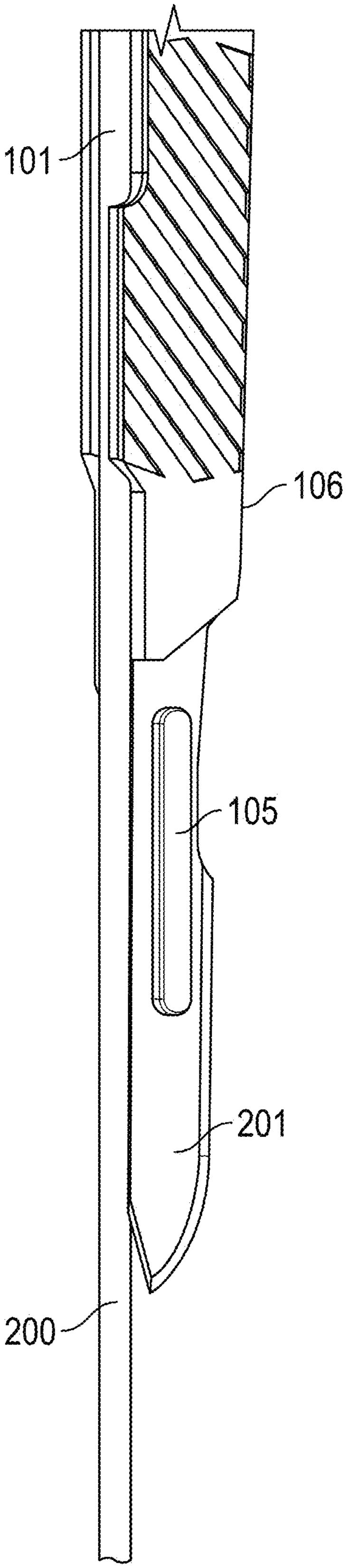
FIG. 2 depicts a side view of an embodiment of a scalpel including the scalpel guide of FIG. 1A and a blade.

As shown in FIG. 2, scalpel guide 100 and a blade 201 are coupled together to form a scalpel 106. The scalpel guide 100 can be coupled to a guidewire 200. For example, the slot 101 may be coupled to the guidewire 200. During a decompression procedure, the guide pin or guidewire 200 may be inserted into a target area, such as the lamina, spinous process, or other bony anatomy. The slot 101 can be slid down over the guidewire 200 to couple the scalpel 106 and the guidewire 200 together. In certain embodiments, the guidewire may be coupled to the scalpel 106 through clips, straps, or snaps instead of, or in addition to, the slot 101.

The scalpel 106 can be advanced along the guidewire 200 to a surgical site to create an incision to the area needing decompression. As shown in FIG. 2, the scalpel 106 may have a single blade 201. In other embodiments, the scalpel 106 may have two or more blades. For example, in some embodiments, the scalpel 106 can have two or more blades 201 coupled to the attachment mechanism 105. In other embodiments, the scalpel 106 can include a plurality of attachment mechanisms 105, each configured to couple to a unique blade 201. In some embodiments, two or more scalpels 106 can be coupled to the guidewire 200. In embodiments having two or more blades 201, the blades 201 can be spaced apart from one another to create a larger incision to the surgical location. For example, in some embodiments, two blades 201 can be positioned on opposite sides of the guidewire to create a larger incision. In some embodiments having a single blade 201, the user may advance the scalpel 106 to the target area along the guidewire 200 to create a first portion of an incision and then flip or rotate the scalpel 106 about the guidewire 200 (e.g., 180° about the guidewire) to position the blade 201 at a different position than used for the first portion of the incision. The scalpel 106 can then be advanced along the guidewire 200 to create a second portion of the incision, for example to create an incision large enough to pass dilators through the tissue and muscle to the surgical location.

Once the incision is made with scalpel 106, one or more dilators can be used to create a tissue path to the target area. For example, in certain embodiments, a first tissue dilator can be advanced over the guidewire 200 to the target area. In certain embodiments, a series of sequential dilators can follow until the site is dilated the appropriate amount for the procedure. In certain embodiments, one or more of the dilators may be used as a working channel for advancing additional instruments to the target area. In some embodiments, a separate working channel may be provided following dilation. In some embodiments, the working channels described herein can be guide tubes having lumens or channels for advancing additional instruments therethrough.

In certain embodiments of the systems and methods described herein, a positioning member or instrument shuttle may be provided. The instrument shuttle can be advanced within the incision towards the target area. Additional instruments (such as a dilator and/or working channel) may be coupled to the instrument shuttle and advanced along the instrument shuttle to the target area and/or retracted along the instrument shuttle from the target area. For example, in certain embodiments, the instrument shuttle can include a track, a rail, a gear drive, a ratchet mechanism, a linear actuator, or any other mechanism for translating an instrument along the instrument shuttle. Additional instruments (such as a dilator and/or working channel) may be coupled to the track or rail to advance the additional instruments to the target area. In some embodiments, the instrument shuttle can include engagement features, such as a hook or fastener, that can engage with and/or secure to the target area or anatomy adjacent the target area. Such engagement features may provide a stable and consistent path towards to the target area for instruments advancing along the instrument shuttle.

In certain embodiments of the systems and methods described herein, a guard may be provided. The guard may prevent damage to the surrounding anatomy (for example, the nerves and spinal cord) during a surgical procedure. The guard can protect the dura and the nerve roots when passing instruments, such as a trephine or Kerrison, to perform a decompression by removing part of the lamina, ligamentum flavum, etc., in a decompression procedure.

In certain embodiments, the guard may act as an instrument shuttle. In certain embodiments, the guard may include features, such as a track, a rail, a gear drive, a ratchet mechanism, a linear actuator, or any other suitable mechanism, for coupling to additional instruments and advancing the additional instruments to the target area. In other embodiments, a separate instrument shuttle may be provided. In certain embodiments, one or more features of the guard, such as a guard plate as described herein, can be an engagement feature or can include engagement features for engaging with or securing to the target anatomy to provide a stable and consistent path towards the target anatomy for instruments advancing along the guard.

Figure 3:
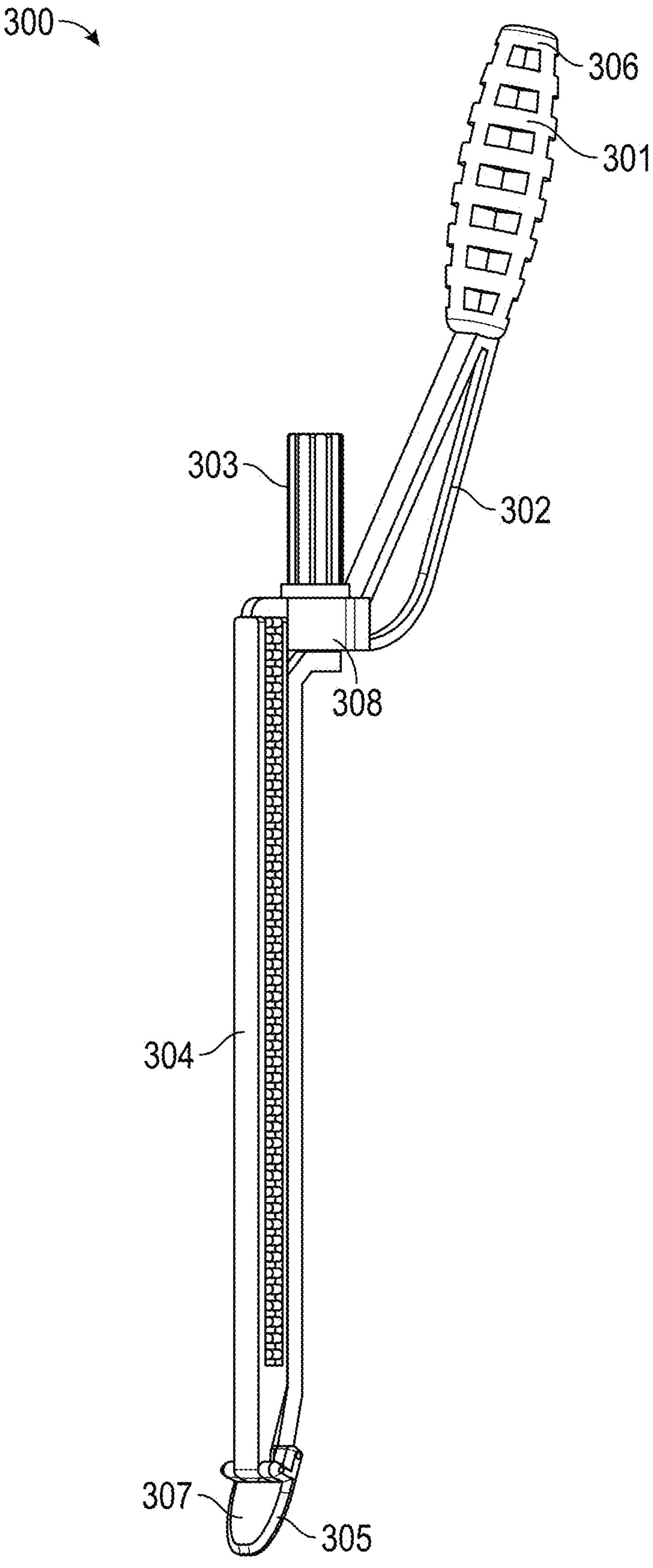
FIG. 3 depicts a perspective view of an embodiment of a guard.

Referring now to FIG. 3, a perspective view of a guard 300 is illustrated. In certain embodiments, the guard 300 can be used in a decompression procedure, such as a laminotomy. For example, in certain embodiments, after the muscle and tissue are dilated as described herein, the guard 300 may be passed through the tissue and muscle to a bony area covering the spinal canal or nerve root, such as the lamina. The guard 300 may have a proximal end 306. The proximal end 306 can include a handle 301 for manipulation by a user (e.g., a physician). The handle 301 of the guard 300 can be affixed to an arm 302. The arm 302 can be connected to a guard body 304.

In certain embodiments, the arm 302 can be pivotably coupled to the guard body 304 at a pivot point 308. that allows the arm 302 to pivot relative to the body 304. In certain embodiments, the arm 302 can be removably coupled to the guard body 304.

In certain embodiments, the guard 300 can include a guard plate 305. In certain embodiments, the guard plate 305 can be affixed at the distal end 307 of the guard 300. In certain embodiments, the guard plate 305 is pivotably coupled to the guard body 304 so that the guard plate 305 can be pivoted to different angles and/or positions.

In certain embodiments, the guard 300 can include a control mechanism for controlling the angle and/or position of the guard plate 305. For example, as shown in FIG. 3, the guard 300 can include a knob 303 that can be manipulated to control the angle and/or position of the guard plate 305. The knob 303 can be positioned between the guard arm 302 and the body 304 proximate to the guard handle 301. A guard plate pivot point 401 may connect the guard plate 305 to the guard body 304. In some embodiments there are two or more pivot points 401 connecting the guard plate to the guard body 304.

In certain embodiments, the guard plate 305 and the knob 303 are connected by a pivoting arm (see FIG. 6A) so that when the knob 303 is turned, the guard plate 305 pivots in response. The pivot point 401 may connect the pivoting arm to the guard plate 305. As the pivoting arm moves up and down, the guard plate 305 moves about the pivot point 401. Several angles of the guard plate 305 may be possible through adjustment of the knob and pivoting arm.

In some embodiments, during a decompression procedure, the guard 300 is advanced through the tissue path and placed proximate to the target anatomy (e.g., the lamina, spinous process, or facet) once it is exposed. The guard plate 305 can be adjusted to fit under the target anatomy. For example, the guard 300 may be manipulated by the handle 301 or the body 304 to rotate and/or translate the guard 300. For example, the handle 301 may be manipulated to maneuver the guard 300 through muscle and other tissue.

In certain embodiments, the guard plate 305 can be rotated (e.g., about the pivot point 401), articulated, and/or otherwise maneuvered to pivot up or down to pass under the lamina or other target anatomy, for example, by manipulation of the knob 303. In certain embodiments, the guard plate 305 can be positioned to contact a side (e.g., underside) of the target anatomy to create a safety stop for instruments driven through the opposite side (e.g., top side) of the target anatomy to prevent damage to surrounding tissue, organs, bones, or other body parts (e.g., dura, nerve roots, etc.). The guard plate 305 can be positioned around the target anatomy to accommodate various angles for the protection of surrounding internal anatomy. Once the guard plate 305 is in the desired position. The orientation of the guard plate 305 can be fixed or locked.

In certain embodiments, the distal end 307 of the guard 300 (e.g., a distal end of the guard plate 305) may be bulleted or tapered to pass through or dissect muscle or other tissue. In certain embodiments, the guard plate 305 can be flat, convex, concave, and/or come in a variety of shapes to accommodate different anatomies or regions of the spine. In certain embodiments, a plurality of guards 300 having different shapes, dimensions, and/or other features may be provided for different anatomies or regions of the spine. In some embodiments, a plurality of guards 300 having guard bodies 304 of different lengths may be provided to treat different patients or reach different areas within the body.

Figure 4A:
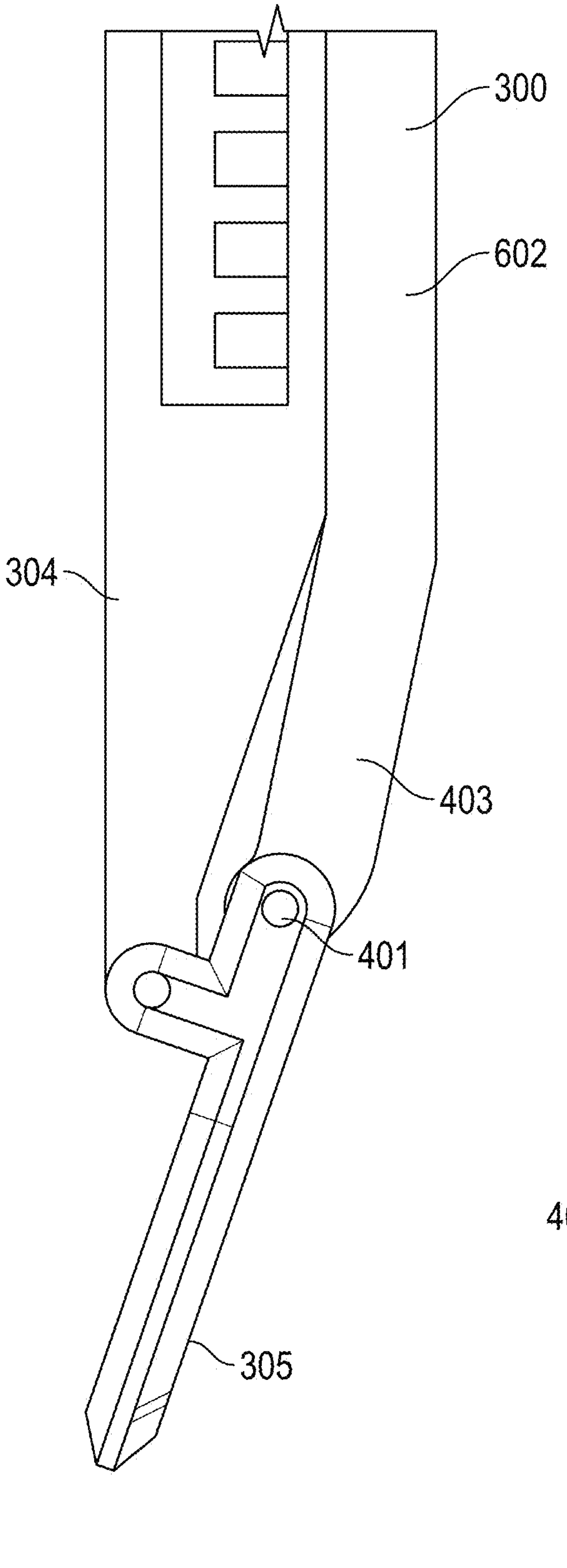
FIG. 4A depicts an enlarged side view of a distal end of the guard of FIG. 3.

In certain embodiments, as illustrated in FIG. 4A, the guard plate 305 may be in a first extended or straightened position upon insertion into the body. The first position of the guard plate 305 in relation to the guard body 304 allows the physician to advance the guard 300 parallel to or generally parallel to the lamina or target anatomy, which may be a precise and tight space.

In alternative embodiments, the guard plate 305 may not pivot relative to the guard body 304, but instead, the guard plate 305 may be fixed at a specific angle. In certain embodiments, the guard plate 305 is fixed at specific angles may be integrally formed with the guard body 304. In certain embodiments, a plurality of guards 300 with fixed guard plates 305 having different predetermined angles may be provided. Fixed guard plates 305 having different predetermined angles may be used for different anatomies. In certain embodiments, a fixed guard plate 305 may have a reduced risk of breaking or damaging in comparison to a pivoting guard plate 305. The fixed angles include one or more of 15 degrees, 30 degrees, 45 degrees, 60 degrees, 75 degrees, 90 degrees, less than 15 degrees, between 0 degrees and 30 degrees, between 15 degrees and 30 degrees, between 30 degrees and 45 degrees, between 45 degrees and 60 degrees, between 60 degrees and 75 degrees, between 75 degrees and 90 degrees, between 15 degrees and 90 degrees, between 30 degrees and 60 degrees, between 60 degrees and 90 degrees, between 45 degrees and 90 degrees, or any other suitable angle.

In some embodiments, the guard body 304 may have a distal area 403 that is designed to be textured, knurled, have teeth, or have other features to help grip the bone and prevent slipping upon insertion. Alternatively, the distal area 403 may be feature-free to allow for smoother insertion and removal of the guard.

Figure 4B:
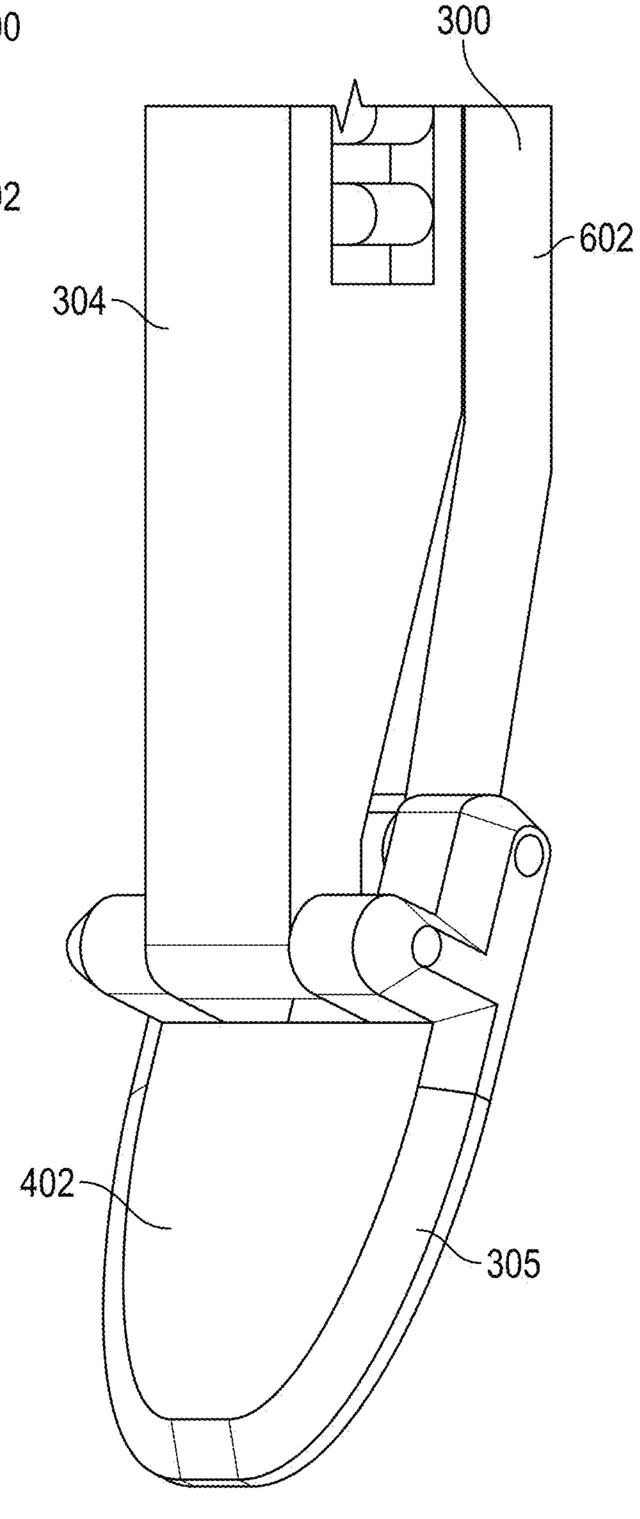
FIG. 4B depicts an enlarged perspective view of the distal end of the guard of FIG. 3.

As illustrated in FIG. 4B, the guard plate 305 can include a top surface 402. The top surface 402 can be positioned to contact the bottom of the lamina or target anatomy when the guard plate 305 is pivoted from the first position to a second position. Once the guard plate 305 is pivoted under the target area (e.g., the lamina), the guard plate 305 can be fixed into position and serve as a stopping point during later steps of the surgical procedure (e.g., laminotomy).

In certain embodiments, the guard plate 305 may take on other shapes and configurations. In certain embodiments, the guard plate 305 may contain features for gripping to the bone. Alternatively, the guard plate may be specifically dimensioned for the size and shape of the anatomy being targeted.

Figure 5B:
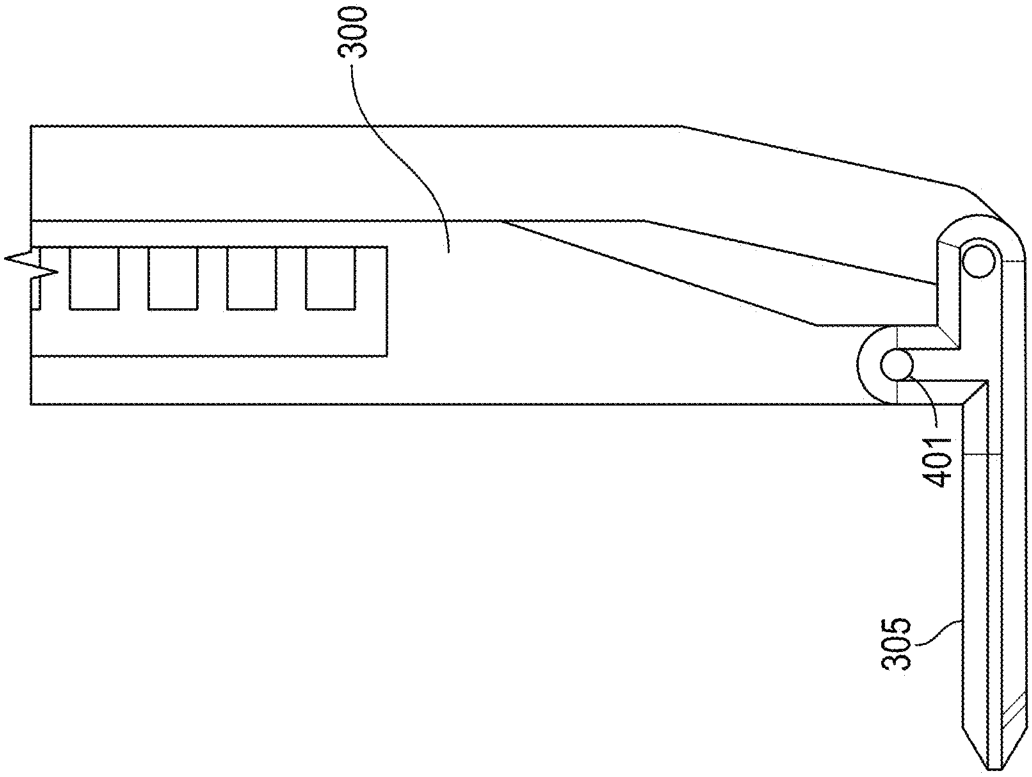
FIG. 5B depicts an enlarged side view of the distal end of the guard of FIG. 3.
Figure 5A:
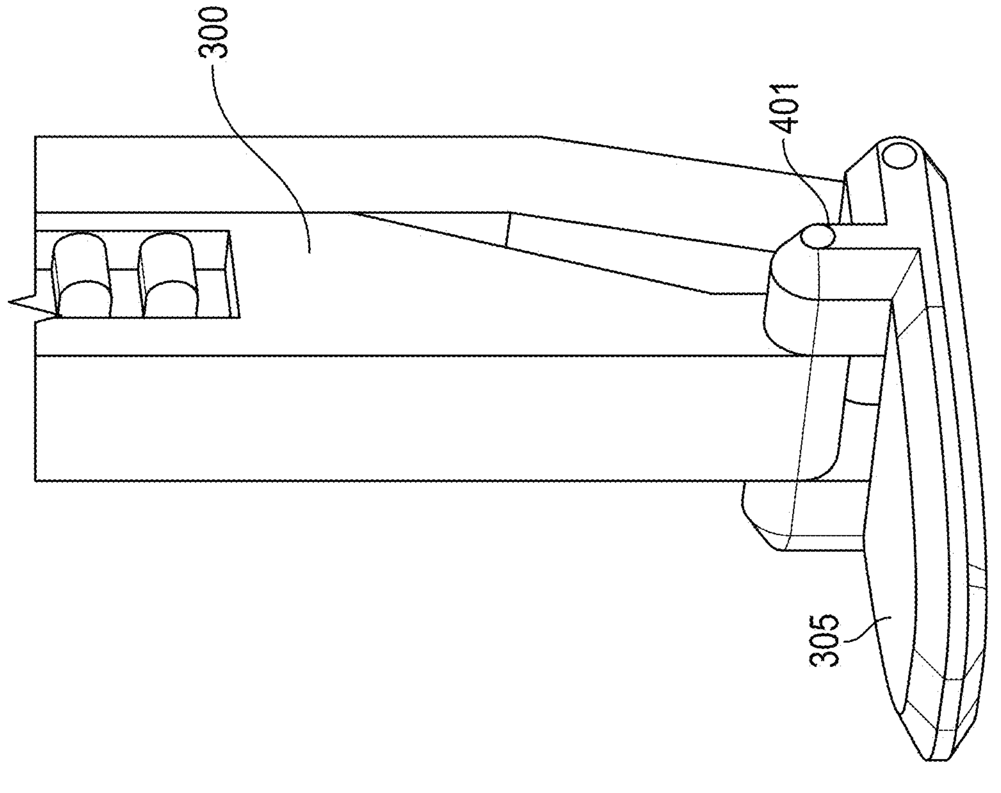
FIG. 5A depicts an enlarged perspective view of the distal end of the guard of FIG. 3.

Referring now to FIGS. 5A and 5B, the guard plate 305 is shown pivoted from the first position to a second pivoted position. In the second pivoted position, a longitudinal axis of the guard plate 305 may be perpendicular to or generally perpendicular to a longitudinal axis of the guard body 304. In certain embodiments, once the guard plate 305 is positioned proximate to the target anatomy, the doctor may twist the knob to cause the guard plate 305 to pivot to the second position so that the top surface 402 contacts the underside of the target anatomy. The guard plate 305 and/or the guard 300 may then be locked into place around the target anatomy.

In certain embodiments, the guard plate 305 may be pivoted to any angle between the extended position of FIG. 4A and a max pivot position, depending on the length and capabilities of the pivot mechanism present in the guard body 304.

Figure 6B:
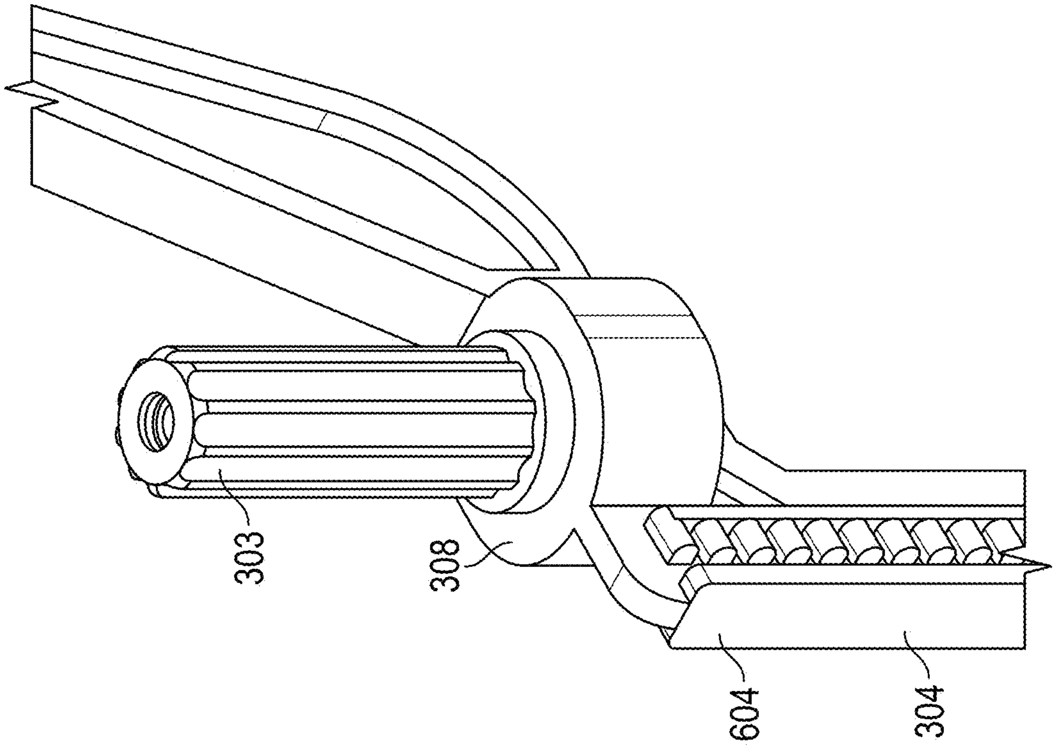
FIG. 6B depicts an enlarged perspective view of a proximal portion of the guard of FIG. 3.
Figure 6A:
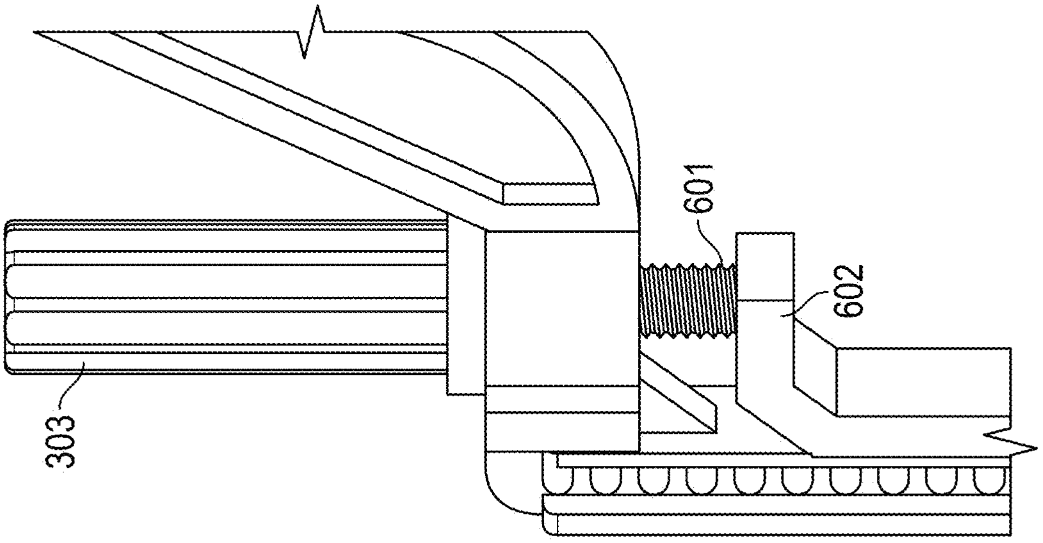
FIG. 6A depicts an enlarged side view of a proximal portion of the guard of FIG. 3.

Referring now to FIG. 6A, the knob 303 may be attached to a pivoting arm 602 by a knob screw 601. When the physician wants to change the angle of the guard plate 305, the physician may rotate the knob 303, which in turn rotates the knob screw 601, and causes the pivoting arm 602 to move towards the distal end of the guard. As the pivoting arm 602 moves toward the distal end, the top surface of the guard plate 305 pivots up towards the guard body 304. If the doctor rotates the knob 303 in the opposite direction, rotation of the knob screw 601 will cause the pivoting arm 602 to move towards the proximal end of the guard 300 and the top surface of the guard plate 305 to rotate away from the guard body 304.

In alternative embodiments, other control mechanisms (e.g., buttons, switches, triggers, levers, etc.) may be used to change the angle of the guard plate 305.

In some embodiments, the guard 300 may act as an instrument shuttle. As shown in FIG. 6B, the guard body 304 may contain a track 604. The track 604 can allow for additional instruments to couple to and advance along the guard 300 to the target area. For example, in certain embodiments, a working channel can be coupled to and advanced along the track 604. For example, once coupled, the working channel can be advanced to contact a side (e.g., top side) of the target area (e.g., the lamiae, facet, etc.) opposite the guard plate 305. The working channel can be secured on the opposite side from the guard plate 305 to provide a clear path to the target anatomy for the decompression procedure and/or provide further protection to the surrounding anatomy. In certain embodiments, the guard plate 305 may act as an engagement feature for engaging with or securing to the target anatomy to provide a stable and consistent path towards the target anatomy for instruments advancing along the guard 300 (e.g., via the track 604).

Figure 7A:
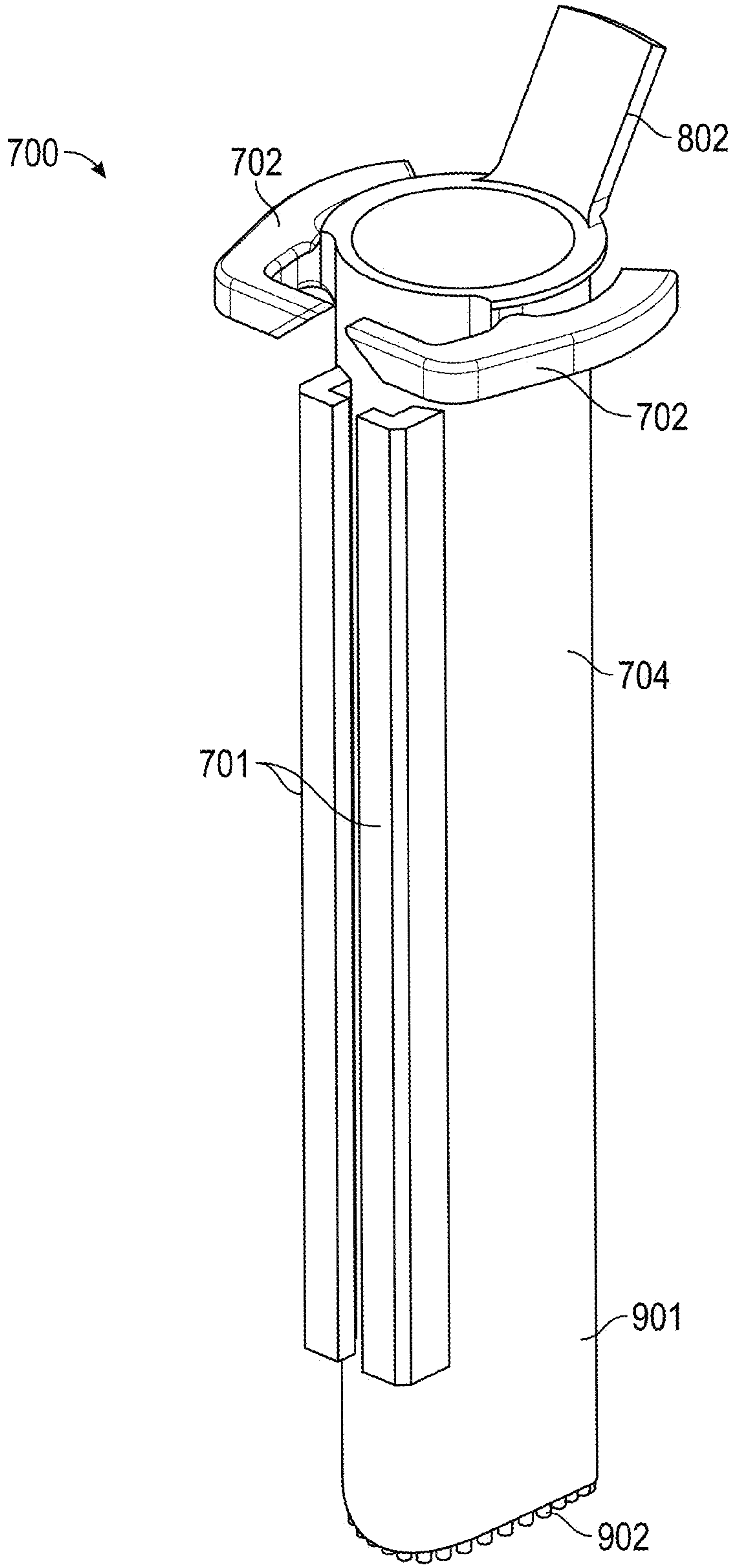
FIG. 7A depicts a perspective view of an embodiment of a working channel.
Figure 7B:
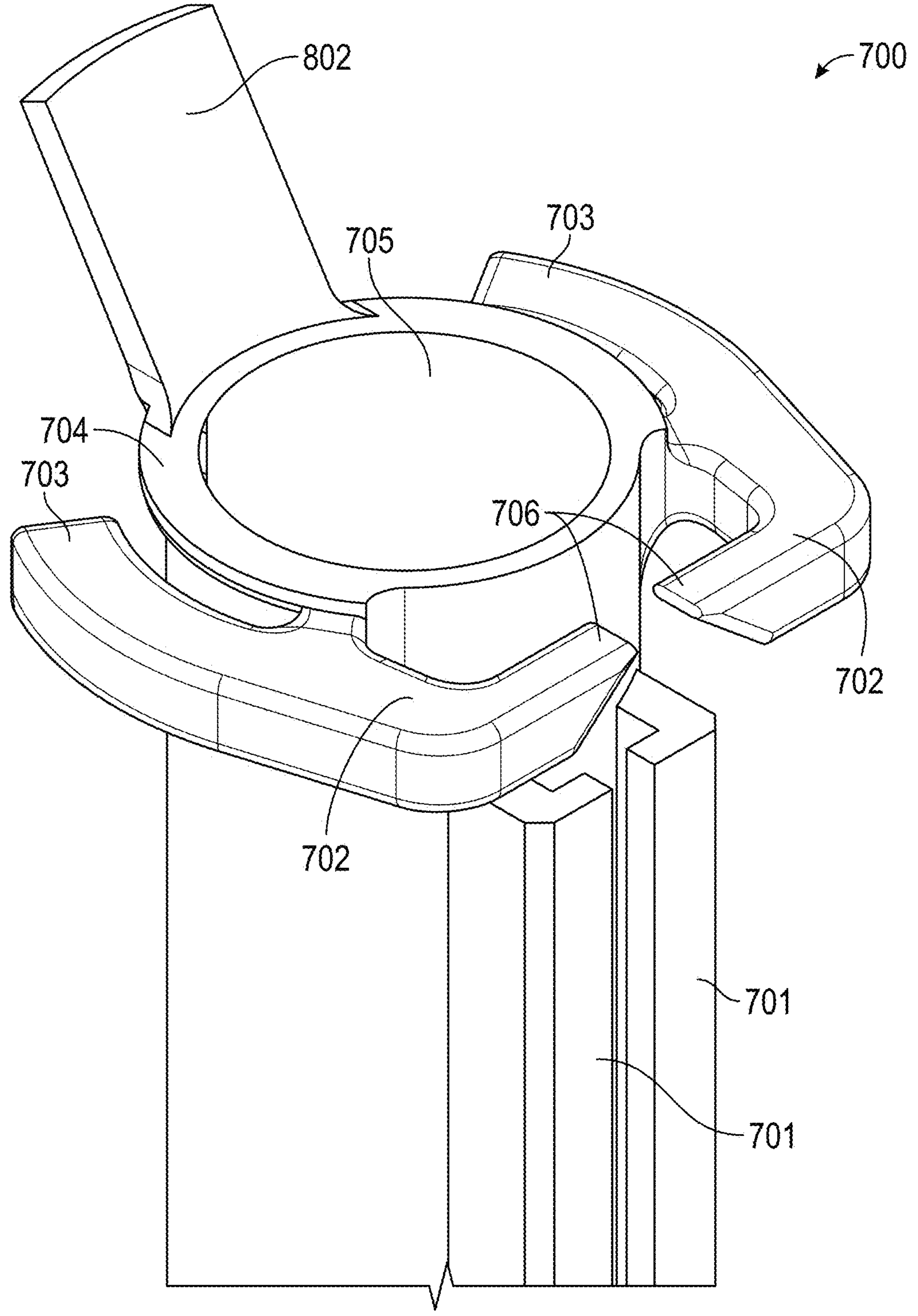
FIG. 7B depicts an enlarged perspective view of a proximal end of the working channel of FIG. 7A.

Referring to FIG. 7A, a perspective view of a working channel 700 is depicted. A perspective view of a proximal portion of the working channel 700 is depicted in FIG. 7B. In certain embodiments, the working channel 700 may have a channel body 704. The channel body 704 may be tubular or generally tubular in shape. One or more instruments may be advanced through the channel body 704 to the target area as further described herein. In some embodiments, the working channel 700 can be a dilator.

In certain embodiments, the working channel 700 can include a track coupler 701 extending down an external length of the channel body 704. The track coupler 701 may couple with the track 604.

Figure 8B:
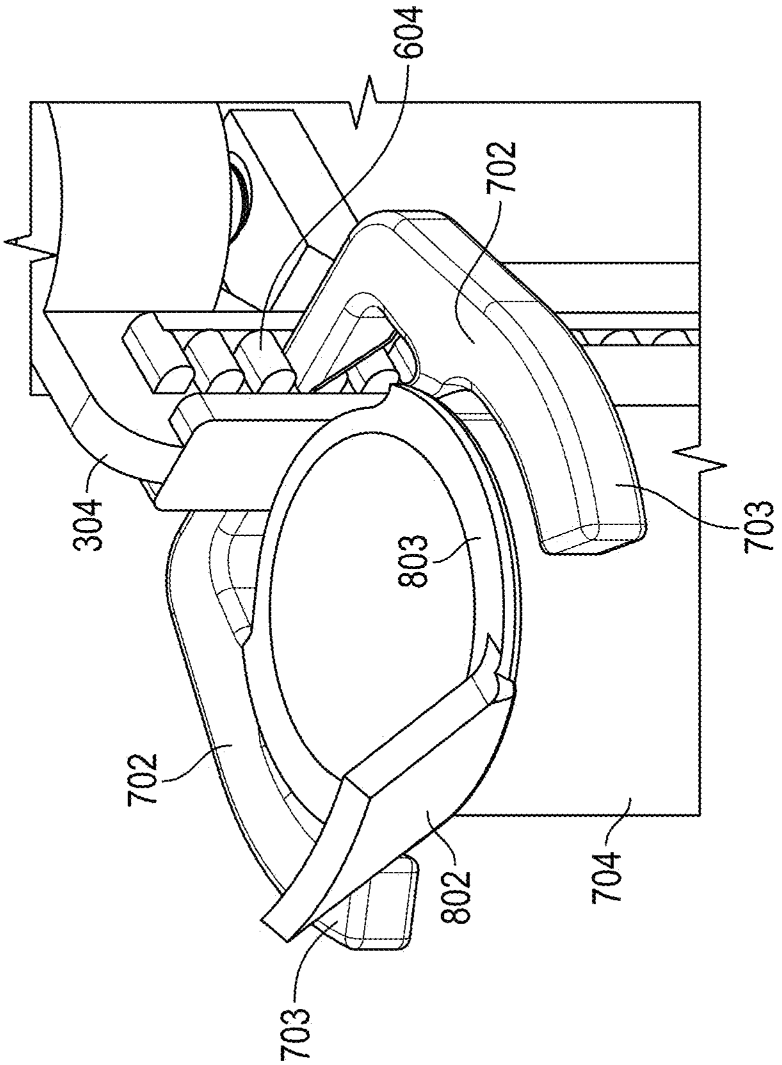
FIG. 8B depicts an enlarged perspective view of a proximal portion of the decompression system of FIG. 8A.
Figure 8A:
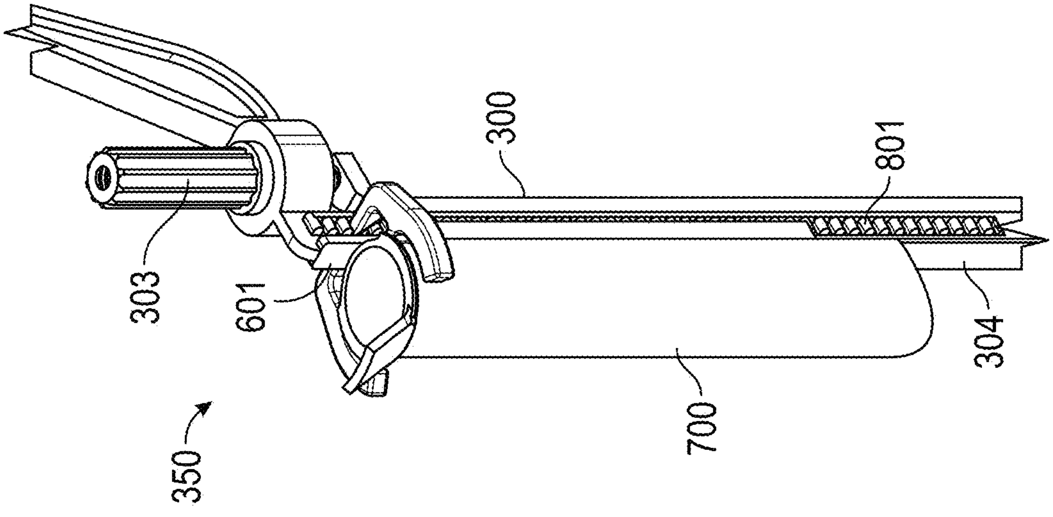
FIG. 8A depicts a perspective view of a portion of a decompression system including the guard of FIG. 3 and the working channel of FIG. 7A.

As shown in FIG. 8A, in some embodiments, the track 604 can include a plurality of grooves 801. The grooves 801 may allow for additional instruments to couple to and advance along the track 604. In some embodiments, the grooves 801 may be alternating male and female grooves that allow an instrument (e.g., the working channel 700) to engage the track 604 and releasably secure to a fixed position along the track 604 (e.g., when not advancing or retracting along the track 604 as described herein). The working channel 700 can be releasably secured to the track 604 to prevent unintended retraction and/or advancement.

In certain embodiments, the working channel 700 and guard 300 can together form a guide system or decompression system 350. As described herein, the decompression system 350 can engage a target area and protect the surrounding anatomy while acting as a guide for additional instruments for a decompression procedure.

The working channel 700 can include track coupling arms 702 configured to engage with the track grooves 801 of the track 604. In certain embodiments, two track arms 702 may be positioned around an opening 705 of the channel body 704. The track arms 702 can provide a locking mechanism for releasably fixing a positioning the working channel 700 along the track 604. For example, in certain embodiments, ends or tips 706 of the track arms 702 can engage the grooves 801 to fix the position of the working channel 700 along the track 604, as shown for example in FIGS. 8A-8B. The tips 706 can be male engagement members configured to engage with female grooves 801 of the track 604. In certain embodiments, open ends 703 of the track arms 702 may be manually pinched inward toward the opening 705 of the channel body 704 so that tips 706 of the track arms 702 spread apart and release from the grooves 801. In the pinched position, the working channel 700 can be advanced along the track. When the open ends 703 are released, the tips 706 of the arms can engage the grooves 801 and the working channel 700 can be locked or secured into place. The grooves 801 may serve as a series of fixed positions to which the working channel may fix.

Referring to FIG. 8B, a magnified view of the working channel 700 coupled to the guard body 304 via the track 604 is depicted. A lip 802 may protrude from the top surface 803 of the channel body 704. In some embodiments, one or two light sources may be affixed to the lip 802 to improve visibility around the surgical site. Lights may be disposable or reusable and affixed to the lip 802 through clips or other fastening mechanisms. In other embodiments, loupes or a microscope may be coupled to the lip 802 to facilitate visualization of the surgical site.

Figure 9A:
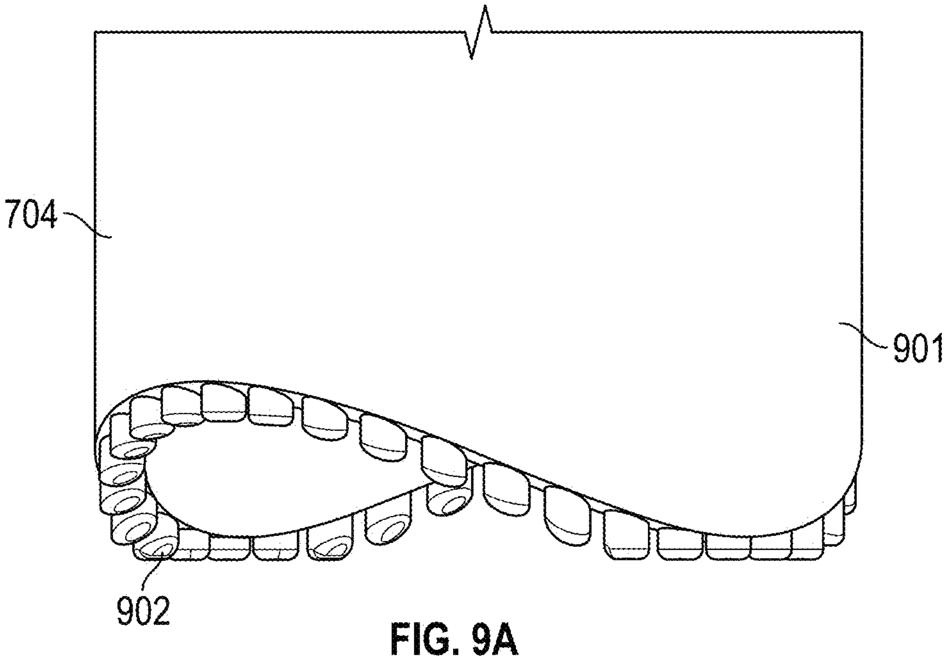
FIG. 9A depicts an enlarged side view of a distal end of the working channel of FIG. 7A.
Figure 9B:
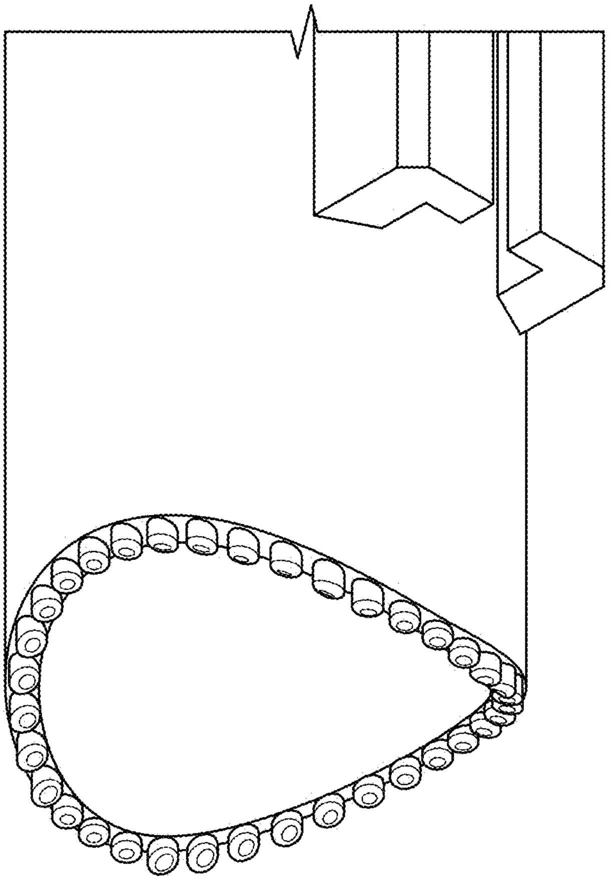
FIG. 9B depicts an enlarged perspective view of the distal end of the working channel of FIG. 7A.

FIG. 9A and FIG. 9B depict a distal end 901 of the channel body 704. The distal end 901 may contact a side of the target area opposite of the guide plate 305. In certain embodiments, the distal end 901 of the channel body 704 can include one or more surface features 902. The surface features 902 may be protrusions or teeth to prevent slipping when positioned against bone. In some embodiments, the surface features 902 can be rough, abrasive, or otherwise textured surfaces to prevent slipping when positioned against the bone. In some embodiments, the surface features 902 may be a non-slip material.

The distal end 901 may be irregular (e.g., not flat), to better grip the bone. In certain embodiments, the distal end 901 may be concave and/or convex in shape to match the shape of the target area (e.g., the lamina).

The surface features 902 may vary in number and be various shapes and dimensions depending on the application. For example, in some embodiments, the working channel 700 may contain no surface features at the distal end.

In certain embodiments, the working channel may be between 30 mm and 120 mm in length. In certain embodiments, working channels of various lengths can be provided to accommodate different medical instruments.

Figure 10:
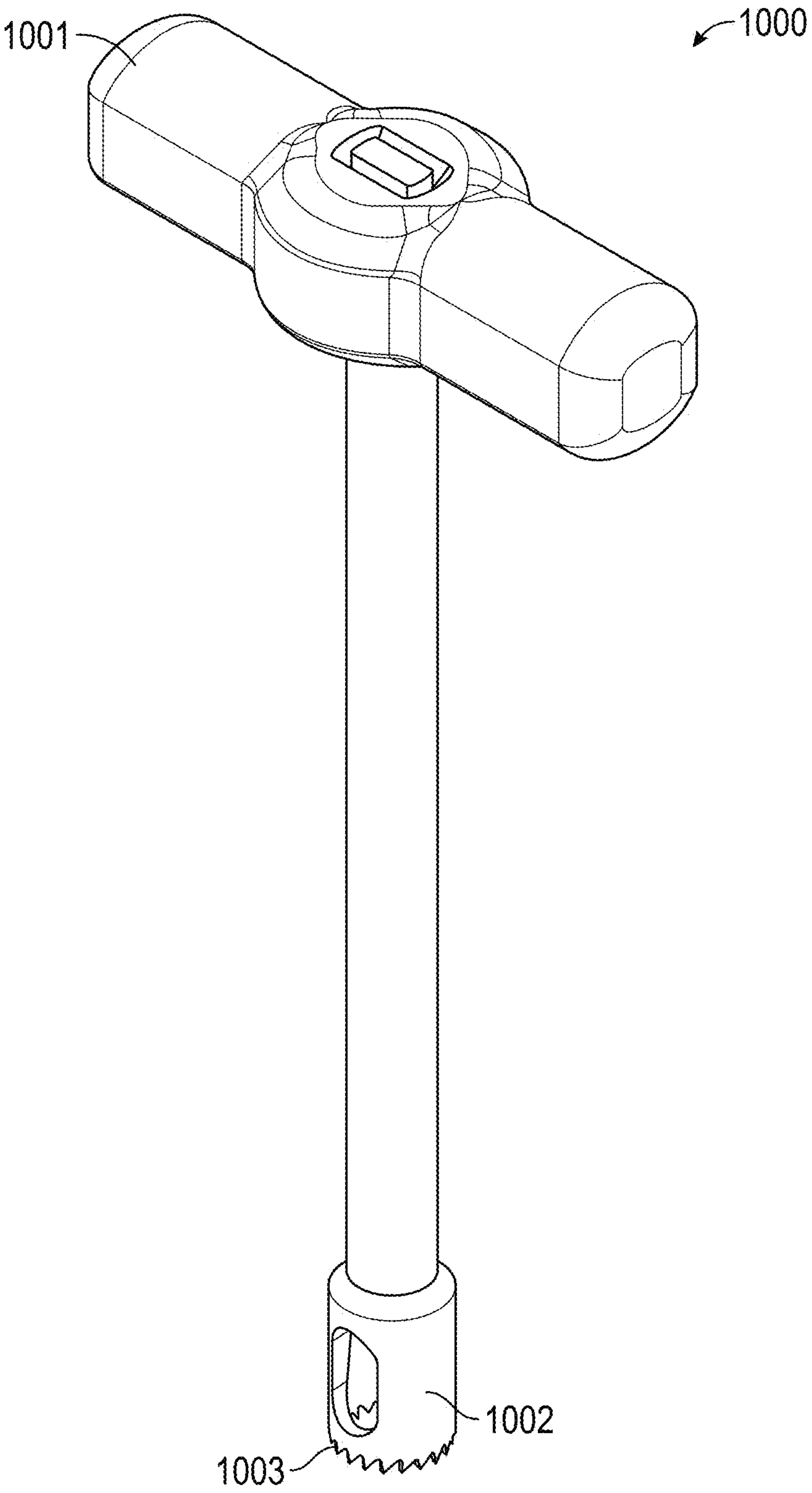
FIG. 10 depicts a perspective view of an embodiment of a trephine.
Figure 11D:
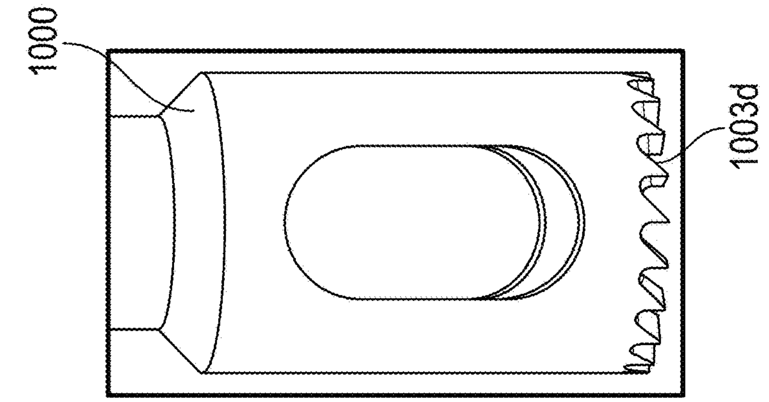
FIG. 11D depicts an enlarged side view of an embodiment of a distal end of the trephine of FIG. 10.
Figure 11C:
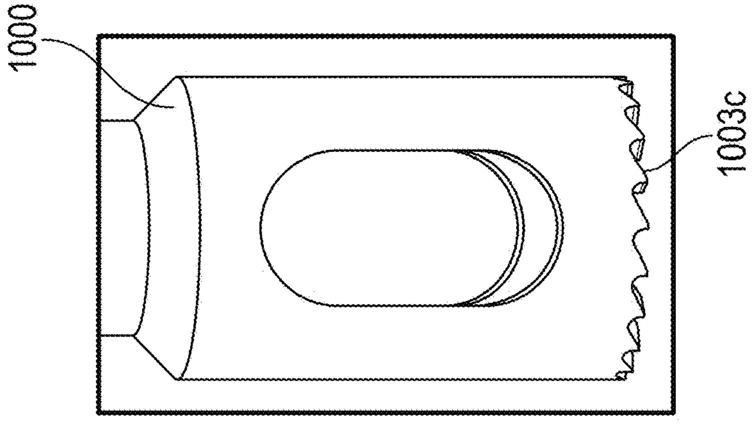
FIG. 11C depicts an enlarged side view of an embodiment of a distal end of the trephine of FIG. 10.
Figure 11B:
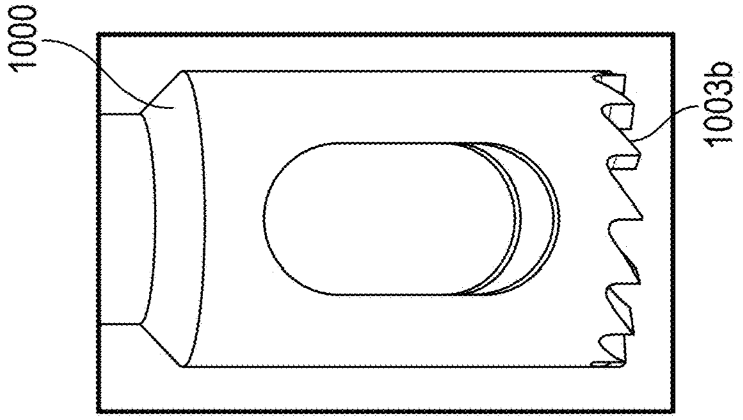
FIG. 11B depicts an enlarged side view of an embodiment of a distal end of the trephine of FIG. 10.
Figure 11A:
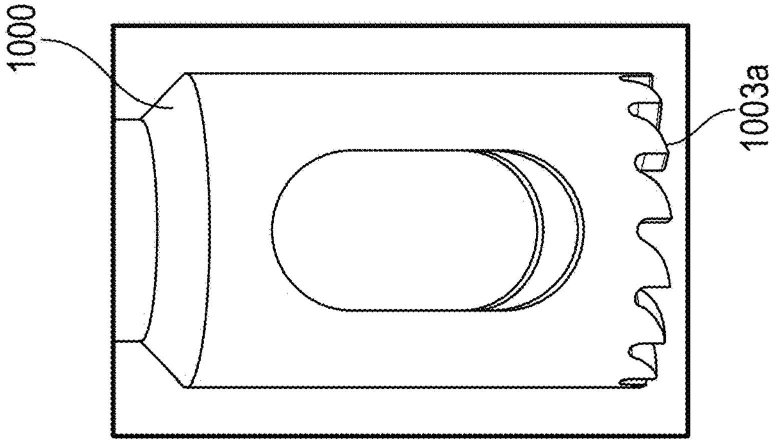
FIG. 11A depicts an enlarged side view of an embodiment of a distal end of the trephine of FIG. 10.

Referring to FIG. 10, in certain embodiments a trephine 1000 may be advanced down the working channel 700 to the target area. After advancing the trephine 1000 to the target area, the trephine 1000 can be used to remove at least part of the bone (and/or other target anatomy) at the target area. For example, after the trephine 1000 is advanced to the target area, the trephine 1000 may be rotated around a longitudinal axis through the center of the trephine 1000 by gripping and rotating a handle 1001. In certain embodiments, the trephine 1000 can be rotated back and forth to create a cutting effect. The distal end 1002 of the trephine 1000 can contain a cutting edge 1003. The cutting edge may include one or more cutting features, such as teeth. As the trephine 1000 is rotated and cuts into the bone, the cut bone can become lodged in the distal end 1002 of the trephine. In certain embodiments, the trephine 1000 can be used to cut through the bone at the target area until it contacts the guard plate 305 on the opposite or bottom side of the target anatomy. As described herein, the guard plate 305 can act as a safety stop to prevent nerve, spinal cord, or surrounding anatomy damage by the trephine 1000. After the trephine 1000 contacts the guard plate 305, the trephine 1000 can be withdrawn and removed from the working channel 700. Removal of the bone at the target area can create the desired space to treat the spinal stenosis.

Once the trephine 1000 is withdrawn, the working channel 700 may provide visibility for a doctor to see if more bone or tissue, such as ligamentum flavum, needs to be removed.

Other medical devices may be inserted down the working channel 700 in addition to or alternatively to the trephine 1000, such as a drill, kerrison, burr, or other instrument to cut or alter the target anatomy as desired. In some embodiments, several different medical devices may be used in succession in conjunction with the working channel 700. For example, in certain embodiments, different devices may be used to perform different steps of a procedure or to achieve different results. For example, if more tissue or bone needs to be removed after use of the trephine 1000, the doctor may use a kerrison or pituitary subsequently to debulk the target anatomy.

As illustrated in FIGS. 11A through 11D, the trephine 1000 may have different types of cutting edges 1003*a-d* present at the distal end. The cutting edges may contain teeth that are wider or shallower depending on the desired cutting effect. In certain embodiments, the teeth may be angled at different degrees to accommodate different portions of the spine. For example, a trephine with teeth angled at a first angle may be used for the L3 and L4 spinal motion segments while a trephine with teeth angled at a second angle may be used for the L4 and L5 spinal motion segments. In some embodiments, the teeth may be sharper, more curved, or cut in a specific pattern to achieve a desired cutting effect. In some embodiments, the trephine may not contain teeth at the distal end and may have some other feature to alter the target anatomy. In certain embodiments, a plurality of trephines may be provided having different cutting edges for use on different anatomies, at different locations, and/or for different cutting effects.

Figure 12:
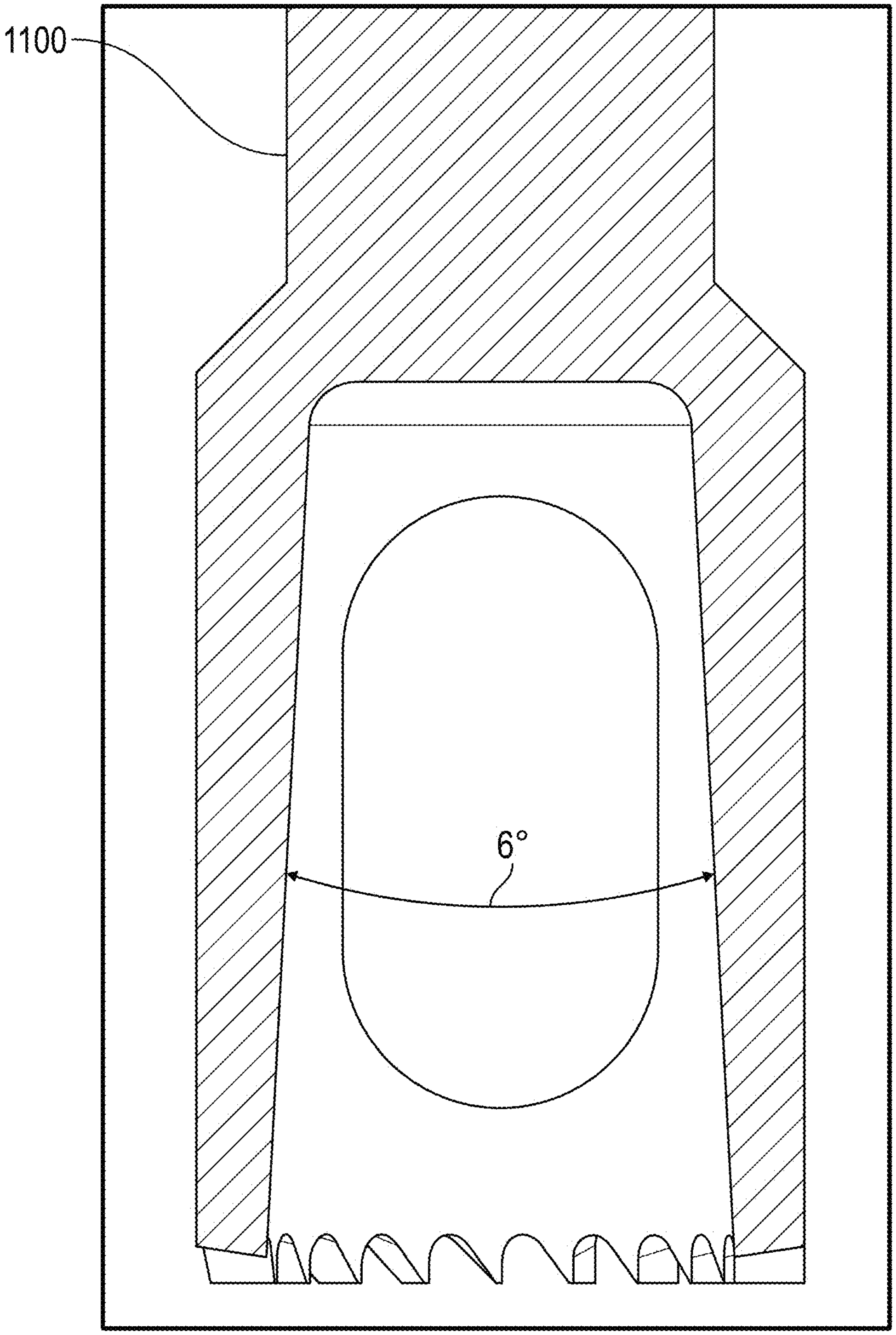
FIG. 12 depicts an enlarged cross-sectional view of the distal end of the trephine of FIG. 10.

FIG. 12 illustrates a cross-sectional view of the trephine 1000. As shown, a conical angle of the depicted trephine is 6°. However in alternative embodiments, the angle may be more or less than 6 degrees (e.g., between 1 degree and 36 degrees, 2 degrees and 18 degrees, or any other suitable angle). As the conical angle changes, the overall size of the distal end of the trephine changes, and consequently, the amount of bone removed.

In some embodiments, after the desired amount of bone is removed, the working channel 700 may be detached from the guard 300, then the guard 300 removed from the surgical site.

Figure 13A:
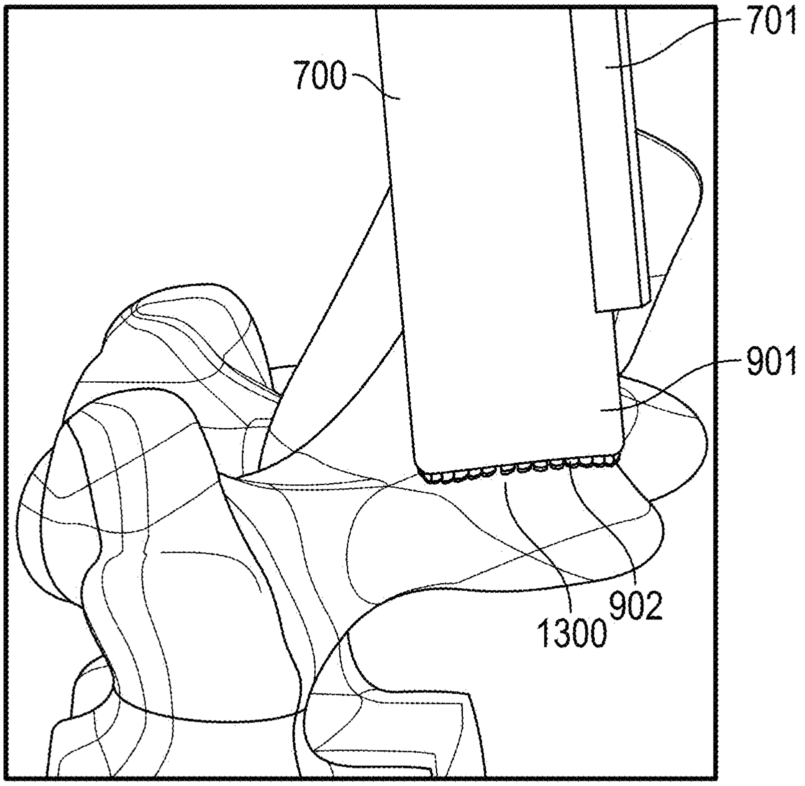
FIG. 13A depicts an example of the working channel of FIG. 7A positioned adjacent to a target anatomy for a decompression procedure.

FIG. 13A illustrates an example of the distal end 901 of the working channel 700 in contact with target anatomy 1300. In certain embodiments for example, the target anatomy 1300 may be a lamina in the spine, as shown in FIG. 13A. The features 902 protruding from the proximal end may contact the bone or tissue at the target anatomy 1300. As previously indicated, the features 902 may be specifically configured (e.g., shaped, dimensioned, or composed of a certain material) so that the features 902 grip onto the target anatomy 1300. Additionally, the distal end 901 may be contoured to align with the specific shape of the target anatomy 1300. In certain embodiments, the working channel 700 may be positioned at other areas or sides of the target anatomy 1300 than those illustrated in FIG. 13A.

Figure 13B:
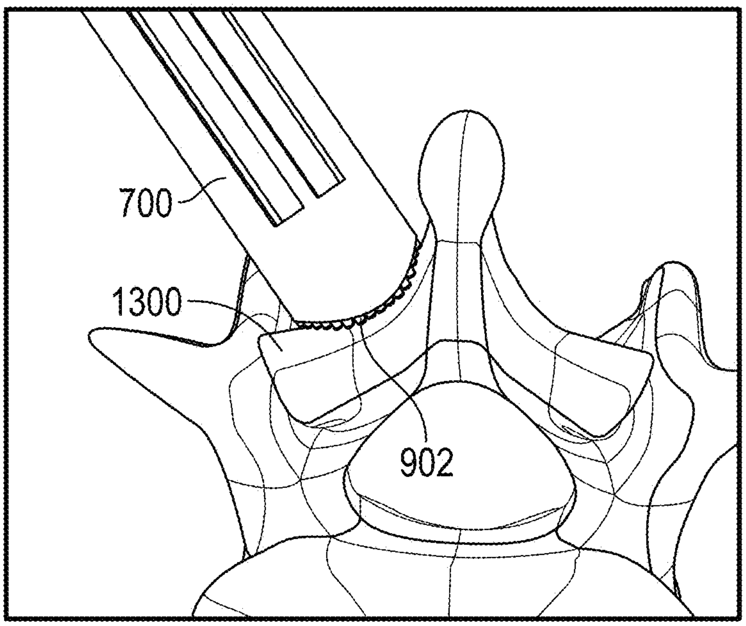
FIG. 13B depicts an example of the working channel of FIG. 7A positioned adjacent to the target anatomy.

FIG. 13B illustrates an alternative angle of the working channel 700 contacting the target anatomy 1300. In some embodiments, the distal end 901 of the working channel 700 may be sloped or curved to nest into the target anatomy 1300 (e.g., the lamina in FIG. 13B). In certain embodiments, the distal end 901 may be shaped so that the features 902 make contact with the target anatomy. In some embodiments, only some of the features 902 may contact the target anatomy.

Figure 14A:
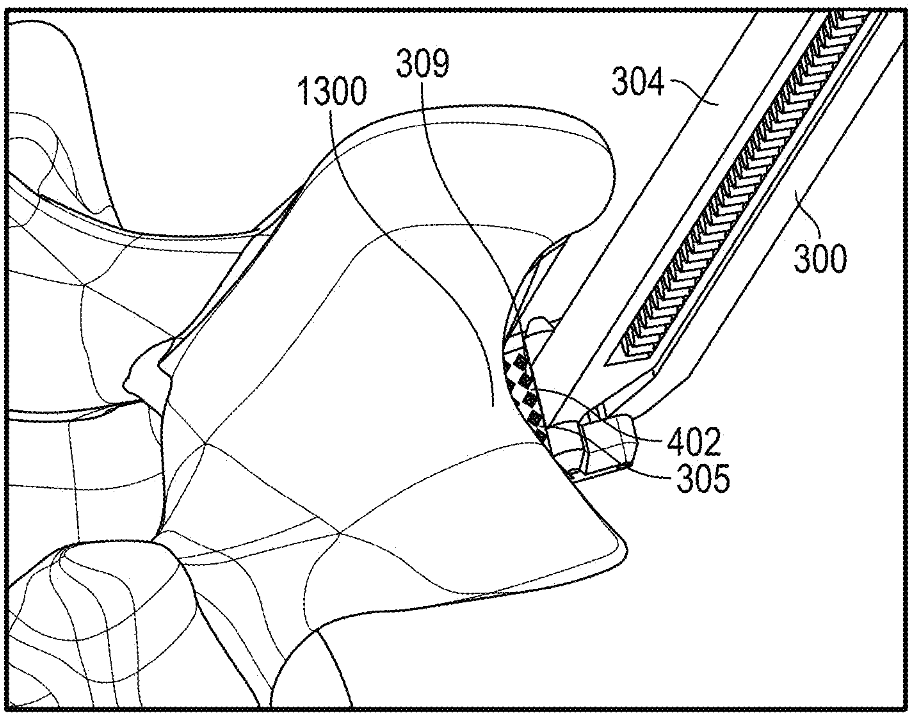
FIG. 14A depicts an example of the guard of FIG. 3 positioned adjacent to the target anatomy.

FIG. 14A illustrates the guard 300 positioned against the target anatomy 1300. As shown in FIG. 14A, the target anatomy 1300 may be a lamina. As previously described, the guard plate 305 may be positioned against the target anatomy 1300. When the guard plate 305 is positioned against the target anatomy 1300, the guard plate may minimize movement of the guard 300 in at least some directions. The guard plate 305 may contain surface features 309 on the top surface 402. The surface features 309 may be protrusions or teeth to prevent slipping when positioned against bone. In some embodiments, the surface features 309 can be rough, abrasive, or otherwise textured surfaces to prevent slipping when positioned against the bone. In some embodiments, the surface features 309 may be a non-slip material. The surface features 309 can improve the grip and surface contact with the target anatomy. In certain embodiments, the surface features 309 can act as engagement features for engaging with or securing to the target anatomy to provide a stable and consistent path towards the target anatomy for instruments advancing along the guard 300 (e.g., via the track 604). In alternative embodiments, the guard 300 and guard plate 305 may be positioned at other areas along the target anatomy.

Figure 14B:
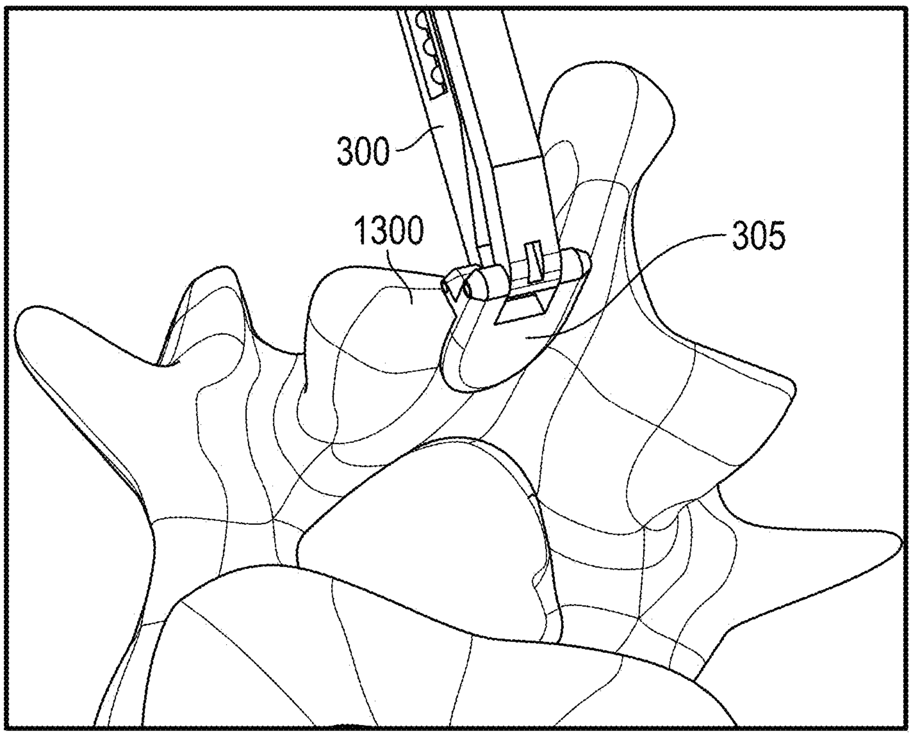
FIG. 14B depicts an example of the guard of FIG. 3 positioned adjacent to the target anatomy.

Referring to FIG. 14B, another angle of the guard 300 positioned against the target anatomy 1300 is illustrated. The bottom of the guard plate 305 may be unobstructed as the top surface of the plate contacts the bottom of the target anatomy 1300.

Figure 15A:
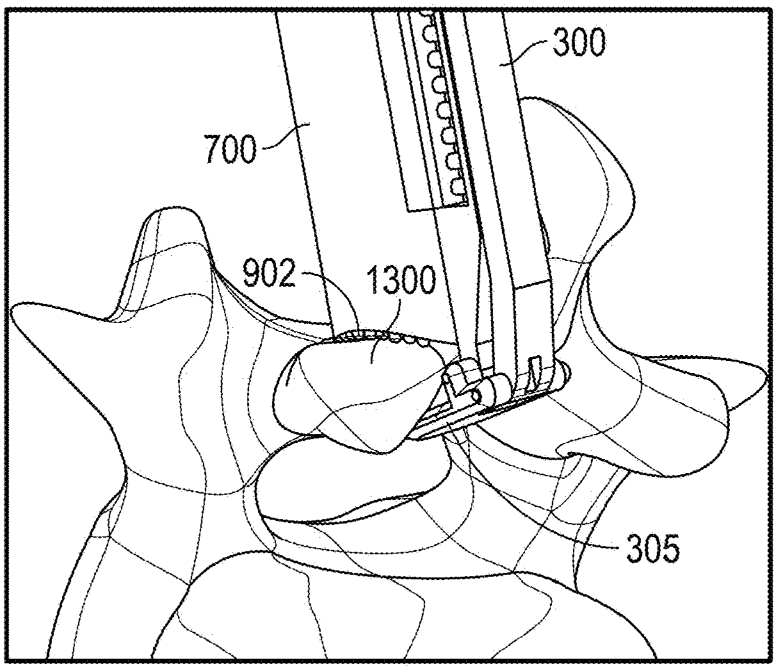
FIG. 15A depicts an example of the decompression system of FIG. 8A positioned adjacent the target anatomy.

FIG. 15A illustrates the guard 300 coupled to the working channel 700 positioned against the target anatomy 1300. In certain embodiments, the target anatomy 1300 may be clamped between the distal end 901 of the working channel 700 and the top surface 402 of the guard plate 305. For example, in some embodiments, the target anatomy 1300 can be clamped between the surface features 902 and the surface features 309. When the guard 300 and working channel 700 are positioned, the working channel 700 can provide a path for other surgical tools to align with and access the target anatomy 1300. Additionally, the guard 300 and working channel 700 may protect surrounding anatomy from contact or damage during the surgical procedure. Using the guard in conjunction with the working channel during a procedure may provide support and alignment for other surgical tools.

Figure 15B:
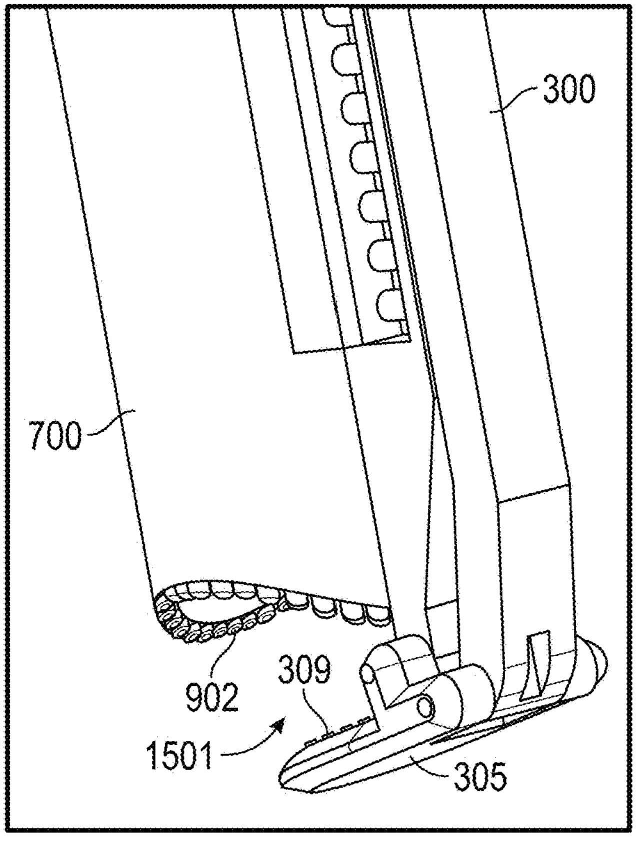
FIG. 15B depicts a perspective view of a distal end of the decompression system of FIG. 8A.

FIG. 15B illustrates the guard 300 coupled to the working channel 700, as illustrated in FIG. 15A, but without the target anatomy 1300. FIG. 15B shows a space 1501 between the top of the plate 305 and the features 902 of the working channel 700. The space 1501 can be increased or decreased by moving the working channel 700 proximally or distally, respectively, along the track 604.

Figure 16:
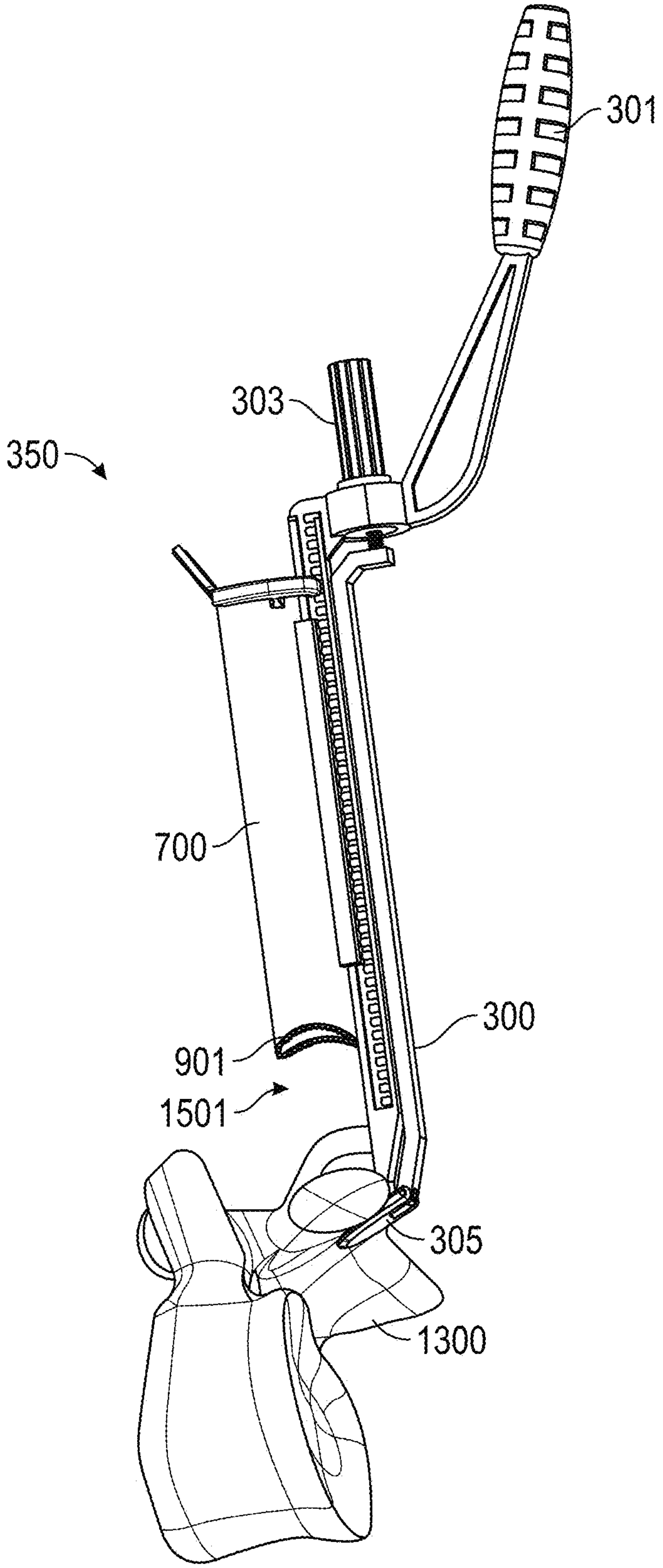
FIG. 16 depicts a perspective view of the decompression system of FIG. 8A positioned adjacent to the target anatomy.

FIG. 16 illustrates the guard 300 coupled to the working channel 700 and positioned around the target anatomy 1300. As shown in FIG. 16, the working channel 700 is positioned so that the distal end 901 is spaced apart from the target anatomy 1300. As shown in FIG. 16, the guard plate 305 is positioned in contact with one side (e.g., the underside) of the target anatomy 1300. The working channel 700 may be lowered (e.g., advanced distally along the track 604) so that the space 1501 between the distal end 901 and the guard plate 305, and consequently the space between the distal end 901 and the target anatomy, decreases. The working channel 700 may be lowered until it contacts the opposite side (e.g., the top side) of the target anatomy 1300 from the guard plate 305. Lowering the working channel 700 into contact with the target anatomy 1300 may clamp the target anatomy between the working channel and the guard plate 305. In some embodiments, the working channel 700 may be lowered to squeeze the target anatomy (e.g., the lamina) between the working channel 700 and the guard plate 305. As shown in FIG. 16, the target anatomy may be a lamina of a patient.

As described with respect to FIGS. 8A-8B, in some embodiments the working channel 700 can be positioned at the target anatomy 1300 by maintaining the track arms 702 in an open configuration (e.g., by pinching the open ends 703), advancing the working channel 700 to contact the target anatomy 1300, and transitioning the track arms 702 to a closed configuration (e.g., by releasing the open ends 703) so that the track arms 702 engage the grooves 801 (e.g., via the tips 706) to secure the position of the working channel 700 along the track 604 and/or relative to the target anatomy 1300.

Figure 17A:
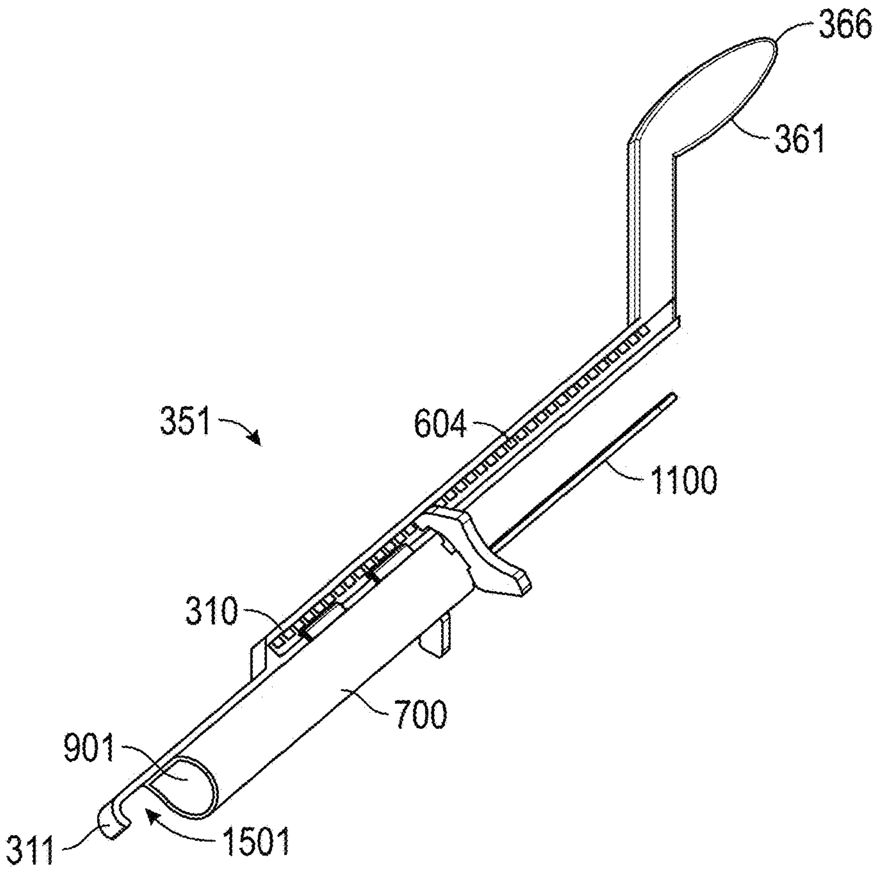
FIG. 17A depicts a perspective view of an embodiment of a decompression system.

FIG. 17A depicts another embodiment of a guide system or decompression system 351 that may be used in a surgical procedure. As shown in FIG. 17A, in some embodiments, the decompression system 351 can include an instrument shuttle 310. The instrument shuttle 310 can include features, such as a track, for coupling to additional instruments (such as a working channel) and advancing the additional instruments to the target area. For example, the instrument shuttle 310 may include a track 604, which may have any of the same and/or similar features and/or functions as the track 604 of the guard 300 and vice versa.

A proximal end 366 of the instrument shuttle 310 can include a handle 361 for manipulation by a user (e.g., a physician). The instrument shuttle 310 may be manipulated by the handle 361 to rotate and/or translate the instrument shuttle 310. For example, the handle 361 may be manipulated to maneuver the instrument shuttle 310 through muscle and other tissue.

In some embodiments, the decompression system 351 can include the working channel 700. The working channel 700 can couple to the instrument shuttle 310.

In certain embodiments, working channel 700 may advance up and down the instrument shuttle 310 to adjust the space 1501 between the distal end 901 of the working channel 700 and the target anatomy.

In some embodiments, the instrument shuttle 310 may have a hook 311 at its distal end. The hook 311 may be advantageous in procedures approaching inferior to the lamina. The hook 311 may be various sizes to easily couple to different sized or shaped bones. The hook 311 can engage with and/or secure to the target area or anatomy adjacent the target area. The hook 311 may secure the instrument shuttle 310 to provide a stable and consistent path towards to the target area for instruments advancing along the instrument shuttle 310.

In some embodiments, instrument shuttle 310 serves as a docking device for aligning the working channel 700 or other instrument coupled to the instrument shuttle 310. The hook 311 can be positioned under and contact (e.g., be slid under) that target anatomy at a fixed angle. Once the hook 311 is positioned on the desired bone, the working channel 700 may be advanced down the track 604. The target anatomy can be positioned between the distal end 901 of the working channel 700 and the hook 311. While a hook 311 is described with respect to the instrument shuttle 310, in certain embodiments, the instrument shuttle 310 may have alternative and/or additional engagement features, such as fasteners, teeth, protrusions, grips, textured surfaces, etc. for engaging with the anatomy.

Figure 17B:
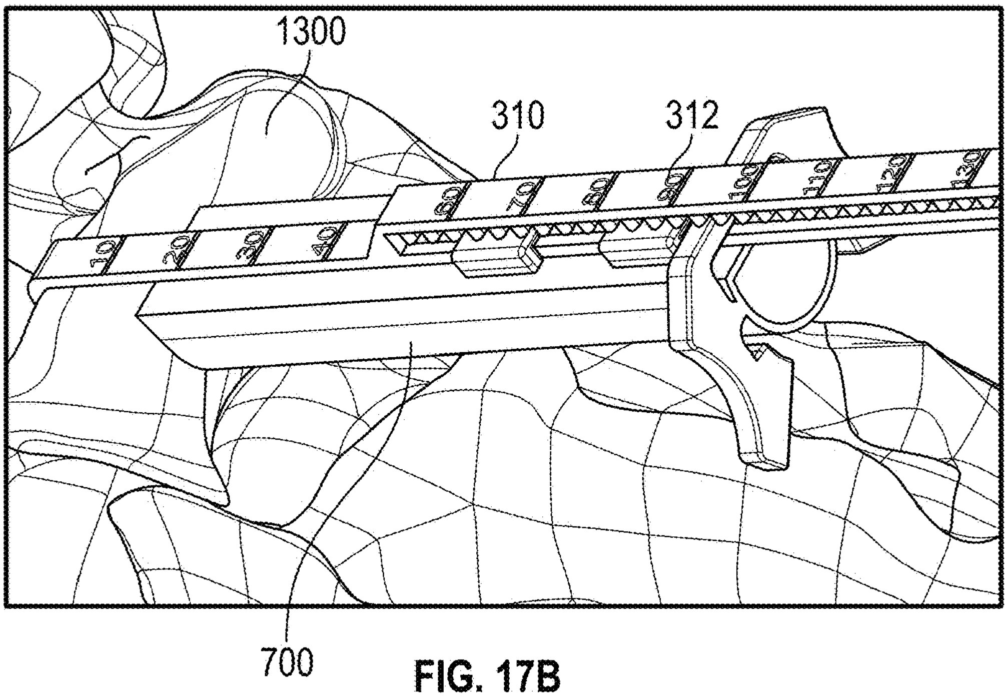
FIG. 17B depicts an example of the decompression system of FIG. 17A positioned adjacent to the target anatomy.

As shown in FIG. 17B, in certain embodiments in which the target area is a lamina, the hook 311 may be advanced over the superior side the lamina before engaging with the lamina.

Referring to FIG. 17B, when the working channel 700 is coupled to instrument shuttle 310 around the target anatomy 1300, the working channel 700 may be angled cephalad up the spine. Hook 311 can direct the working channel 700 to the desired angle by coupling onto the target anatomy 1300. Angling the working channel 700 up the spine can help prevent nerve or spinal damage. As previously described, placement of the working channel 700 can help protect surrounding bones and tissue. In some embodiments, the instrument shuttle 310 may have markings 312 on the length to indicate position of the working channel 700. In some embodiments, the markings 312 may provide a gauge to indicate a depth of an incision. In some embodiments, the markings 312 may provide a gauge to indicate how far the instrument shuttle 310 and/or working channel 700 have advanced into an incision. In some embodiments, different working channels 700 having different dimensions (diameter, length, etc.) can be provided for use within incisions of different sizes (e.g., depths). In some embodiments, the markings 312 can provide an indication of the depth of an incision, and a user may use this information to select a working channel 700 having an appropriate size (e.g., length). In some embodiments, the guard 300 may include markings 312 having any of the same or similar features and/or functions as the markings 312 of the instrument shuttle 310.

Figure 18A:
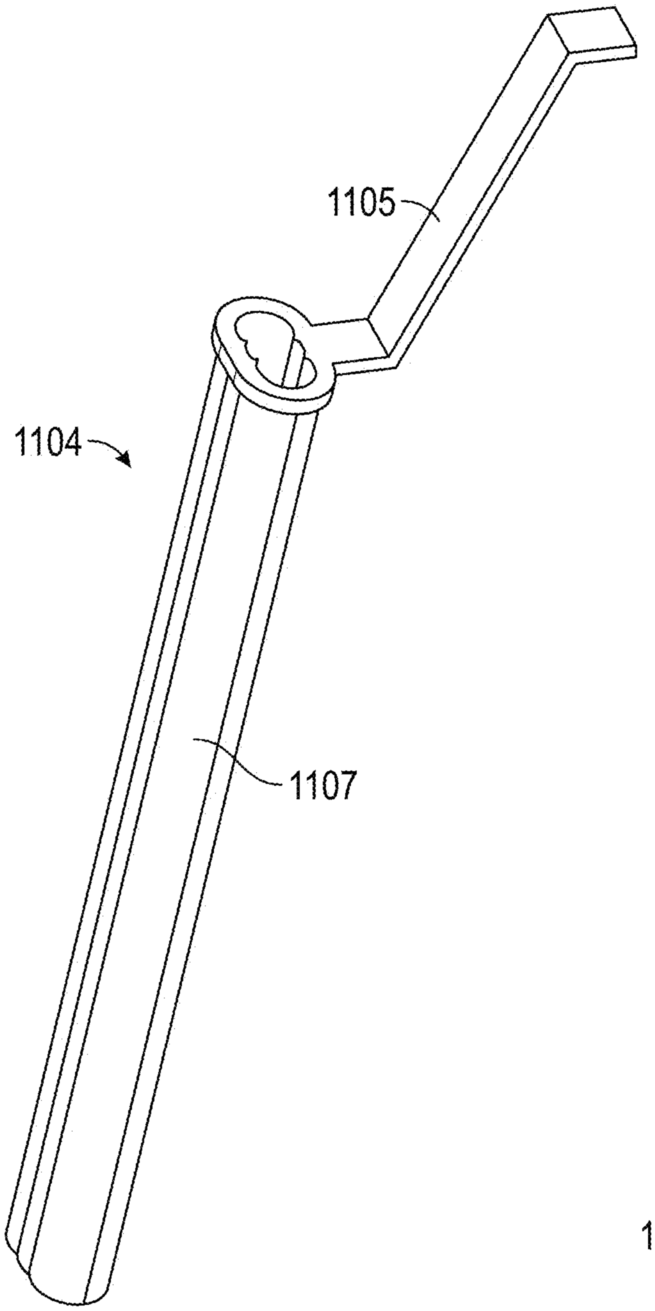
FIG. 18A depicts a perspective view of an embodiment of a guide.

FIG. 18A illustrates an embodiment of a channel divider or guide 1104. The guide 1104 can be used with the working channel 700 to provide one or more narrower channels for advancing instruments to the target area, as described further herein. In some embodiments, the guide 1104 can include a body 1107 defining one or more channels for advancing instruments to the target area.

Figure 18B:
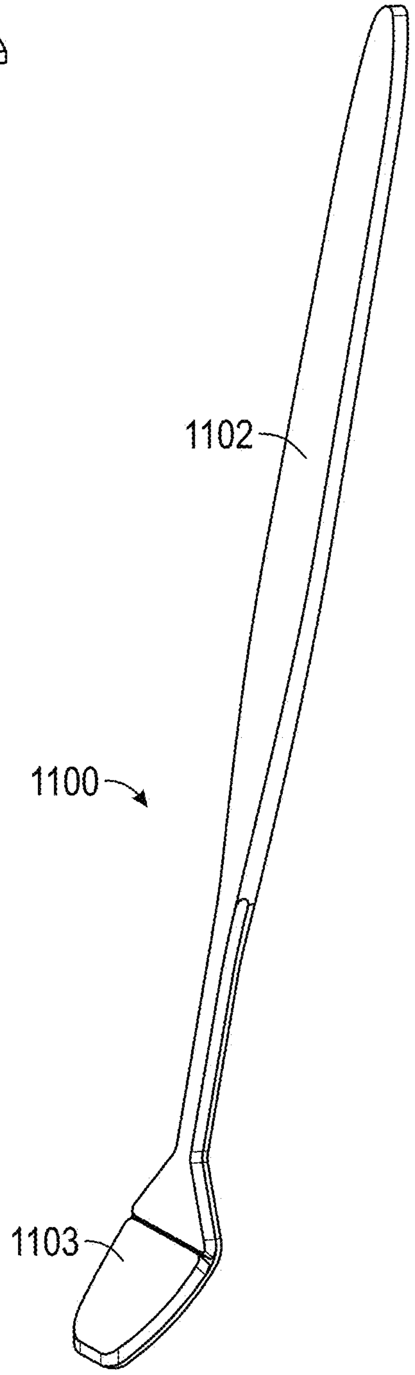
FIG. 18B depicts a perspective view of an embodiment of a guard.

FIG. 18B illustrates an embodiment of a guard 1100. The guard 1100 can include a guard plate 1103. The guard plate 1103 can include any of the same or similar features and/or functions as the guard plate 305 and vice versa. In contrast to certain embodiments of the guard 300, the guard 1100 is not part of an instrument shuttle for coupling to and advancing additional instruments, such as the working channel 700. Instead, in certain embodiments, the guard 1100 can be a separate instrument that can be advanced through the working channel 700. In some embodiments, when the target area is a lamina, a separate guard 1100 may be beneficial for traversing to the lamina when approaching the lamina along a path parallel or generally parallel to the lamina as shown, for example, in FIGS. 18C and 18D.

In some embodiments, the guard 1100 may have an elongated handle 1102. The elongated handle 1102 can be manipulated to maneuver the guard 1100 through muscle and other tissue.

At the distal end of the handle 1102, the guard plate 1103 may extend at a fixed angle form the handle. The fixed angle may be 15 degrees, 30 degrees, 45 degrees, 60 degrees, 75 degrees, 90 degrees, less than 15 degrees, between 0 degrees and 30 degrees, between 15 degrees and 30 degrees, between 30 degrees and 45 degrees, between 45 degrees and 60 degrees, between 60 degrees and 75 degrees, between 75 degrees and 90 degrees, between 15 degrees and 90 degrees, between 30 degrees and 60 degrees, between 60 degrees and 90 degrees, between 45 degrees and 90 degrees, or any other suitable angle. In other embodiments, the guard plate 1103 may extend generally parallel to the handle 1102. Shallow angles (e.g., parallel to the handle 1102, less than 15 degrees, or less than 30 degrees) may be beneficial when approaching parallel to or generally parallel to the lamina or target anatomy, which may be a precise and tight space. In certain embodiments, the guard plate 1103 may be pivotable (e.g., pivotably coupled to the handle 1102). In certain embodiments, the guard plate 1103 can be advanced below the inferior side of the lamina.

The guard 1100 and/or guard plate 1103 can be various shapes and sizes depending on the area needing to be protected. In some embodiments, the guard 1100 can help steady the working channel 700 acting as another point to engage with the target anatomy 1300.

Figure 18C:
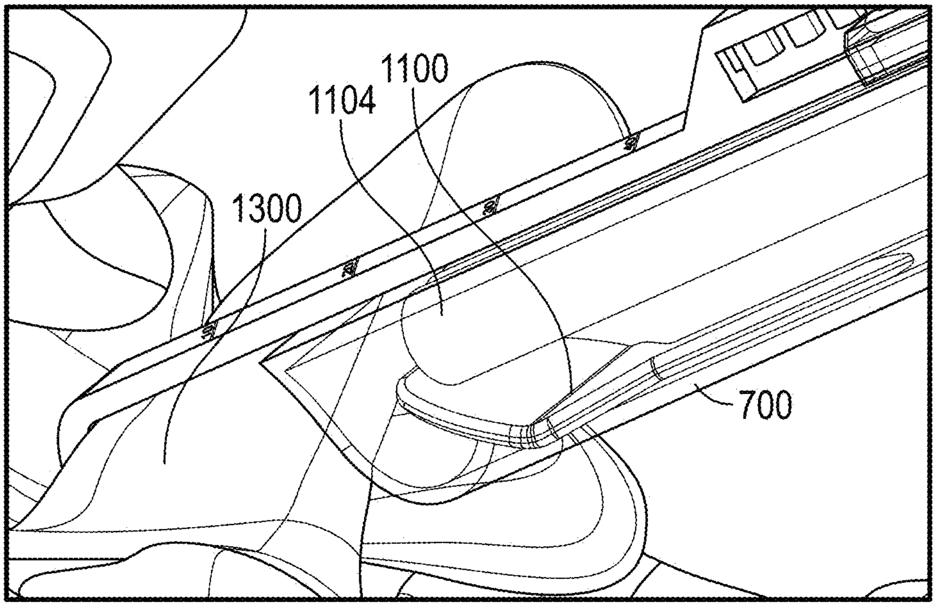
FIG. 18C depicts an example of the decompression system of FIG. 17A positioned adjacent to the target anatomy.
Figure 18D:
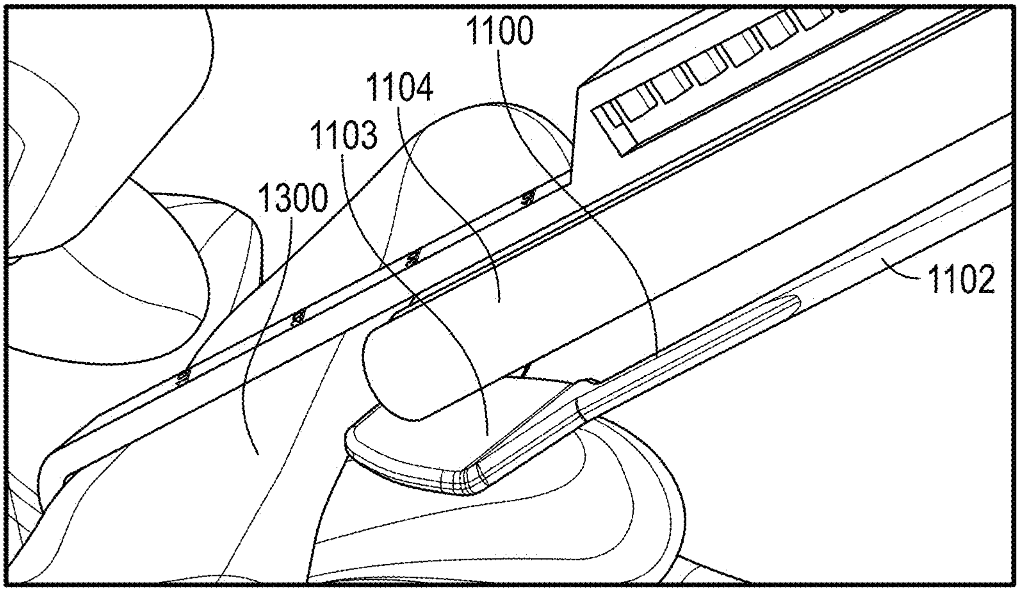
FIG. 18D depicts an example of the decompression system of FIG. 17A positioned adjacent to the target anatomy.

FIG. 18C illustrates the guide 1104 and guard 1100 within the working channel 700 adjacent the target anatomy 1300 with the working channel shown as transparent to show the interior of the working channel. FIG. 18D illustrates the guide 1104 and guard 1100 adjacent the target anatomy 1300 without showing the working channel 700. In some embodiments, once the working channel 700 is placed, the working channel 700 can be used to direct various instruments to the target anatomy 1300. For example, the guard 1100 can optionally be inserted into the working channel 700 and advanced to the target anatomy (e.g., to an underside of the target anatomy) to protect areas of the target anatomy 1300 or adjacent anatomical areas from unintentional damage, for example, as described with respect to the guard 300.

In some embodiments, the guide 1104 may be inserted into the working channel 700. The guide 1104 can be inserted into the working channel after the working channel 700 and hook 311 are positioned at the target anatomy. In some embodiments, the guide 1104 can be inserted into the working channel after the guard 1100 is positioned at the target anatomy. In other embodiments, the guard 1100 may be advanced down in the guide 1104. In some embodiments, the guard 1100 may be advanced outside of the guide 1104.

During a procedure, various tools may be delivered to the bone. The guide 1104 may be used to guide tools to a specific area of the target anatomy 1300. The guide 1104 may also protect surrounding tissue and bone from damage. In some embodiments, the guard 300 can be used to guide the guide 1104 through the working channel 700. In some embodiments, the guide 1104 may be used without the guard 1100.

Figure 19A:
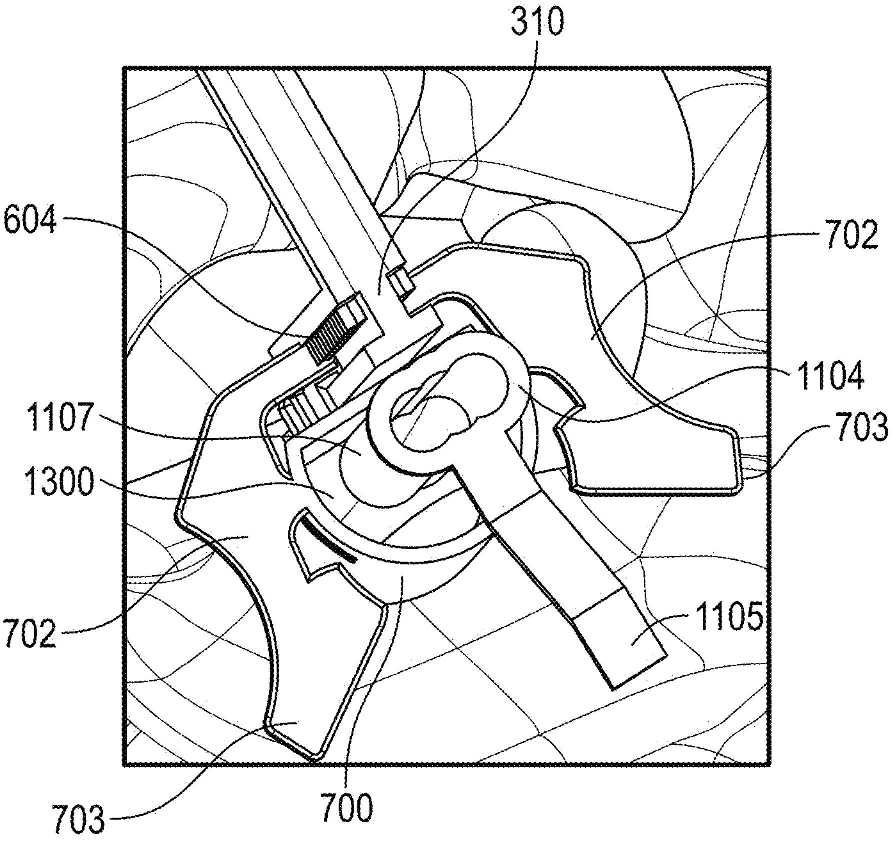
FIG. 19A depicts an example of the decompression system of FIG. 17A positioned adjacent to the target anatomy.
Figure 19B:
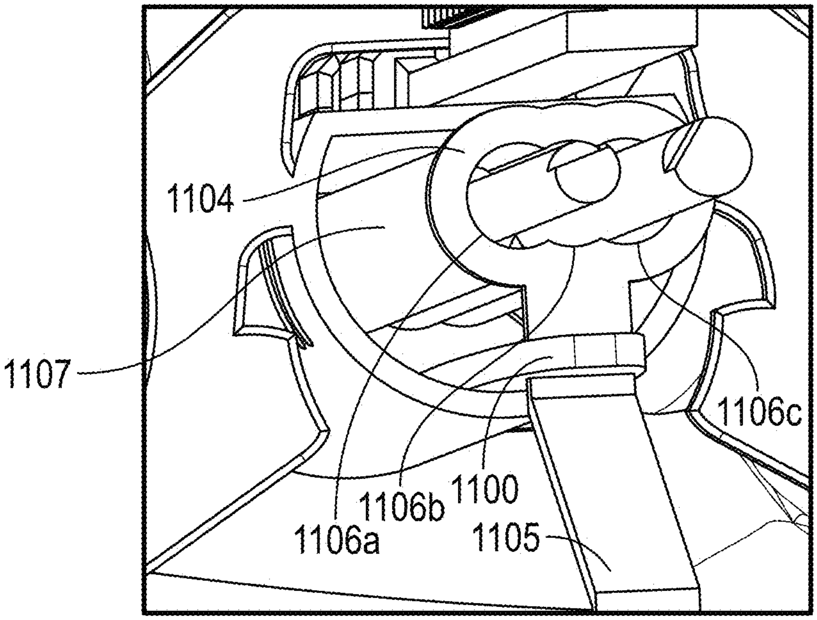
FIG. 19B depicts an example of the decompression system of FIG. 17A positioned adjacent to the target anatomy.

FIG. 19A illustrates a top view of the guide 1104 within the working channel 700 at the target anatomy 1300. The guide 1104 may have a handle 1105. The handle 1105 can prevent the guide 1104 from advancing too far into the working channel 700. The handle 1105 may also provide easier manipulation of the guide 1104 by the operator. In some embodiments, the handle 1105 of the guide 1104 may be used to couple to the guard 1100, as depicted in FIG. 19B. Coupling of components together can help keep the tools secured at the target anatomy 1300.

Referring to FIG. 19B, the guide 1104 is shown positioned within the working channel 700 with the guard 1100. In some embodiments, the guide 1104 may have one or more channels or barrels to accommodate various instruments and tools. In embodiments in which the guide 1104 includes multiple channels, the guide 1104 may also be referred to as a multi-channel or multi-barrel guide. In some embodiments, guide 1104 may have one, two, three, or more channels. Multiple channels may allow for a more precise trajectory of a tool advanced along one of the channels to different locations within the target anatomy 1300. In some embodiments, multiple channels may have different dimensions and/or shapes to accommodate different tools. In some embodiments, multiple channels may allow for the advancement of multiple tools simultaneously.

In some embodiments, the body 1107 of the guide 1104 may be shaped, sized, or otherwise configured to define three channels, 1106*a*, 1106*b*, and 1106*c*. In some embodiments, each of the channels 1106*a-c* in the guide 1104 may have a different shape and/or diameter to accommodate the shapes or dimensions of different tools. In some embodiments, the three channels may be all identically sized. The guide 1104 may be positioned within the working channel 700 such that channel 1106*a* is lined up with the target anatomy 1300. Similarly, channel 1106*b* or channel 1106*c* may be lined up with the target anatomy 1300.

FIG. 19B depicts the proximal ends of two instruments inserted into the guide 1104. As shown, a first instrument is positioned within the channel 1106*a* and a second instrument is positioned within the channel 1106*b*. While multiple instruments are shown within the guide 1104, in some embodiments, the guide 1104 may be used to advance a single instrument at one time via one of the channels 1106*a-c*. In some embodiments, the channels 1106*a-c* can allow a user to select a particular trajectory of a single instrument (e.g., by advancing the instrument down one of the channels). In some embodiments, a user may advance a single instrument down different channels 1106*a-c* at different times during a procedure. In some embodiments, a user may advance different instruments down different channels 1106*a-c* at different times during a procedure. In certain embodiments, use of a multi-channel guide 1104 may be beneficial in instances where the approach to the target anatomy requires a more precise trajectory, for example, if approaching the lamina along a path parallel or generally parallel to the lamina as shown, for example, in FIGS. 18C and 18D. In other embodiments, for example, when approaching perpendicular or generally perpendicular to the lamina as shown in FIG. 16, a working channel 700 may be used to advance instruments without using a guide 1104.

In some embodiments, multiple instruments can be positioned within two or more of the channels 1106*a-c* at the same time. In some embodiments, the channels 1106*a-c* can be used for advancement of multiple instruments simultaneously. Alternatively, a first instrument may be advanced through a first channel 1106*a-c* and a second instrument can be advanced through a second channel 1106*a-c* while the first instrument is still positioned in the first channel 1106*a*.

As described herein, the one or more instruments (e.g., a trephine, a drill, a kerrison, a burr, a reamer, etc.) can be advanced through the guide 1104 to drill or ream through the target anatomy (e.g., to create holes in the target anatomy). The instrument(s) may a create void and open up the canal. Once the holes are created, the instrument(s) may be removed from the guide 1104. In some embodiments, the guide 1104 may be a drill guide. In some embodiments, two or more of the channels 1106*a-c* can be used to create pilot holes to collectively make a larger opening in the target anatomy.

After the instrument(s) are removed from the guide 1104, the guide 1104 may be removed from the working channel

700. After removal of the guide 1104 from the working channel 700 the surgical site can be visualized down the working channel 700, for example, using a light source, loupes, a microscope, and/or the naked eye to determine if adequate decompression was performed. In some embodiments, a light source, loupes, and/or a microscope may be coupled to a portion of the decompression system 351, such as the lip 802 of the working channel 700. The light source, loupes, and/or microscope may be part of a decompression system, such as decompression system 350 or decompression system 351. In some embodiments, visualization of the surgical site can be performed with the guide 1104 still in place. In some embodiments, a pituitary or rongeur may be used to determine if more bone needs to be decompressed. In some embodiments, if it is determined that more decompression should be performed, additional drilling or reaming can be performed (e.g., through the working channel 700 and/or guide 1104).

In some embodiments, one or more instruments for performing a decompression procedure, such as a trephine, drill, kerrison, burr, reamer or other instrument to cut or alter the target anatomy, may be advanced through the working channel 700 to the target area 1300 without the guide 1104.

Although the guide 1104 is shown within the decompression system 351, in other embodiments, the guide 1104 may as be used within the decompression system 350. The guide 1104 can be inserted and used with a working channel 700 coupled to a guard 300 as described herein.

Figure 20A:
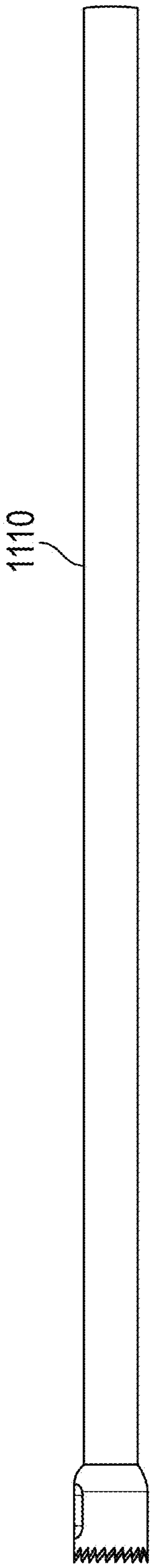
FIG. 20A depicts a side view of an embodiment of a trephine.
Figure 20B:
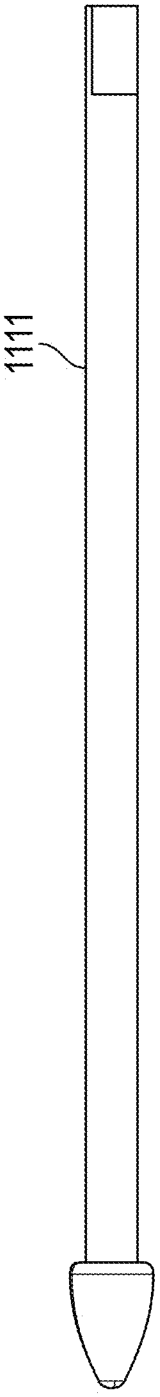
FIG. 20B depicts a side view of an embodiment of a drill burr.
Figure 20C:
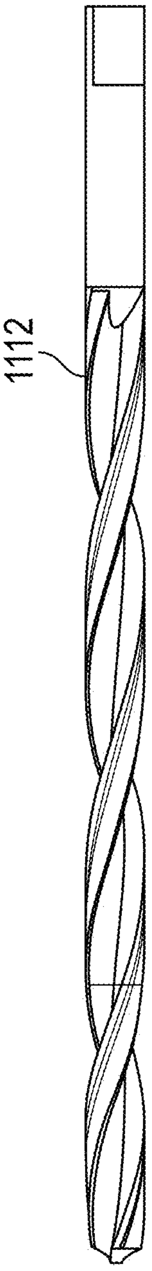
FIG. 20C depicts a side view of an embodiment of a drill bit.

FIGS. 20A-C depict embodiments of instruments that may be used with the guide 1104 and/or working channel 700, either separately or simultaneously. In some embodiments, the instruments may be part of a decompression system 350 or decompression system 351. FIG. 20A depicts a trephine 1110. FIG. 20B depicts an embodiment of a drill burr 1111. FIG. 20C depicts an embodiment of a drill bit 1112. The instruments may be used to create holes in the target anatomy. The instruments may be sharp or dull and/or serrated to depending on physician needs and/or risk to the patient. Any of the tools previously described herein may be used in conjunction with the guide 1104, working channel 700, and/or guard 1100 as described. In some embodiments, several tools may be used in sequence to remove portions of the bone. For example, the surgeon can use a kerrison, drill, trephine 1110, drill burr 1111, drill 1112, reamer or other instrument to remove all or part of the lamina and open the canal. A trephine 1000 such as the one described in FIG. 10 can be used in combination with the working channel 700 and/or guide 1104. Any of the prior medical instruments or tools previously described herein may be used in combination with the working channel 700 and/or guide 1104.

Figure 21A:
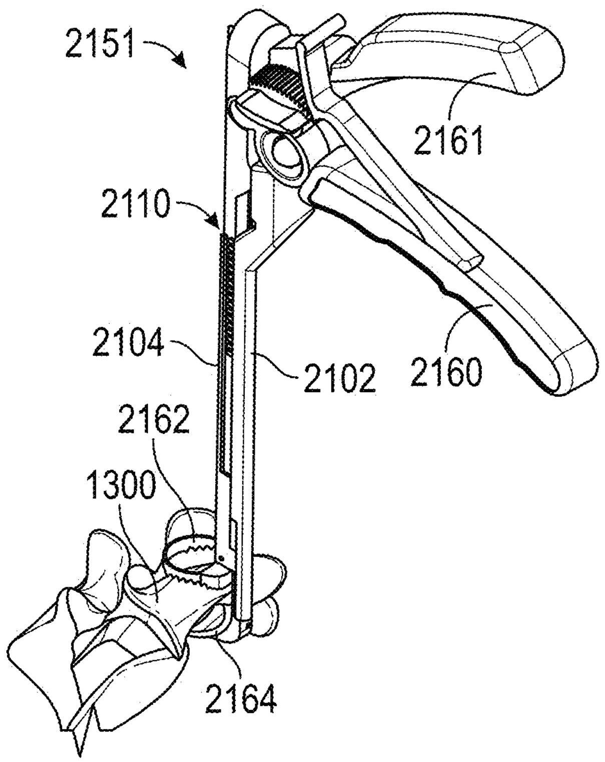
FIG. 21A depicts another embodiment of a guide system or decompression system positioned adjacent to the target anatomy in an unclamped state.
Figure 21B:
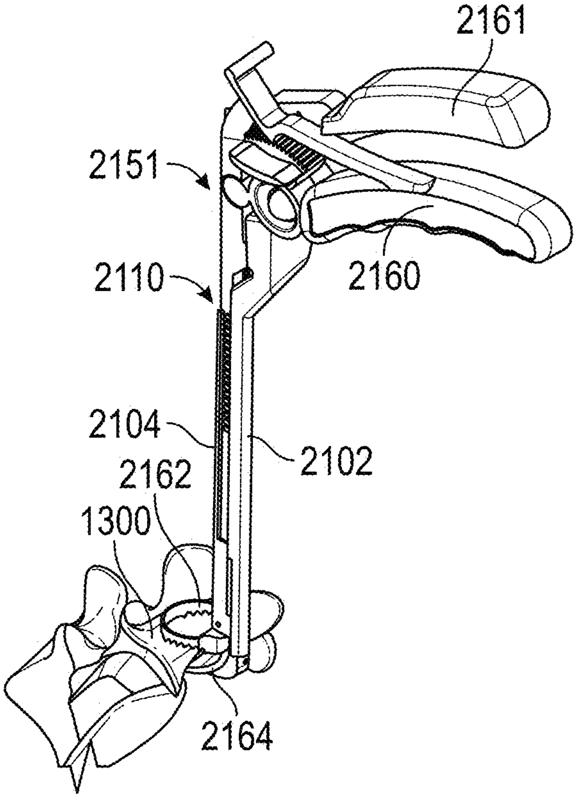
FIG. 21B depicts the embodiment of the guide system or decompression system of FIG. 21A positioned adjacent to the target anatomy in a clamped state.
Figure 21C:
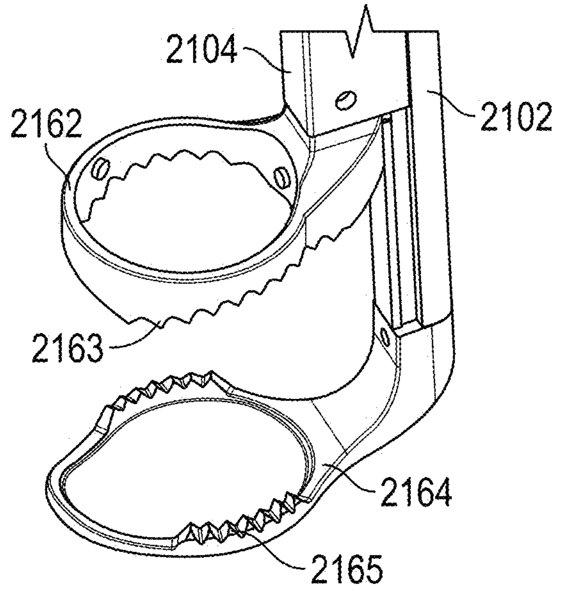
FIG. 21C depicts the embodiment of the upper clamp member and lower clamp member of the guide system or decompression system of FIG. 21A.

FIG. 21A depicts another embodiment of a guide system or decompression system 2151 positioned adjacent to the target anatomy 1300 in an unclamped state. FIG. 21B depicts the embodiment of the guide system or decompression system 2151 of FIG. 21A positioned adjacent to the target anatomy 1300 in a clamped state. FIG. 21C depicts the embodiment of the upper clamp member 2162 and lower clamp member 2164 of the guide system or decompression system 2151 of FIG. 21A.

As shown in FIG. 21A, in some implementations, the decompression system 2151 can include an instrument shuttle 2110. The instrument shuttle 2110 can include features, such as a track 2104, for coupling to additional instruments (such as a working channel) and advancing the additional instruments to the target area. For example, the instrument shuttle 2110 may include a track 2104.

The decompression system 2151 can include an upper clamp member 2162 and a lower clamp member 2164. The lower clamp member 2164 may be a guard plate. The upper clamp member 2162 may have one or more surface features 2163. The surface features 2163 may be protrusions or teeth to prevent slipping when positioned against bone. In some embodiments, the surface features 2163 can be rough, abrasive, or otherwise textured surfaces to prevent slipping when positioned against the bone. In some embodiments, the surface features 2163 may be a non-slip material. The lower clamp member 2164 may include surface features 2165. The surface features 2165 of the lower clamp member 2164 may be similar to the surface features 2163 of the upper clamp member 2162.

The upper clamp member 2162 can have a central aperture. For example, the upper clamp member 2162 can be a ring. The upper clamp member 2162 may be elliptical, circular, ovoid, rectangular, square, triangular, or another shape. The upper clamp member 2162 may be an outer bound defining a central aperture.

The upper clamp member 2162 can be fixed to the bottom end of the track 2104. The lower clamp member 2164 can be fixed to the bottom end of the arm 2102. In some implementations, the upper clamp member 2162 and the lower clamp member 2164 can be substantially parallel. The upper clamp member 2162 and the lower clamp member 2164 can be substantially orthogonal to the arm 2102 and/or the track 2104.

The decompression system 2151 can include a trigger 2160. The trigger 2160 can be actuated to shift the decompression system 2151 between a clamped state and an unclamped state. The track 2104 can be movable with respect to the arm 2102. For example, the track 2104 can slide along the arm 2102. Actuating the trigger 2160 can move the track 2104 with respect to the arm 2102. In a clamped state, the target anatomy 1300 (for example the lamina) can be clamped between the surface features 2163 of the upper clamp member 2162 and the surface features 2165 of the lower clamp member 2164. Actuating the trigger 2160 can cause the upper clamp member 2162 to move toward the lower clamp member 2164.

A user can position the lower clamp member 2164, or guard plate, beneath the target anatomy 1300, such that the upper clamp member 2162 is above the target anatomy 1300. The user can actuate the trigger 2160 by moving the trigger 2160 toward or away from the handle 2161. The user can actuate the trigger 2160 by compressing or releasing the trigger 2160 and the handle 2161. The user can move the trigger 2160 toward the handle 2161 to compress the upper clamp member 2162 and lower clamp member 2164 around the target anatomy 1300. While a trigger 2160 is shown in FIGS. 21A-21B, in some embodiments, other actuators may be used to shift the decompression system 2151 between the clamped state and unclamped state.

FIGS. 22A-D depict an embodiment of a working channel 2200 being positioned along the guide system or decompression system 2151 of FIG. 21A.

Figure 22B:
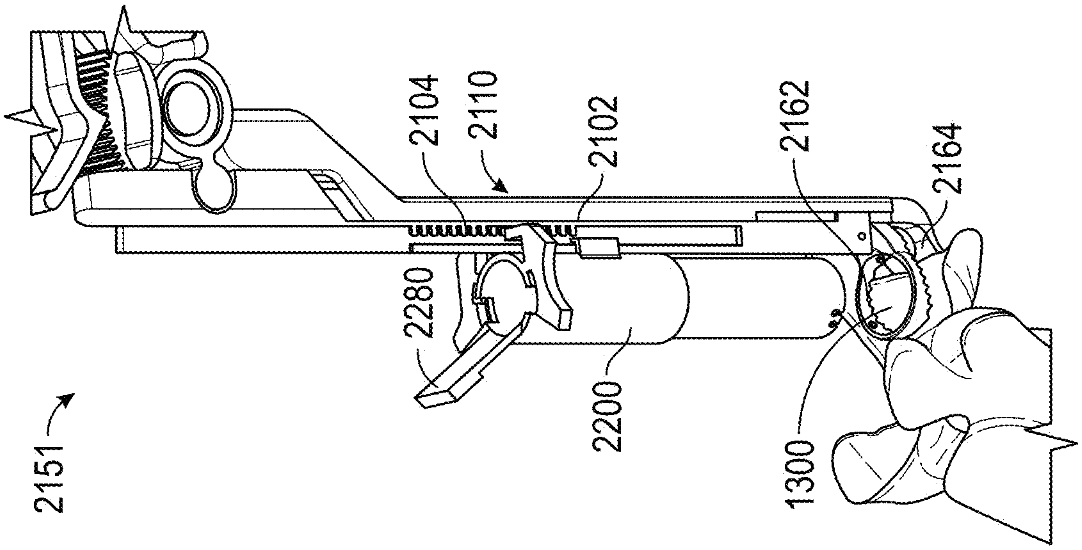
FIGS. 22A-22D depict an embodiment of a working channel being positioned along the guide system or decompression system of FIG. 21A.
Figure 22A:
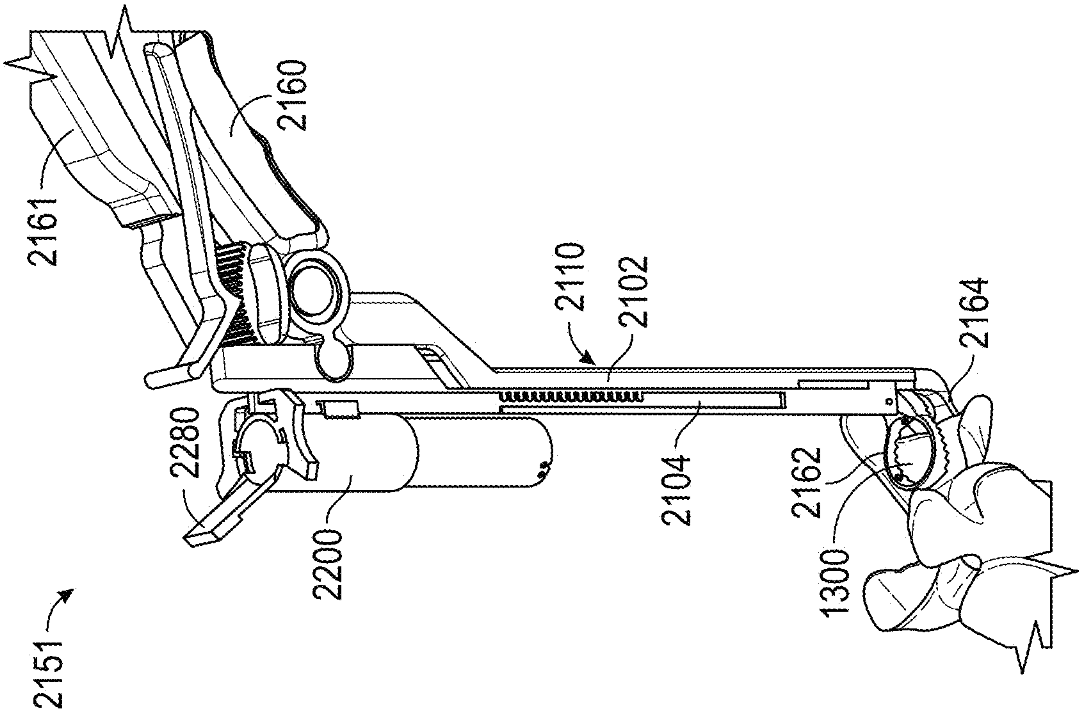
Figure 22C:
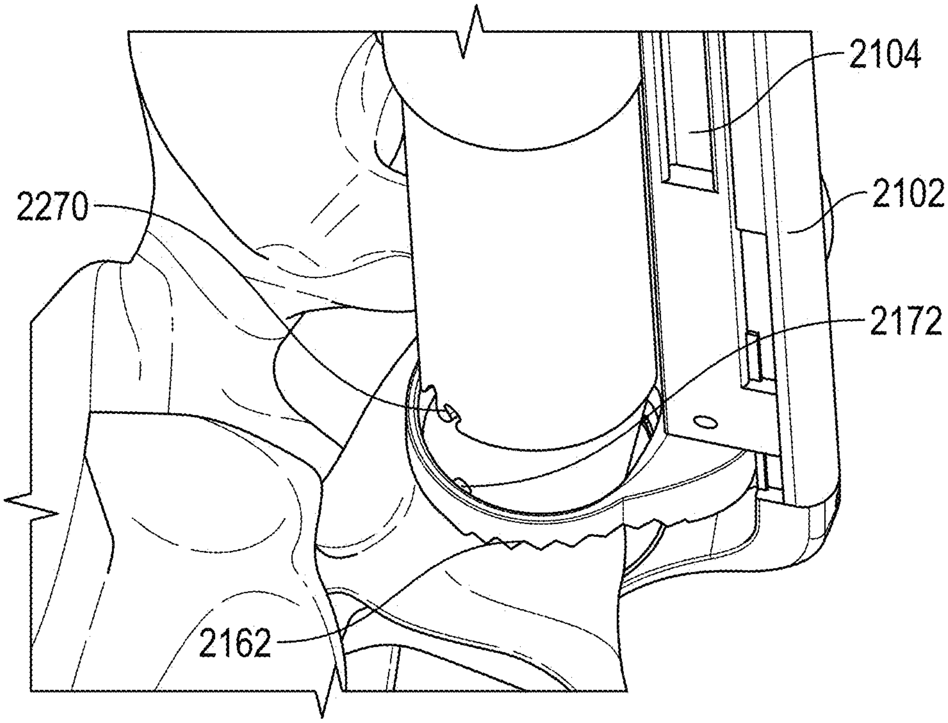
Figure 22D:
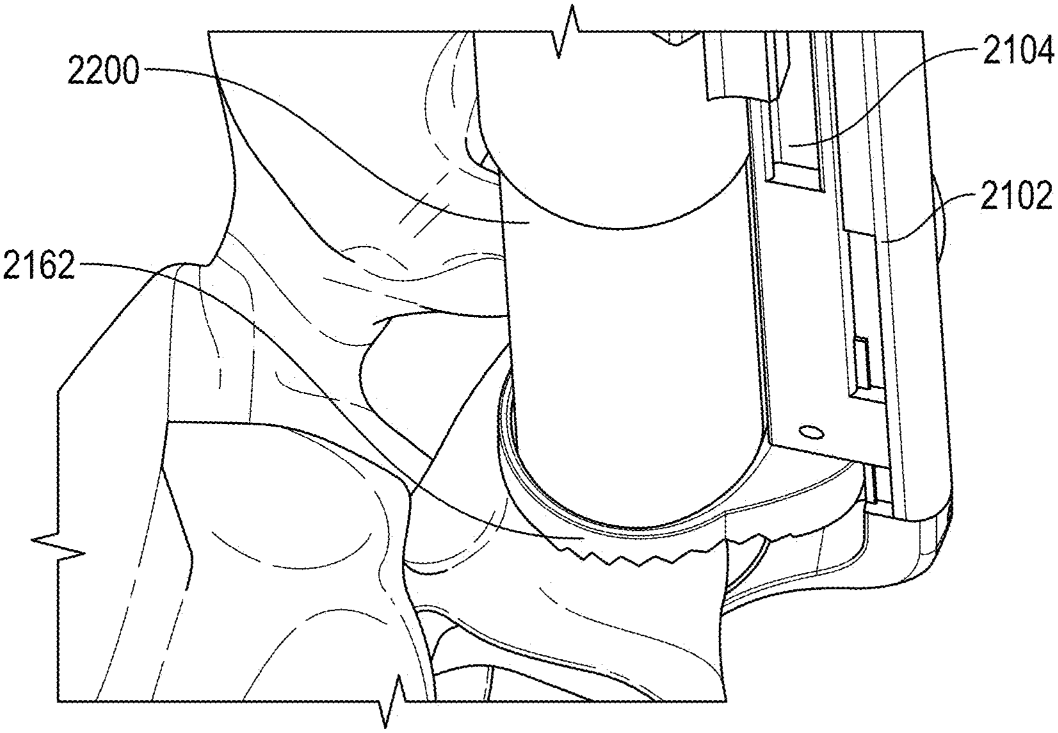

The working channel 2200 can slide along the track 2104 of the decompression system 2151. As shown in FIG. 22A, the working channel 2200 can be positioned on the top end of the track 2104. As shown in FIG. 22B, the working channel 2200 can advance (e.g., slide) down to the middle of the track 2104. As shown in FIG. 22C, the working channel 2200 can advance (e.g., slide) further toward the upper clamp member 2162. An aperture 2270 of the working channel 2200 may be aligned with a protrusion 2172 of the upper clamp member 2162. As shown in FIG. 22D, the working channel 2200 can advance (e.g., slide) down such that it locks in place with respect to the upper clamp member 2162. The protrusion 2172 of the upper clamp member 2162 can lock into the aperture 2270 of the working channel 2200. In some embodiments, the working channel 2200 may include a plurality of apertures 2770 and the upper clamp member 2162 can include a plurality of protrusions 2172. In some embodiments, the working channel 2200 can include one or more protrusions and the upper clamp member 2162 can include one or more apertures. In some embodiments, alternative complementary coupling structures may be provided on the upper clamp member 2162 and working channel 2200.

Once the working channel 2200 is secured to the upper clamp member 2162, the working channel 2200 can provide a clear path to the target anatomy 1300 for a decompression procedure and/or provide further protection of the surrounding anatomy. In certain embodiments, the lower clamp member 2164, or guard plate, may act as an engagement feature for engaging with or securing to the target anatomy to provide a stable and consistent path towards the target anatomy for instruments advancing along the track 2104. Advantageously, the upper clamp member 2162 can provide further stability to the working channel 2200 due to the surface features 2163. In some embodiments, a user can more easily maneuver the decompression system 2151 without the working channel 2200, only clamping the target anatomy 1300 using the upper clamp member 2162 and lower clamp member 2164. Then, the user can position the working channel 2200 once the decompression system 2151 has already been positioned with respect to target anatomy 1300.

Figure 24A:
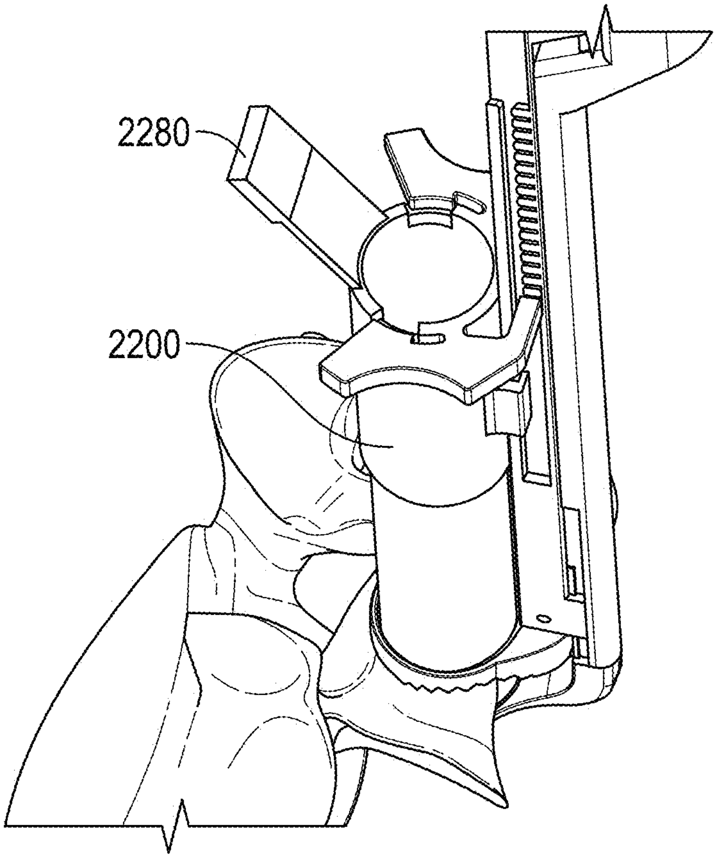
FIGS. 24A and 24B show an example of a wing on the working channel of FIG. 22A.
Figure 24B:
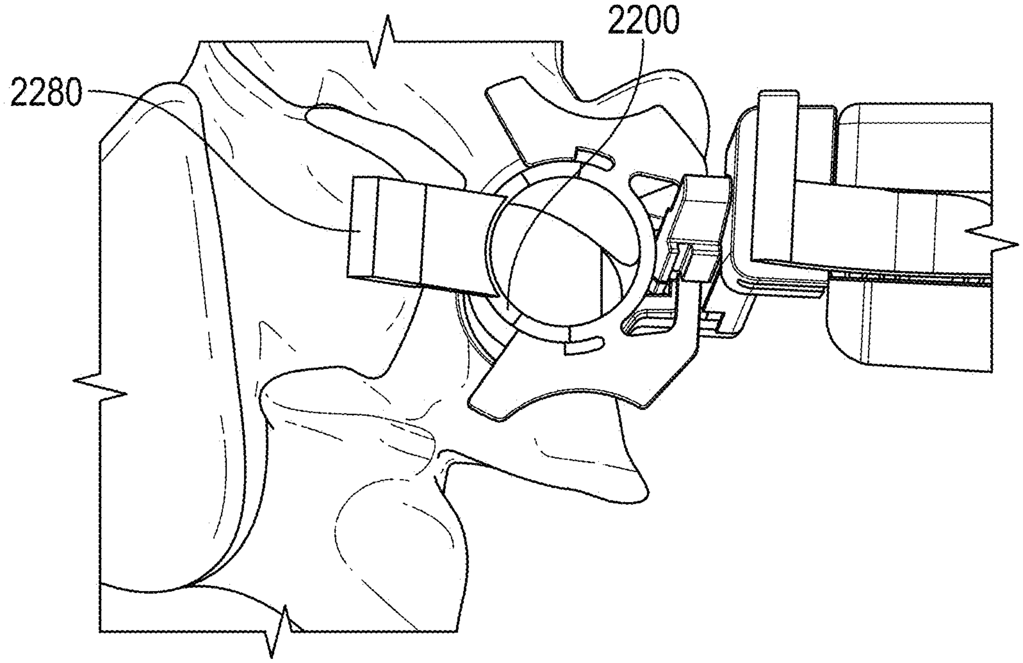

The working channel 2200 may include a wing 2280 as described with respect to FIGS. 24A-B.

FIGS. 23A-D show an example of using a tissue probe or ligament probe 2300 to position the decompression system 2151 of FIG. 21A adjacent to the target anatomy 1300. The ligament probe 2300 can include a hook 2311. The hook 2311 may be advantageous in procedures approaching inferior to the lamina. The hook 2311 may be various sizes to easily couple to different sized or shaped bones. The hook 2311 can engage with and/or secure to the target area or anatomy adjacent the target area. The ligament probe 2300 may guide the decompression system 2151 to provide a stable and consistent path to the target area. The hook 2311 may help guide the lower clamp member 2164, or guard plate, to a position beneath the target anatomy 1300 or lamina.

Figure 23B:
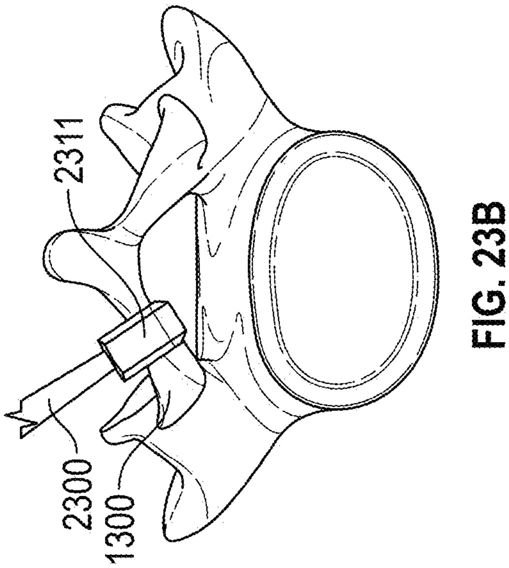
FIGS. 23A-23D show an example of using a tissue probe or ligament probe to position the decompression system of FIG. 21A adjacent to the target anatomy.
Figure 23D:
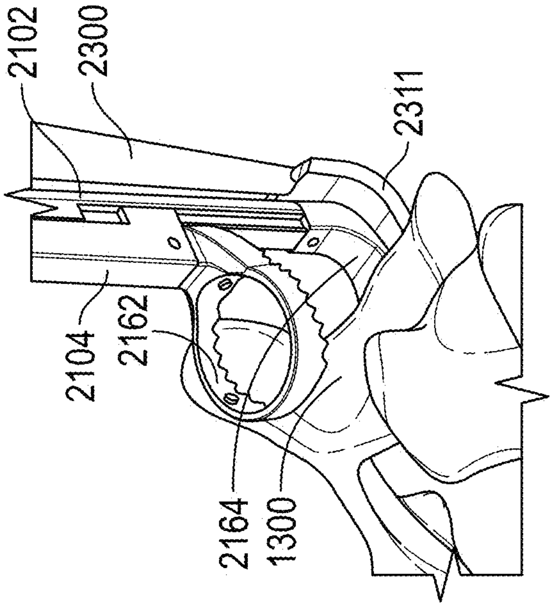
Figure 23A:
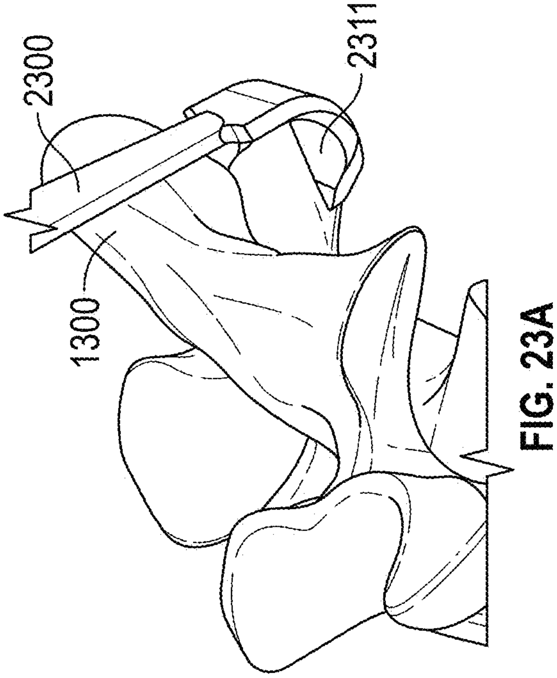

As shown in FIGS. 23A and 23B, the ligament probe 2300 can be positioned such that the hook 2311 is beneath the target anatomy 1300. The hook 2311 may move tissue from the area around the target anatomy 1300 to provide space for the decompression system 2151.

Figure 23C:
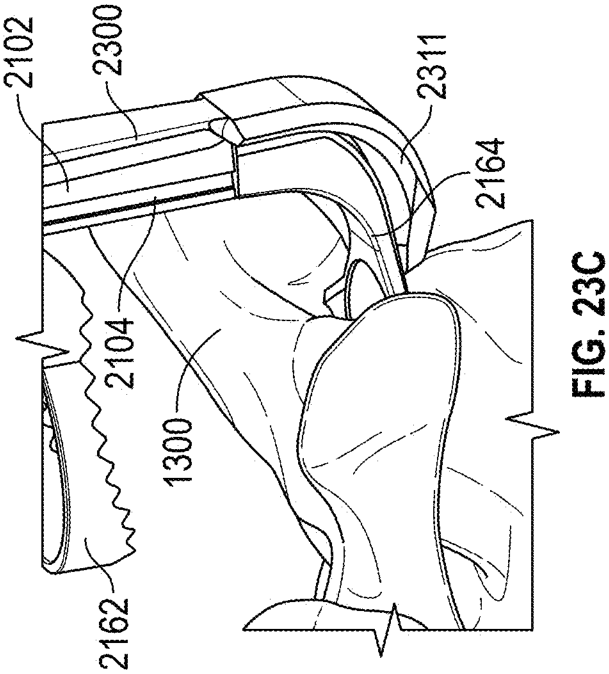

As shown in FIGS. 23C and 23D, the decompression system 2151 may be positioned such that the lower clamp member 2164 is above the hook 2311. For example, the lower clamp member 2164 may be positioned between the hook 2311 and the target anatomy 1300. The arm 2102 may be positioned adjacent to the ligament probe 2300.

FIGS. 24A and 24B show an example of a wing 2280 on the working channel 2200 of FIG. 22A.

The wing 2280, or back wing, can extend from the top of the channel 2200. A light source can be positioned on the wing 2280. Advantageously, mounting a light source on the wing 2280 can allow the lumen of the working channel 2200 to be lit. This can improve visibility in the working channel 2200 for a user.

Figure 25B:
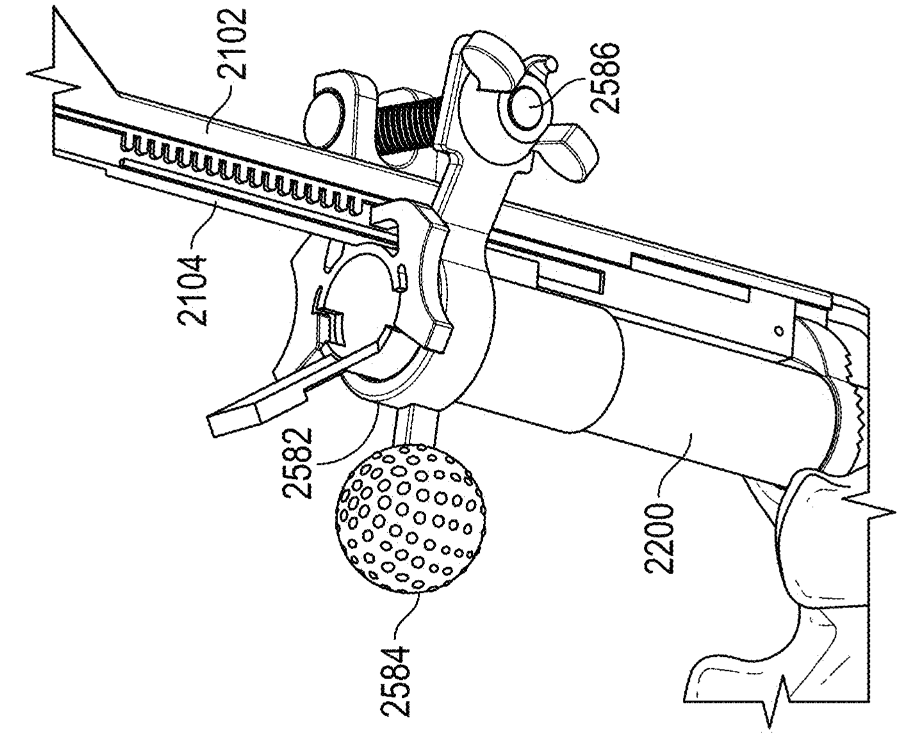
FIGS. 25A and 25B show an example of a skin stop clip positioned around the working channel of FIG. 22A.
Figure 25A:
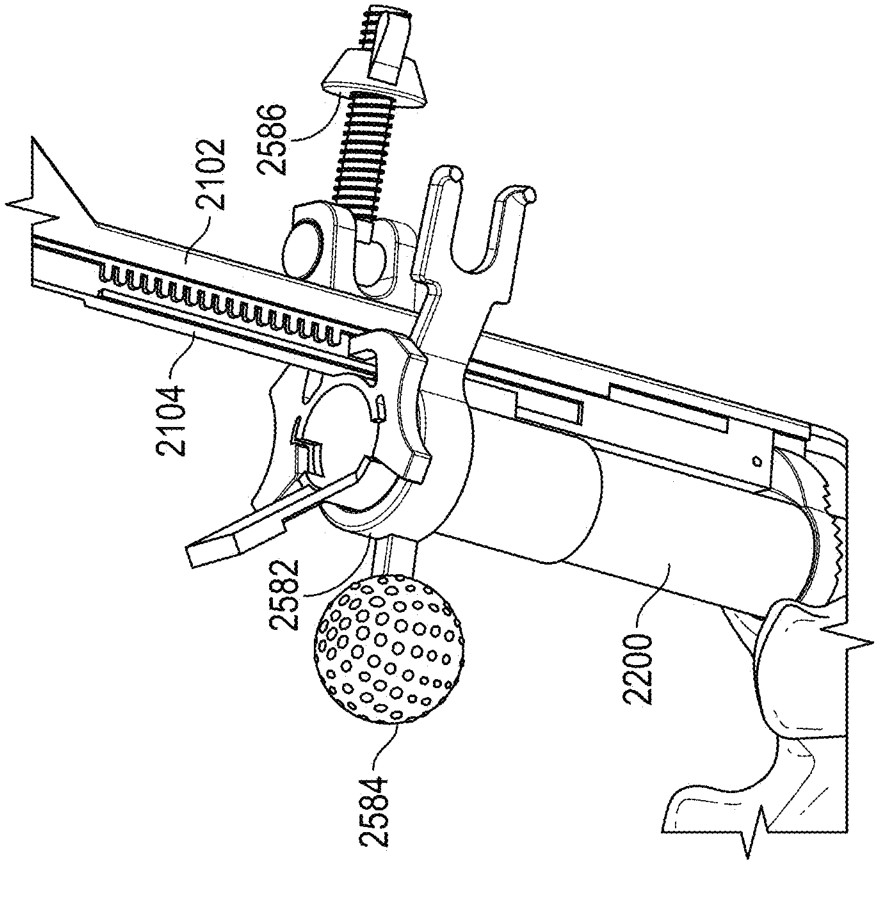
Figure 25D:
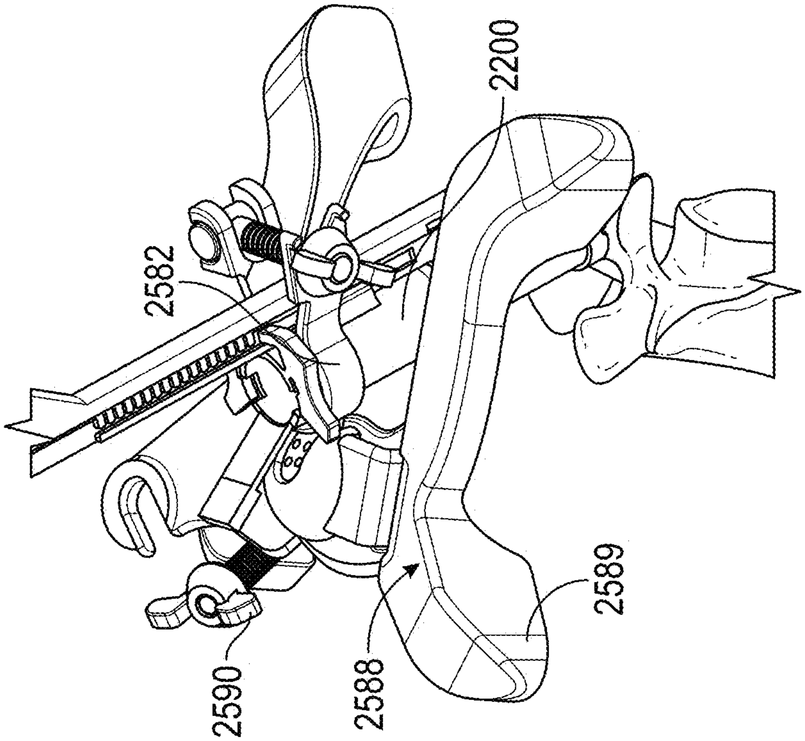
FIGS. 25C and 25D show an example of a skin stop positioned around the working channel of FIG. 22A.
Figure 25C:
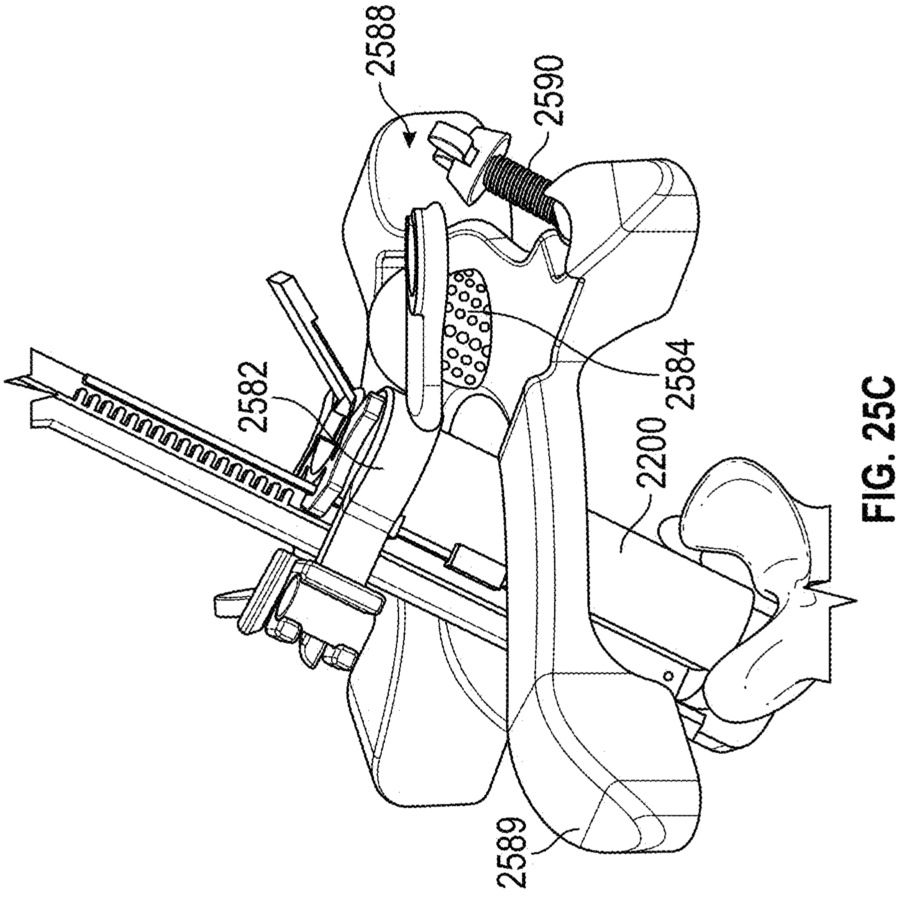
Figure 25F:
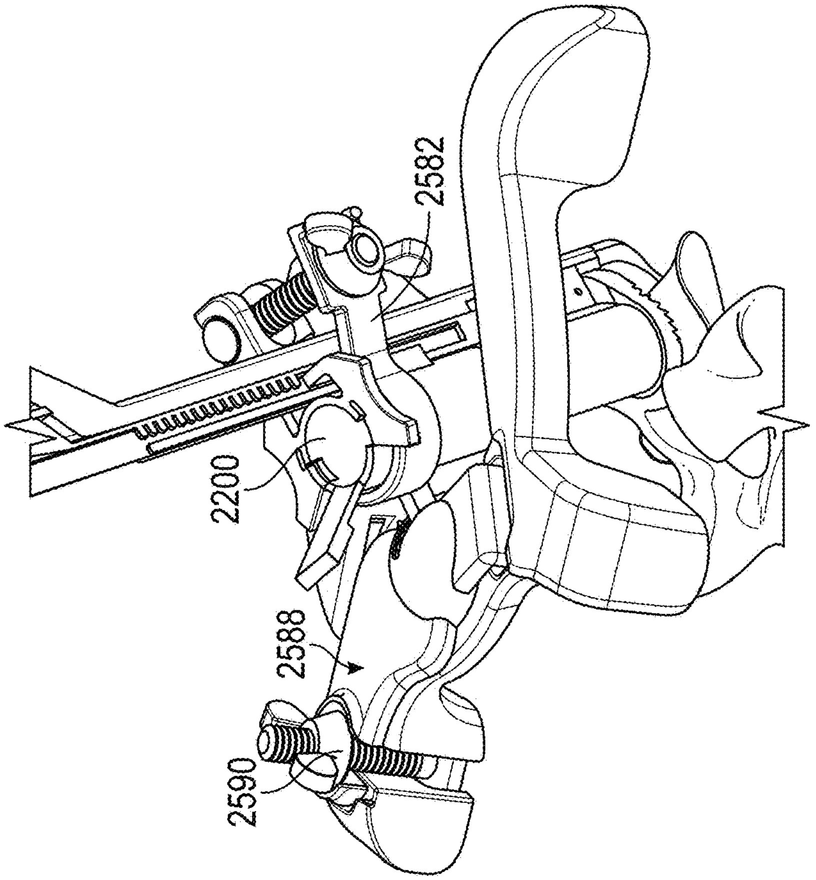
FIGS. 25E and 25F show an example of a rear wing nut securing the skin stop in place around the working channel of FIG. 22A.
Figure 25E:
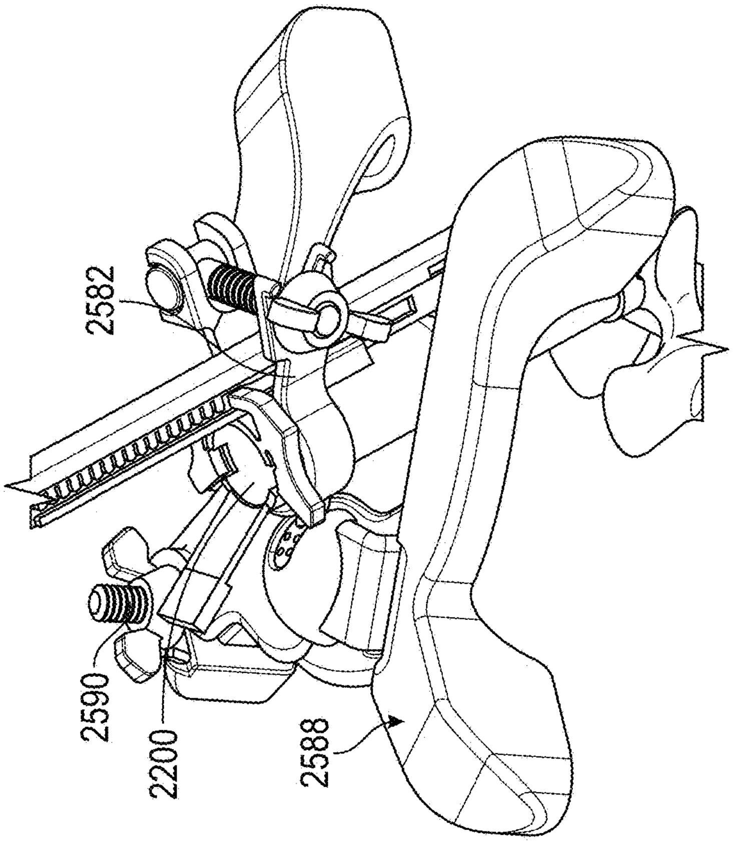

FIGS. 25A and 25B show an example of a skin stop clip 2582 positioned around the working channel 2200 of FIG. 22A. FIGS. 25C and 25D show an example of a skin stop 2588 positioned around the working channel 2200 of FIG. 22A. FIGS. 25E and 25F show an example of a rear wing nut 2590 securing the skin stop 2588 in place around the working channel 2200 of FIG. 22A.

The skin stop 2588 can be positioned on a patient's back to keep the decompression system 2151 and/or the working channel 2200 in a stable position relative to the patient. The skin stop 2588 can include a plurality of legs (e.g., four legs) 2589 that contact the back of the patient.

As shown in FIG. 25A, the skin stop clip 2582 can be positioned around the working channel 2200, the track 2104, and the arm 2102 of the decompression system 2151. As shown in FIG. 25B, the skin stop clip 2582 can be tightened with the wing nut 2586.

The skin stop clip 2582 can include a ball 2584. The ball 2584 can include bumps, indentations, grooves, and/or other surface features. As shown in FIG. 25C, the ball 2584 can form a ball joint with the skin stop 2588. The surface features of the ball 2584 can provide friction in the ball joint to allow the ball 2584 and a clamp of the skin stop clip 2582 to integrate and lock in place. The ball joint can allow locking in any position. The ball 2584 can be maneuvered to lock the skin stop 2588 in any position. The skin stop 2588 can include a rear wing nut 2590 for clamping down the ball joint and preventing further articulation of the instrument. As shown in FIGS. 25E and 25F, the rear wing nut 2590 can be tightened to lock the skin stop 2588 in place relative to the skin stop clip 2582.

FIGS. 26A-D show an example of a trephine 2600 used with the decompression system 2151 to core a hole in the target anatomy 1300.

The trephine 2600 may be a circular blade or saw. The proximal end of the trephine 2600 may include a handle 2692. The distal end of the trephine may include a serrated surface 2694. The trephine 2600 may be advanced through the working channel 2200 and the upper clamp member 2162. A user can advance and guide the trephine 2600 using the handle 2692. A user may rotate the handle 2692 to cut through the bone.

Figure 26B:
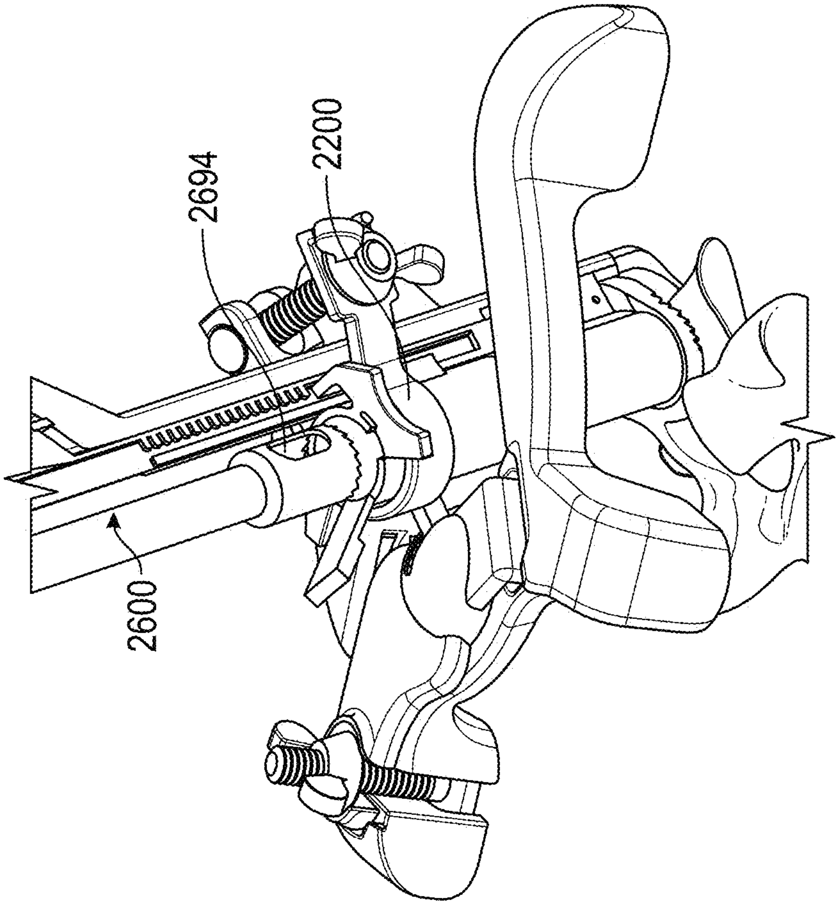
FIGS. 26A-26D show an example of a trephine used with the decompression system to core a hole in the target anatomy.
Figure 26A:
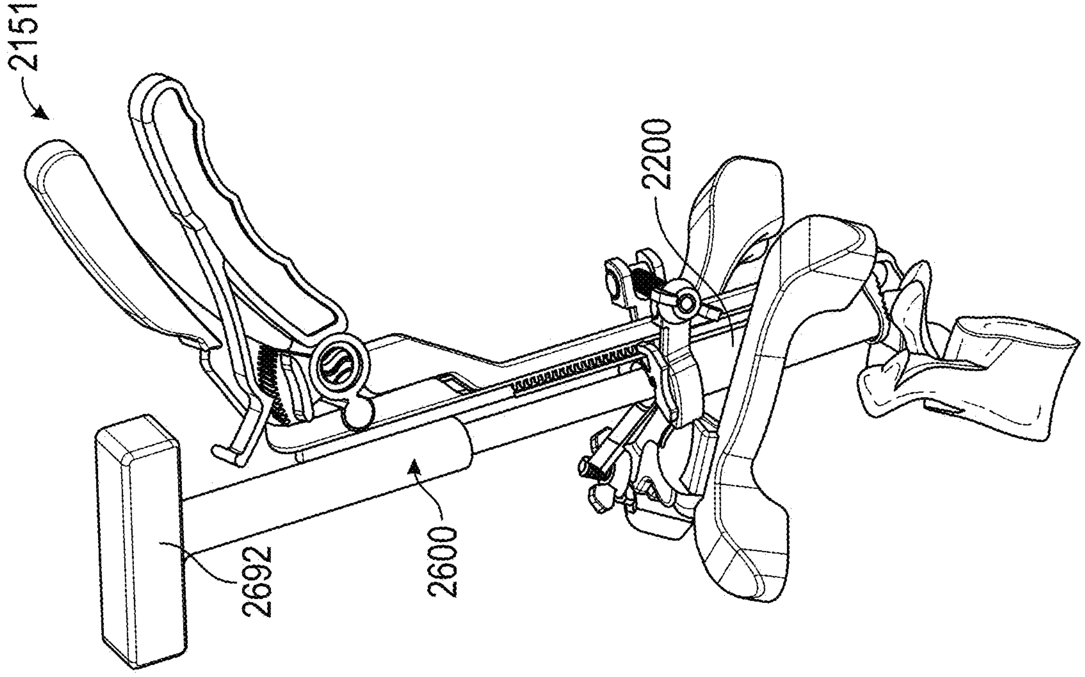
Figure 26C:
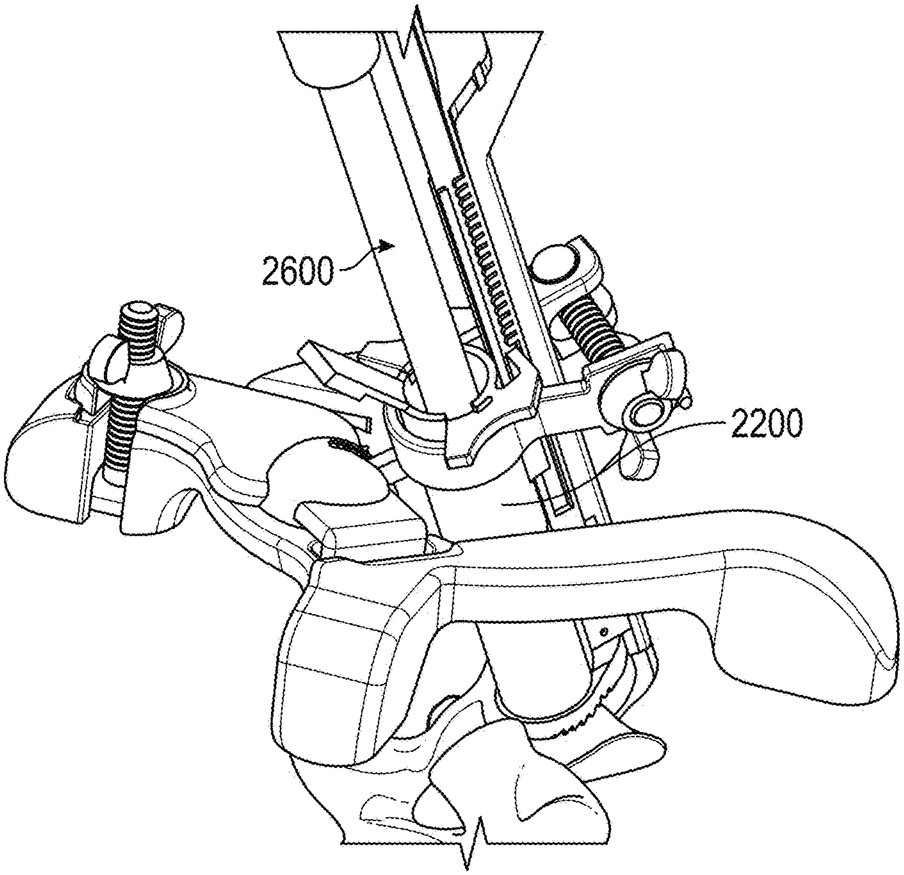
Figure 26D:
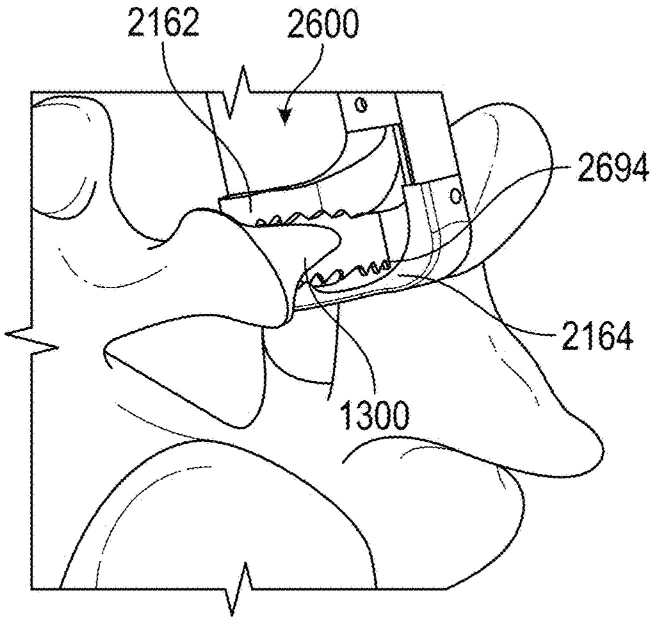

As shown in FIG. 26D, the serrated surface 2694 of the trephine 2600 can cut through bone. In some examples, the trephine 2600 can be used manually. In another example, the trephine 2600 can be power operated. The serrated surface 2694 of the trephine 2600 can stop when it contacts the lower clamp member 2164, or guard plate. Advantageously, the lower clamp member 2164 can prevent progression of the trephine 2600 into the spinal cord. The core of the bone can be removed through the working channel 2200. Once the core of the bone is removed, the trephine 2600 can be removed from the working channel 2200. The upper clamp member 2162 and lower clamp member 2164 can remain in place around the target anatomy 1300 after the core of the bone is removed. Advantageously, this can allow a user to access the tunnel in the bone through the working channel 2200 and/or the decompression system 2151.

Figure 27:
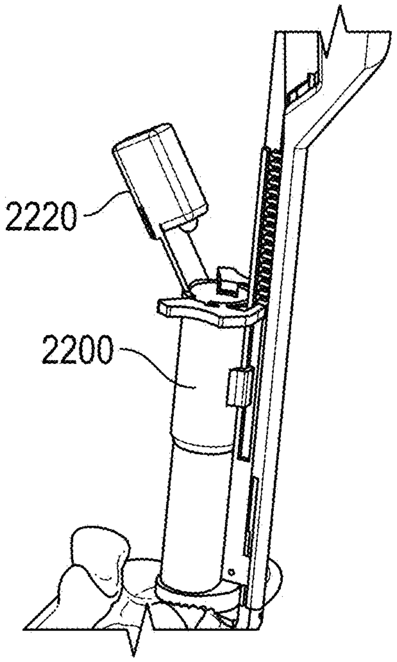
FIG. 27 depicts an embodiment of a light source coupled to the working channel.

FIG. 27 depicts an embodiment of a light source 2220 coupled to the working channel 2200. The light source 2220 may clip on to the working channel 2200 and may be referred to as a light clip. The light source 2220 may include a light-emitting diode (LED) light, a halogen light, or any other suitable light. The light source 2220 may be disposable. In some embodiments, the light source 2220 may include an internal power source so that additional wiring through the operating room is not needed to provide power to the light source 2220.

FIGS. 28A-28M, 29A-29C, 30A-30F, 31A-31C, and 32A-32B show embodiments of a system for laminectomy, laminotomy, or decompression. In some examples, the systems, methods, and devices described can be used to remove part of a lamina of the spine in order to relieve pressure on nerves of a patient. In some examples, any or all of the devices described with respect to FIGS. 28A-28M, 29A-29C, 30A-30F, 31A-31C, and 32A-32B can be provided in a kit. Any of the other devices described herein may be provided in the kit additionally or alternatively to any or all of the devices described with respect to FIGS. 28A-28M, 29A-29C, 30A-30F, 31A-31C, and 32A-32B. In some examples, any or all of the devices described herein can be entirely disposable. In some embodiments, the kit can be disposable. In some examples, the devices can be packaged in a plastic tray with a Tyvek lid which can be disposed after surgery. Advantageously, this can minimize the time and money spent as well as sterile risk to the patient. In some examples, the kit can be made of a surgical grade polymer. For example, the kit can be made of polycarbonate, ABS, IXEF, or other surgical grade materials. In some examples, the kit can be made of stainless steel and/or titanium. In some examples, the devices can be packaged in an autoclavable tray. The devices, or instruments, may be made of metal and autoclaved.

The systems and devices described herein can be used for an interlaminar approach where an incision is made to access the lamina and the interlaminar space. In certain embodiments, the systems and devices described herein can be advanced to the lamina via a inferior approach. In certain embodiments, the systems and devices described herein can be advanced towards an inferior portion of the lamina. For example, in some embodiments, the systems and devices can be advanced towards an inferior border or edge 1301 of the lamina, as shown for example, in FIGS. 35A, 35C, 35D, 36B, 37A, and 37C. The inferior edge 1301 is the edge of the lamina positioned between a posterior side or posterior surface 1305 (as shown, for example, in FIGS. 34A, 34D, and 35C) of the lamina and an anterior side or surface 1303 (as shown, for example, in FIGS. 33A and 35A) of the lamina. The posterior side or surface 1305 may also be referred to as the dorsal side or dorsal surface. The anterior side or surface 1303 may also be referred to as the ventral side or ventral surface. The systems and devices described herein may approach the lamina (e.g., the inferior edge 1301 from an inferior angle or inferior position. For example, the systems and devices described herein may approach the inferior edge 1301 from a position inferior to the inferior edge and advance superiorly towards the inferior edge. In some embodiments, the systems and devices describe herein may approach the lamina along or generally along an axis parallel with or generally parallel with a plane the bisects the inferior edge 1301 of the lamina between the anterior surface 1303 and the posterior surface 1305. In some embodiments, the systems and devices described herein may approach the inferior edge 1301 of the lamina at an angle from plus or minus 5°, plus or minus 10°, plus or minus 15°, or plus or minus 20° relative to a plane of that bisects the inferior edge 1301 of the lamina between the posterior surface 1305 and the anterior surface 1303, depending on a patient's anatomy or the surgical approach that is needed to complete the lamina removal or decompression. In some embodiments, the systems and devices described herein may approach the lamina along or generally along an axis parallel with a centerline or midline that extends through the inferior edge 1301 between the posterior surface 1305 and anterior surface 1303. In some examples, the systems and devices described herein can be advanced to the target anatomy along a path that is substantially in line or parallel with the lamina (e.g., parallel with a posterior surface 1305 or anterior surface 1303 of the lamina), or target anatomy 1300. An arrow 3507 is shown in FIGS. 35A and 35C depicting a direction of approach of the systems and devices described herein at from inferior angle.

Figure 28B:
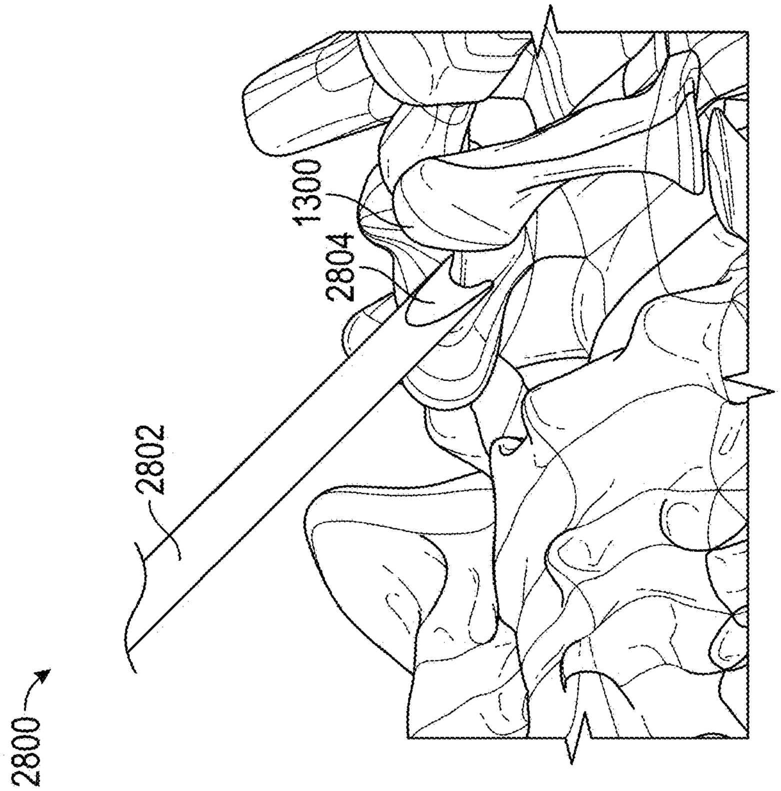
FIG. 28B shows a closer view of the embodiment of a laminar locator of FIG. 28A engaged with the target anatomy.
Figure 28A:
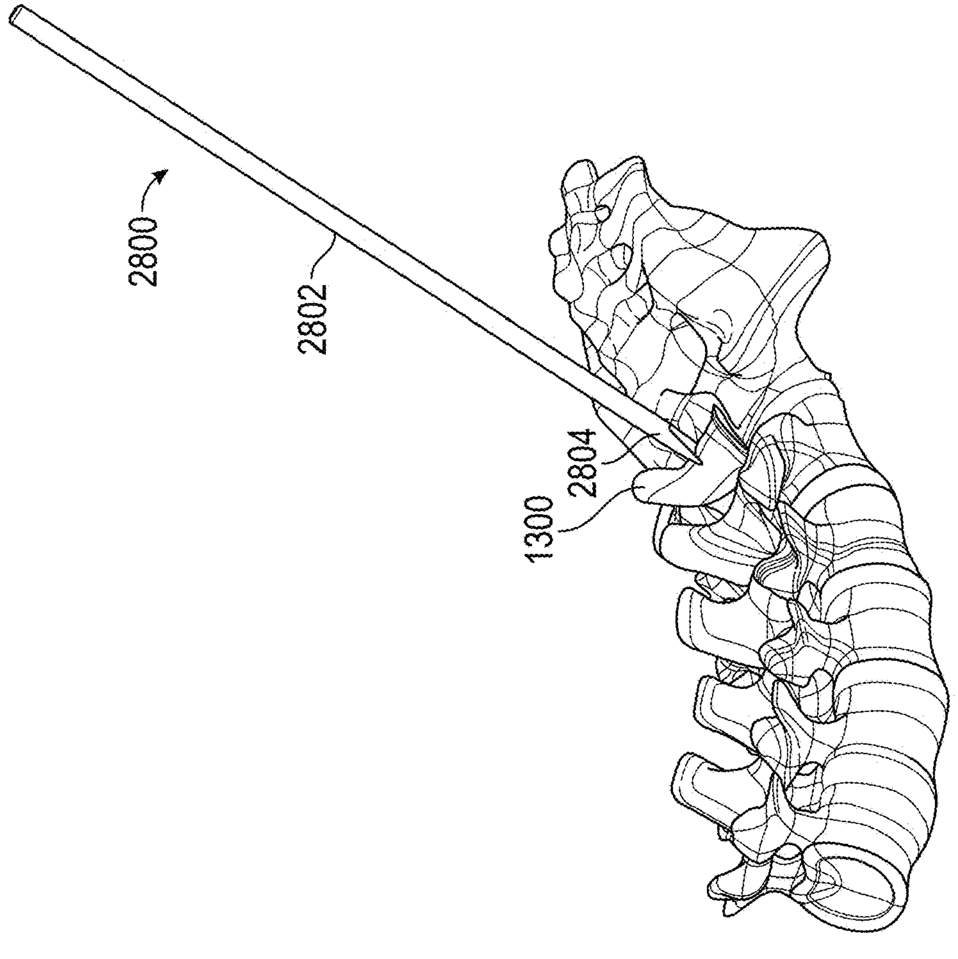
FIG. 28A shows an embodiment of a laminar locator engaged with a target anatomy.
Figure 28C:
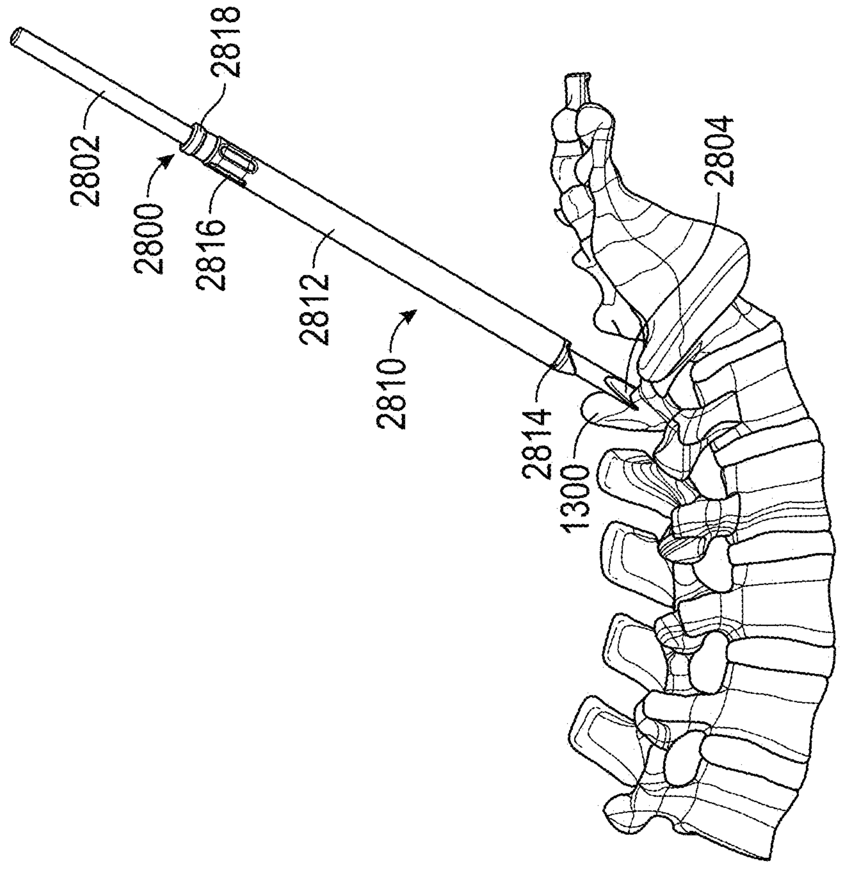
FIGS. 28C-28F show an example of a dilator positioned over the laminar locator of FIG. 28A.

In some embodiments, a system for laminectomy, laminotomy, or decompression can include a laminar finder or laminar locator. FIG. 28A shows an embodiment of a laminar locator 2800 engaged with a target anatomy 1300. FIG. 28B shows a closer view of the embodiment of a laminar locator 2800 of FIG. 28A engaged with the target anatomy 1300.

In some examples, the target anatomy 1300 can be a limina of the spine. In some embodiments, the laminar locator 2800 can be a rod. The laminar locator 2800 can include a shaft 2802. The laminar locator 2800 can be cannulated with a lumen throughout the shaft 2802 such that a guidewire can be delivered therethrough. In other embodiments, the laminar locator 2800 can be solid or lack a lumen. The distal end of the laminar locator 2800 can include a tip 2804 configured to be positioned in contact with the lamina. In some examples, the tip 2804 can be V-shaped or U-shaped, with two or more projections configured to be positioned on multiple sides of the lamina. For example, in some embodiments, one projection may engage a posterior side 1305 of the lamina and another projection may engage an anterior side 1303 of the lamina. In some embodiments, a recessed section between the projections may engage an inferior edge 1301 of the lamina. In some examples, the tip 2804 can be any shape that allows the laminar locator 2800 to engage the target anatomy 1300. The tip 2804 can be sized and shaped to engage any of the laminas of the spine. In other embodiments, multiple laminar locators 2800 may have tips 2804 of different sizes and/or shapes to conform to different shaped laminas at different levels of the spine due to changes in the anatomy at different levels.

In certain embodiments, the tip 2804 can include one or more angled surfaces (e.g., beveled surfaces). The angled edge(s) can be used to shave bone overgrowth (e.g., due to arthritis) at or near the lamina. For example, the laminar locator 2800 can be moved back and forth to shave bone overgrowth while the laminar locator 2800 is advanced to the lamina. In some embodiments, the laminar locator 2800 can include two angled edges on opposite sides of the tip 2804.

In some examples, the insertion of the laminar locator 2800 can be advanced to the target anatomy along a path that is substantially in line or parallel with the target anatomy 1300 (e.g., generally parallel with a posterior surface 1305 or anterior surface 1303 of the lamina or generally parallel with a plane that the bisects the inferior edge 1301 of the lamina between the anterior surface 1303 and the posterior surface 1305). Advantageously, this technique can minimize trauma to the patient and provide safety by being able to dock onto the lamina and prevent unwanted movement of the laminar locator 2800 and/or other instruments of the decompression system. In certain embodiments, the laminar locator 2800 can be advanced towards an inferior portion of the lamina (e.g., an inferior edge 1301 of the lamina between a facet and a spinous process). In certain embodiments, the laminar locator 2800 may approach the lamina from an inferior angle or position. In certain embodiments, a clinician may advance the laminar locator 2800 towards the lamina and probe around the anatomy to attempt to find a correct location for docking the locator 2800 onto the lamina. The clinician may probe the anatomy until the locator 2800 docks onto the lamina. The tip 2804 may be shaped, dimensioned, and/or otherwise configured so that it only engages a particular segment of the lamina or only engages the lamina at a particular orientation. In certain embodiments, the tip 2804 and/or any of the components thereof (e.g., the projections) can be blunt or atraumatic to prevent damage when probing the anatomy.

In some examples, once the laminar locator 2800 is docked on the lamina, a clinician may attempt to rotate the laminar locator 2800 or move the laminar locator 2800 from side to side to ensure that the laminar locator 2800 is engaged with the target anatomy 1300 and/or cannot slip off the target anatomy 1300. In some examples, fluoroscopy utilizing different imaging views can confirm the position of the laminar locator 2800. The laminar locator 2800 may be metal, plastic, carbon, fiber, or another grade material that can withstand forces within the anatomy and is biocompatible. In some examples, the laminar locator 2800 can include any and/or all of the features of the laminar locator described with respect to FIGS. 35A-35E.

In certain embodiments, after the laminar locator 2800 is docked on the lamina, the laminar locator 2800 may be used as a guide to advance one or more additional instruments to the lamina. For example, in certain embodiments, one or more dilators may be advanced over the laminar locator 2800. In some embodiments, a single dilator may be advanced over laminar locator 2800. In other embodiments, a series of sequentially larger dilators may be used to achieve a diameter sufficient for performing a laminotomy, laminectomy, or decompression procedure using the systems described herein.

FIGS. 28C-28F show an embodiment of a dilator 2810. The dilator 2810 may be part of a system for laminectomy, laminotomy, or decompression. As shown, the dilator 2810 can be positioned over the laminar locator 2800 of FIG. 28A.

The dilator 2810 can include a shaft 2812. The shaft 2812 can be cannulated or include a lumen therethrough. The distal end of the dilator 2810 can include a dilator tip 2814. The dilator tip 2814 can dissect tissue, for example tissue near the target anatomy 1300. The dilator 2810 may be slid over the laminar locator 2800. In some embodiments, one dilator 2810 may be used. In other embodiments, multiple dilators 2810 can be used for sequential dilation, e.g., to provide the diameter needed to achieve an adequate laminotomy or laminectomy. The dilator 2810 may be made of plastic, metal, a polymer, or another medical grade material. In some examples, the dilator tip 2814 can be metal to allow the tip to be visualize using fluoroscopy. The tip 2814 can be visualized using fluoroscopy to assist a clinician in navigating the tip 2814 to the target anatomy 1300 and/or confirming that the tip 2814 is docked to the target anatomy 1300.

Figure 28D:
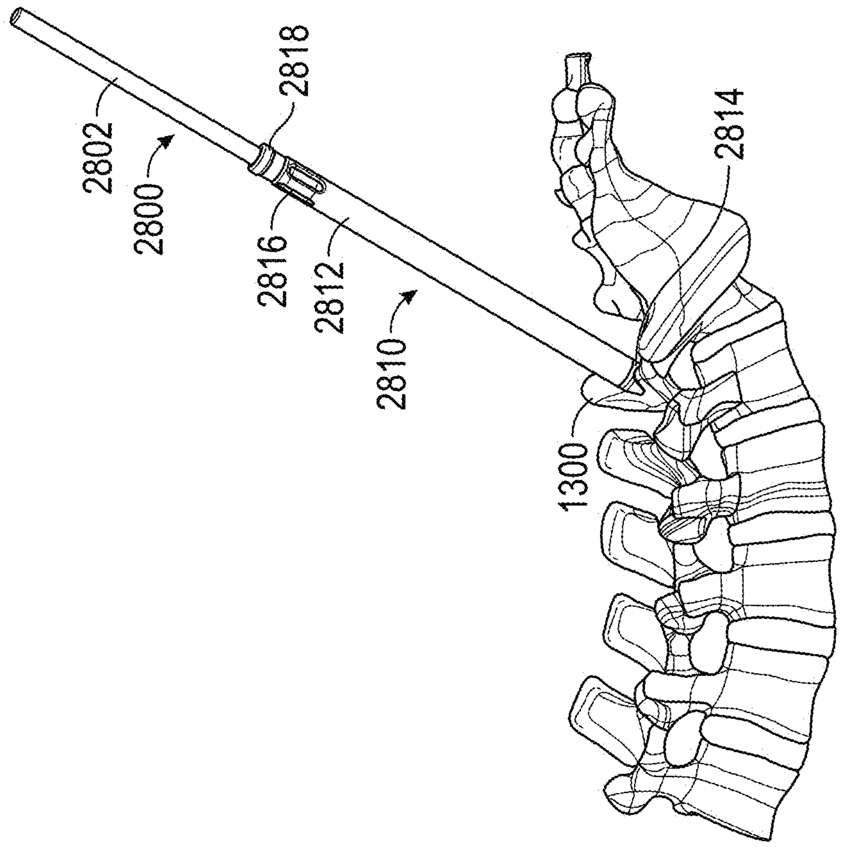
Figure 28E:
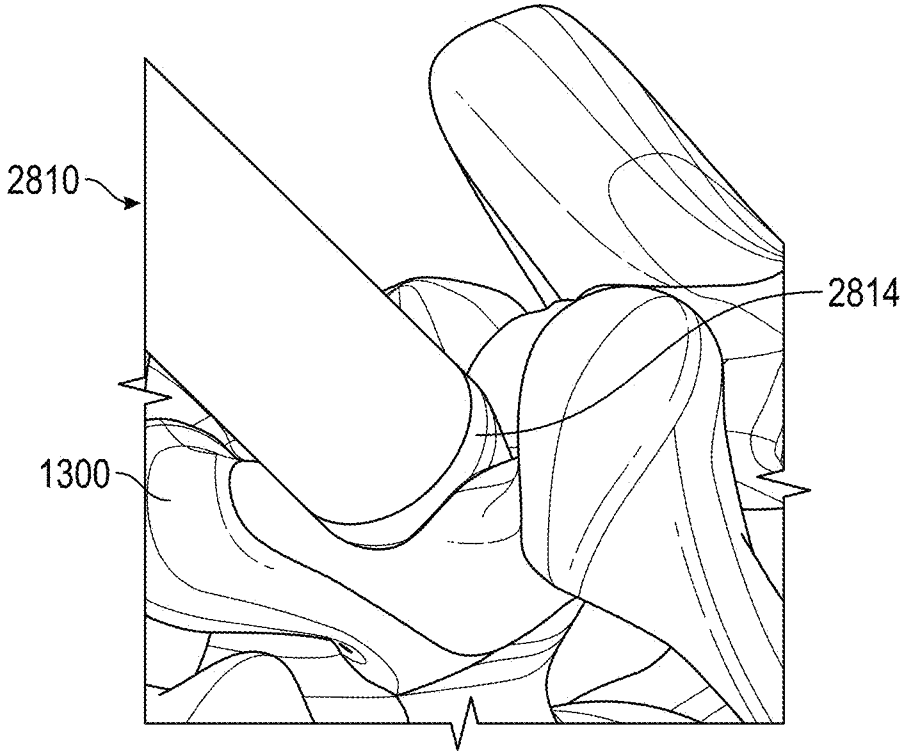

As shown in FIG. 28D and FIG. 28E, the dilator tip 2814 can be docked on the edge of the lamina. The dilator tip 2814 may be U-shaped, V-shaped, or otherwise shaped to dock on the target anatomy 1300. For example, in some embodiments, the dilator tip 2814 can include two projections. One projection may engage a posterior side of the lamina and another projection may engage an anterior side of the lamina. In some embodiments, a recessed section between the projections may engage an inferior edge of the lamina. The projections of the dilator tip 2814 can be configured to align with the projections of the locator 2800 when both are docked on the target anatomy 1300.

Figure 28F:
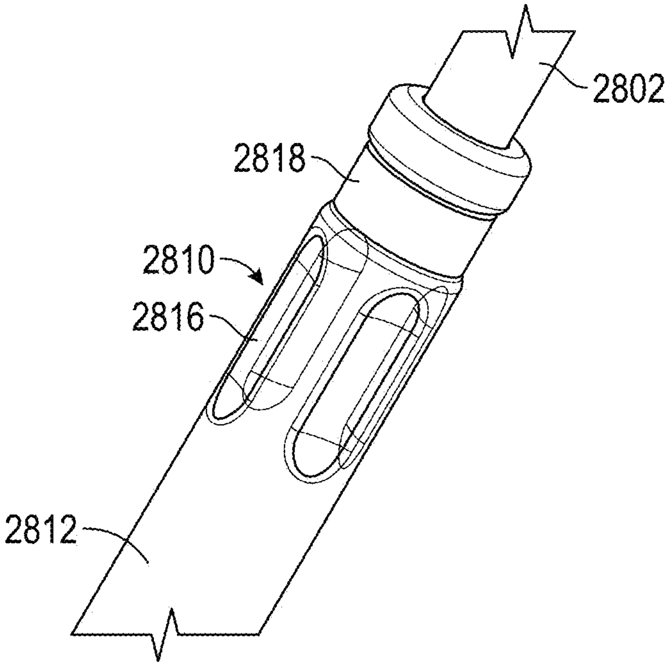

As shown in FIG. 28F, the dilator 2810 can include grips 2816. The grips 2816 can include knurling, indentations, or other features to facilitate grasping and manipulation (e.g., rotation, axial movement) of the dilator 2810. The grips 2816 can be in the form of elongate recesses extending longitudinally along the dilator 2810. The grips 2816 can be used to rotate the dilator 2810 with fingers of the user. In some examples, other instruments and devices described herein can include similar grips. The dilator 2810 can also include an indentation 2818. In some embodiments, the indentation 2818 may provide a space for attachment of other instruments. In some embodiments, the indentation 2818 may provide for case of manipulation by a user.

Figure 28H:
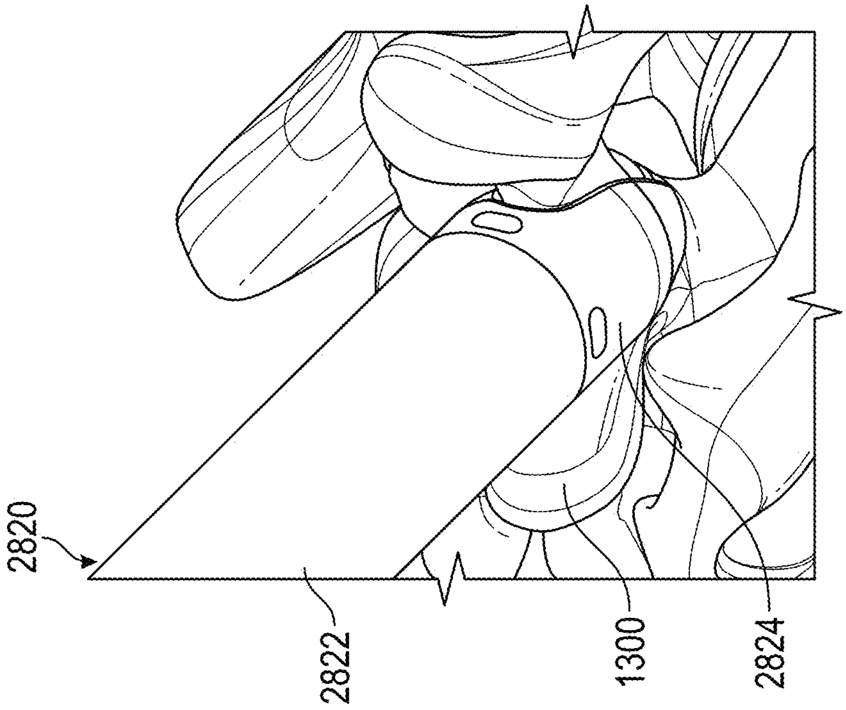
FIGS. 28G-28H show an embodiment of a cannula 2820.
Figure 28G:
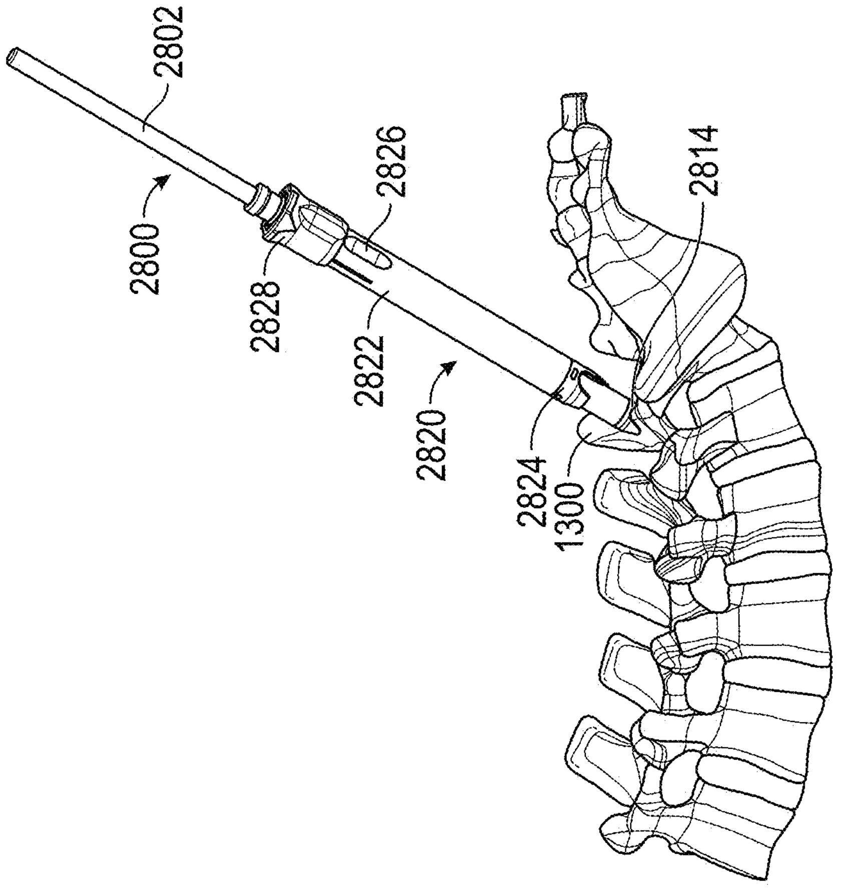
Figure 28I:
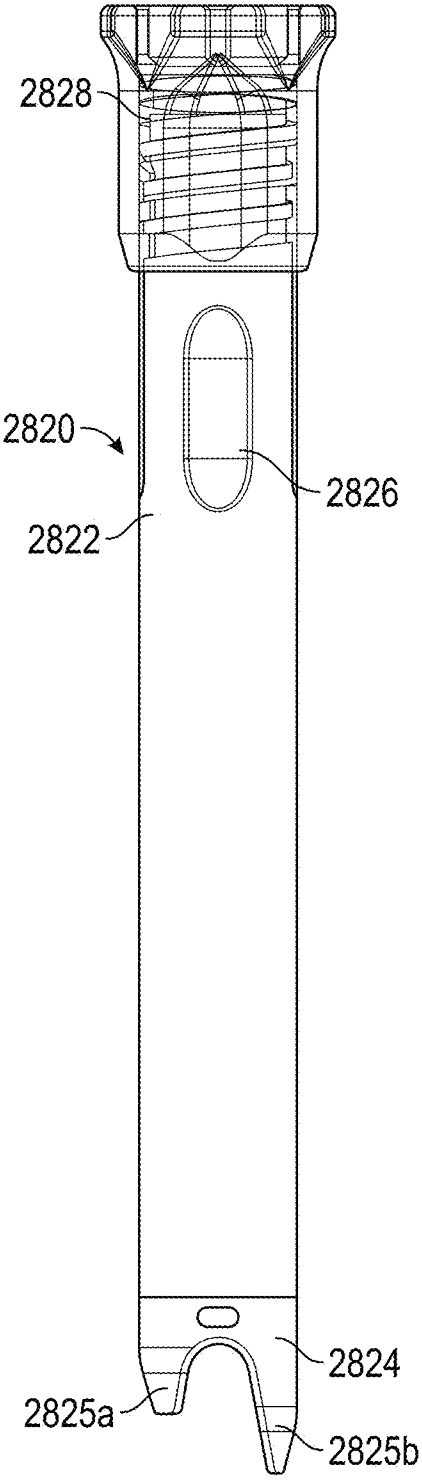
Figure 28J:
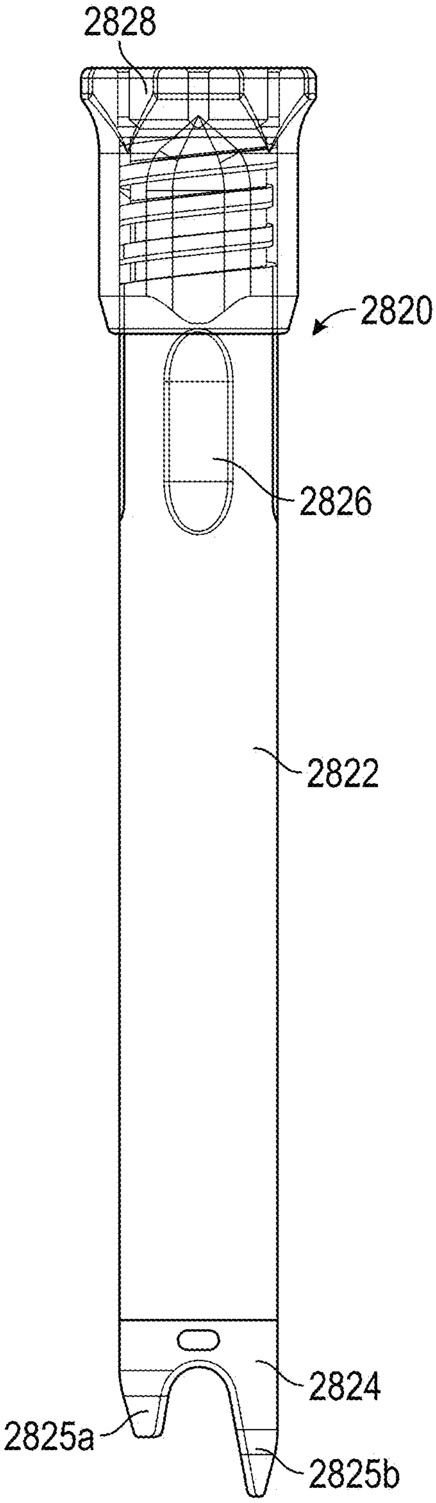

FIGS. 28G-28H show an embodiment of a cannula 2820. The cannula 2820 may be part of a system for laminectomy, laminotomy, or decompression. As shown, the cannula 2820 can be positioned over the dilator 2810 of FIG. 28C. FIGS. 281-28J show an embodiment of the cannula 2820 of FIG. 28G with a cap 2828 shown as transparent.

The cannula 2820 can include a shaft 2822. The shaft 2822 can be cannulated or include a lumen therethrough. The cannula 2820 can include a cannula tip 2824. As shown in FIG. 281, the cannula tip 2824 can be docked on the edge of the lamina. The cannula tip 2824 may be U-shaped, V-shaped, or shaped to dock on the target anatomy 1300. For example, in some embodiments, the cannula tip 2824 can include two projections. Onc projection may engage a posterior side of the lamina and another projection may engage an anterior side of the lamina. In some embodiments, a recessed section between the projections may engage an inferior edge of the lamina. The projections of the cannula tip 2824 can be configured to align with the projections of the dilator 2810 when both are docked on the target anatomy 1300.

The cannula 2820 can have a metallic cannula tip 2824. The metallic cannula tip 2824 can allow the tip 2824 to be visualized using fluoroscopy. The tip 2824 can be visualized using fluoroscopy to assist a clinician in navigating the tip 2824 to the target anatomy 1300 and/or confirming that the tip 2824 is docked to the target anatomy 1300. In some embodiments, the metallic cannula tip 2824 can act as a guard.

An inner lumen of the cannula 2820 can be used to provide a path for one or more instruments to be advanced to the target anatomy 1300. For example, after the cannula 2820 is docked at the target anatomy 1300, the dilator(s) 2810 and the locator 2800 can be removed through the lumen of the cannula 2820. Subsequently, one or more instruments may be advanced to the target anatomy 1300 through the cannula 2820. In some alternative embodiments, the locator 2800 may be removed after the dilator(s) 2810 are docked to the target anatomy 1300, but before the cannula 2820 is advanced over the dilators 2810. In some embodiments, the cannula 2820 may be a dilator. In some embodiments, the cannula 2820 may be advanced over the locator 2800 without the use of a separate dilator 2810.

As shown in FIGS. 281 and 28J, the cannula tip 2824 can have hooks and/or extensions 2825*a,b* for improving docking on the lamina. In some examples, the cannula tip 2824 can have a hook and/or extension 2825*a,b* on either side, configured to surround the lamina. For example, in certain embodiments, the hook and/or extension 2825*a* may be configured to engage the posterior side of the lamina and the hook and/or extension 2825*b* may be configured to engage the anterior side of the lamina when the tip 2824 is docked on the lamina. The inferior hook and/or extension 2825*b* can be longer than the superior hook and/or extension 2825*a*.

The hook and/or extensions 2825*a,b* can individually and/or in combination act as a guard to prevent injury to the nerves or spinal cord, for example, by forming a barrier between instruments advanced through the cannula and the surrounding anatomy.

The cannula can be used to advance one or more instruments for a laminectomy, laminotomy, or decompression therethrough. In some embodiments, drill bits or bone removing instruments, such as a pituitary or kerrison, can be delivered through the cannula 2820, for example, after the laminar locator 2800 and/or dilator 2810 have been removed. The drill bit or bone removing instruments can extend to a point short of the inferior extension and/or hook. The shorter extension and/or hook 2825*a* can slide on the posterior side of the lamina once the cannula 2820 is docked. This superior extension and/or hook 2825*a* can slide on the posterior portion of the lamina and prevent rotation or migration of the cannula 2820 while working in conjunction with the inferior extension and/or hook. The cannula 2820 can be rotated to ensure docking is correct and the cannula 2820 is prevented from moving. The inferior hook and/or extension 2825*b* of the cannula tip 2824 can act as a nerve shield.

In some embodiments, the cannula 2820 may have a diameter of between about 1 mm and about 60 mm. More preferably, in some embodiments, the cannula 2820 may have a diameter of between about 8 mm and about 40 mm. Even more preferably, in some embodiments, the cannula 2820 may have a diameter of between about 12 mm and about 30 mm. Advantageously, the cannula 2820 can allow for direct visualization of the target site 1300.

As shown in FIGS. 281 and 28J, the extensions 2825*a* and 2825*b* may taper inwardly relative to the cannula shaft 2822. In some embodiments, the cannula 2820 can include a cap 2828 on the proximal end. The cap 2828 can be threaded to engage with the proximal end of the shaft 2822 of the cannula 2820. The cap 2828 can be adjusted by rotating the cap 2828 relative to the shaft 2822. The adjustable cap 2828 can be used to set the drill depth. As described with respect to FIGS. 30A-30F, the cap 2828 can contact a portion of the drill guide, which contacts a drill stop of a drill or a stop of another bone removing instrument, in order to prevent the instrument from reaching to a further depth.

The cannula 2820 may have grips 2826. The grips 2826 can include knurling, indentions, or features to facilitate grasping and manipulation (e.g., rotation, axial movement) of the cannula 2820, for example, to facilitate insertion. In some embodiments, the grips 2826 can be in the form of elongate recesses extending longitudinally along the shaft 2822.

Figure 28L:
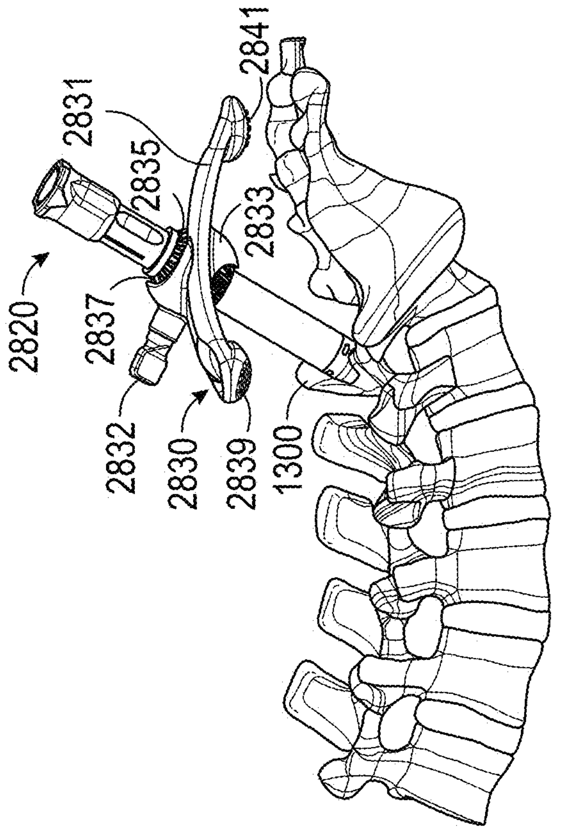
FIGS. 28K-28M show an embodiment of a base plate or stabilizer 2830.
Figure 28K:
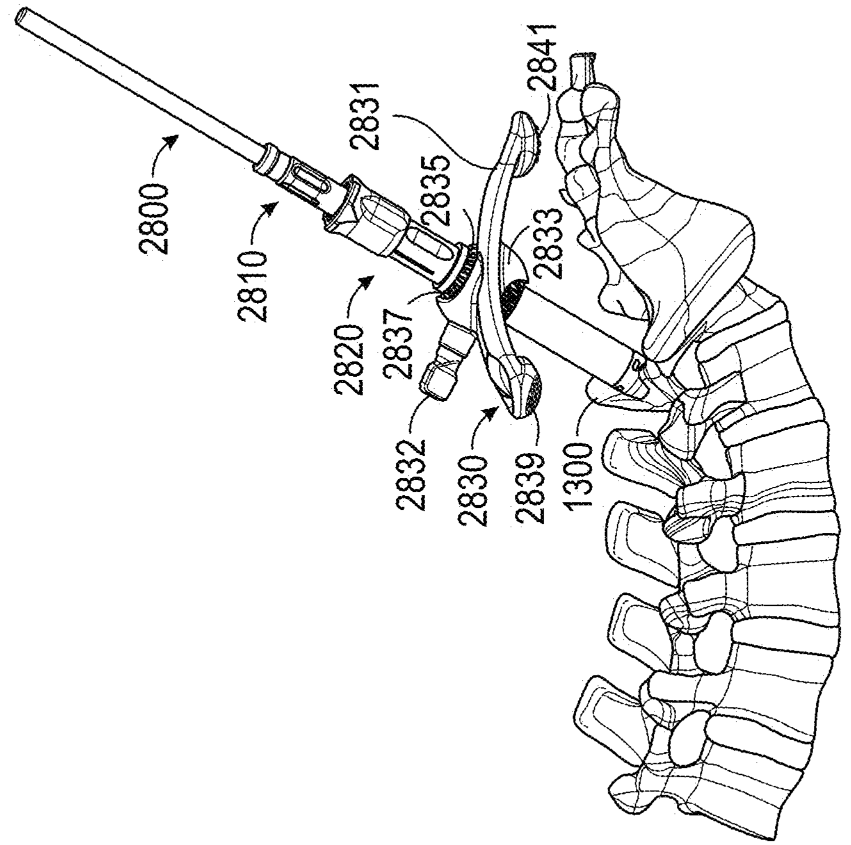
Figure 28M:
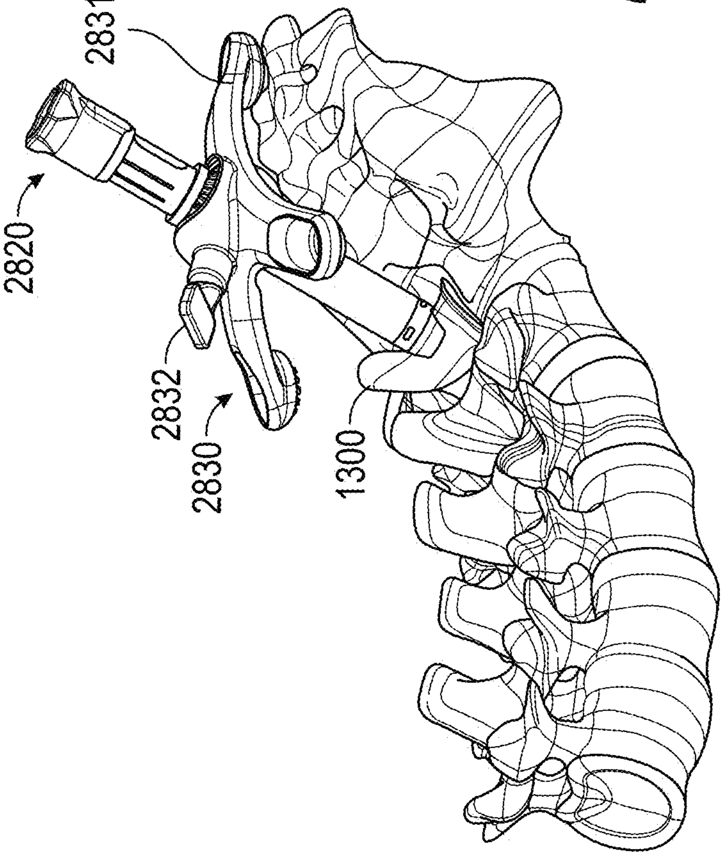

FIGS. 28K-28M show an embodiment of a base plate or stabilizer 2830. The stabilizer 2830 can be part of a system for laminectomy, laminotomy, or decompression. The stabilizer 2830 can include any or all of the features of the skin stop described with respect to FIGS. 25A-25D.

The stabilizer 2830 can secured to the cannula 2820. For example, the stabilizer 2830 can be secured to the shaft 2822 of the cannula 2820. In some embodiments, the stabilizer 2830 can be advanced over the cannula 2820 and then secured to the shaft 2822 when positioned at a desired location. As shown in FIG. 28K, the stabilizer 2830 can be advanced over the cannula 2820 when the dilator 2810 and laminar locator 2800 are positioned within the cannula 2820. The dilator 2810 and laminar locator 2800 may then be removed from within the cannula 2820 as shown in FIG. 28L. In other embodiments, one or both of the dilator 2810 and laminar locator 2800 may be removed before the stabilizer 2830 is secured to the shaft 2822.

The stabilizer 2830 can be advanced along the cannula 2820 until positioned at a desired position on top of the patient's skin and/or drapes and then locked in place to the cannula 2820 to prevent or hinder movement or migration of the cannula 2820 and/or other instruments during surgery. Advantageously, this can prevent unintended movement while reaming or removing bone. Such unintended movement can risk nerve damage.

The stabilizer 2830 can have one or more legs, two or more, or preferably three or more legs 2831 configured to contact the skin of the patient. The legs can contact the skin to maintain balance and prevent or hinger movement or migration of the cannula and/or other instruments during surgery. Each leg can include a contact surface 2839 for contacting the skin of the patient. The contact surface 2839 can include one or more surface features 2841. The surface features 2841 can include one or more protrusions, teeth, or other surface features to prevent slipping or increase friction when positioned against the skin. The surface features 2841 can be rough, abrasive, or otherwise textured surfaces to prevent slipping when positioned against the skin. In some embodiments, the surface features 2841 may be a non-slip material.

The stabilizer 2830 or components thereof (e.g., the legs 2831) can be rotated to maneuver in different planes. The legs 2831 can extend laterally from a main body 2833. The main body 2833 may be coupled to and extend at least partially around a central body 2835. As shown, the central body 2835 may include a plurality or ribs 2837. The central body may be generally spherical in shape. The central body 2835 may secure to the shaft 2822 of the cannula 2820. The main body 2833 can be configured to rotate along multiple axes relative to the central body 2835 to allow the legs to rotate along multiple axes relative to the central body 2835 and/or cannula shaft 2822. For example, the main body 2833 (and legs 2831) may rotate around a longitudinal axis of the cannula shaft 2822 (or a longitudinal axis of the central body 2835) and/or around one or more axes perpendicular to the longitudinal axis of the cannula shaft 2822 (or longitudinal axis of the central body 2835). The main body 2833 may rotate in a similar manner as a ball and socket joint. The main body 2833 may freely rotate and then lock at any angle relative to the central body 2835. For example, FIG. 28M depicts the main body rotated to a different position relative to its position in FIG. 28L. The main body 2833 and legs 2831 can be rotated to a desired orientation to position the legs 2831 at a desired location on the skin of the patient. This rotation can be used to accommodate patients having different anatomies or procedures being performed at different levels of the spine.

The stabilizer 2830 or components thereof (e.g., the legs 2831) can be advanced axially along the cannula 2820 to adjust a relative height of the stabilizer 2830 to position the legs at their desired location (e.g., on the skin of the patient).

When the legs 2831 are positioned at a desired height and/or angular orientation, the legs 2831 can be locked into place with a knob 2832 or other means of locking. For example, the knob 2832 can be actuated to release and secure the stabilizer 2830 to the cannula 2820. The knob 2832 can also be actuated to release and secure the position of the main body 2833 relative to the central body 2835 and/or relative to the cannula. In some embodiments, the knob 2832 may be advanced away from the central body so that a portion of the knob disengages from the cannula 2820 to allow for rotation of the main body and axial movement of the stabilizer along the cannula 2820. The knob 2832 can be advanced towards the central body so that a portion of the knob 2832 engages the cannula to prevent rotation of the main body and axial movement of the stabilizer relative to the cannula 2820 . . . . The stabilizer 2830 can be made of metal, plastic, or other radiolucent, or radiopaque material. The knob 2832 can be actuated to allow the legs to freely rotate and lock at any angle. The knob 2832 can lock the main body 2833 in place relative to the central body 2835 and/or cannula 2820. This can allow for specific positioning of the stabilizer 2830 with respect to the anatomy of the patient.

In some embodiments, the laminar locater 2800 and/or dilator(s) 2810 can be maintained within the cannula 2820 and docked to the lamina until the stabilizer 2830 is locked in position in contact with the skin of the patient or a drape over the skin of the patient. This can prevent movement of the cannula 2820 before the stabilizer 2830 is locked in position. In some embodiments, the laminar locator 2800 and/or dilator(s) 2810 are removed after the stabilizer is locked into position.

Figure 29A:
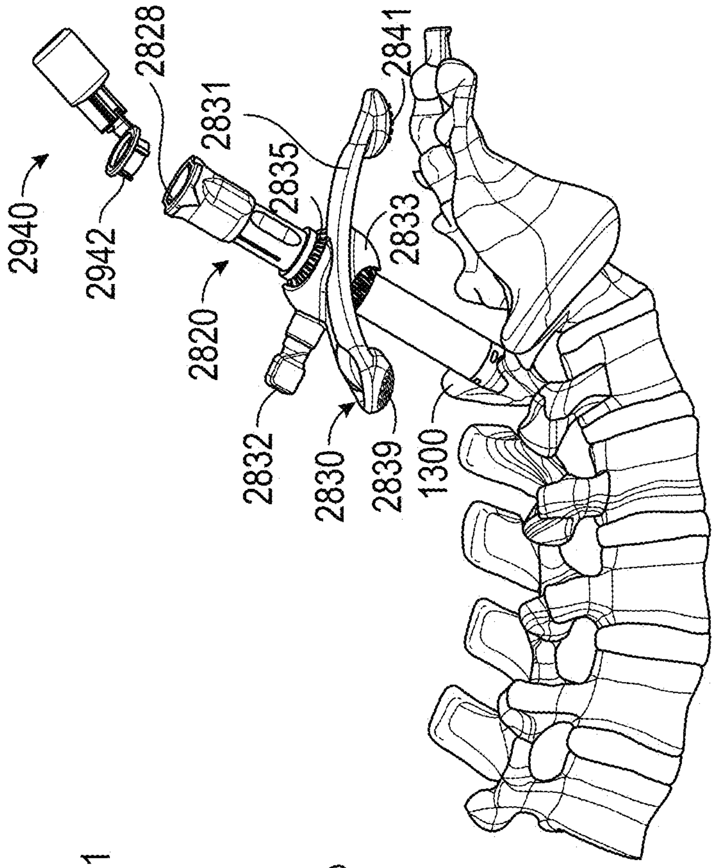
FIGS. 29A-29C show an example of a light with a bracket being positioned on the cannula of FIG. 28L.
Figure 29C:
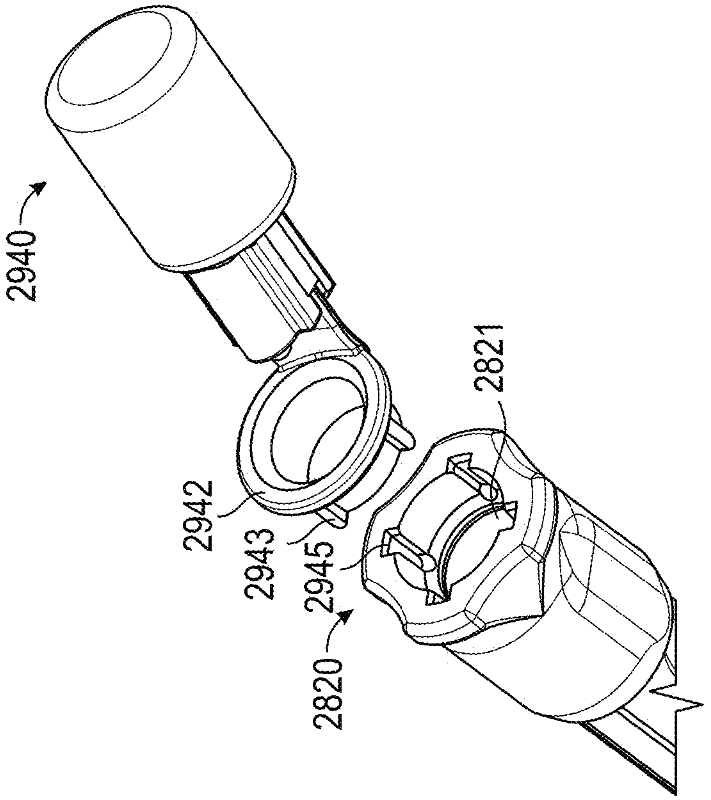
Figure 29B:
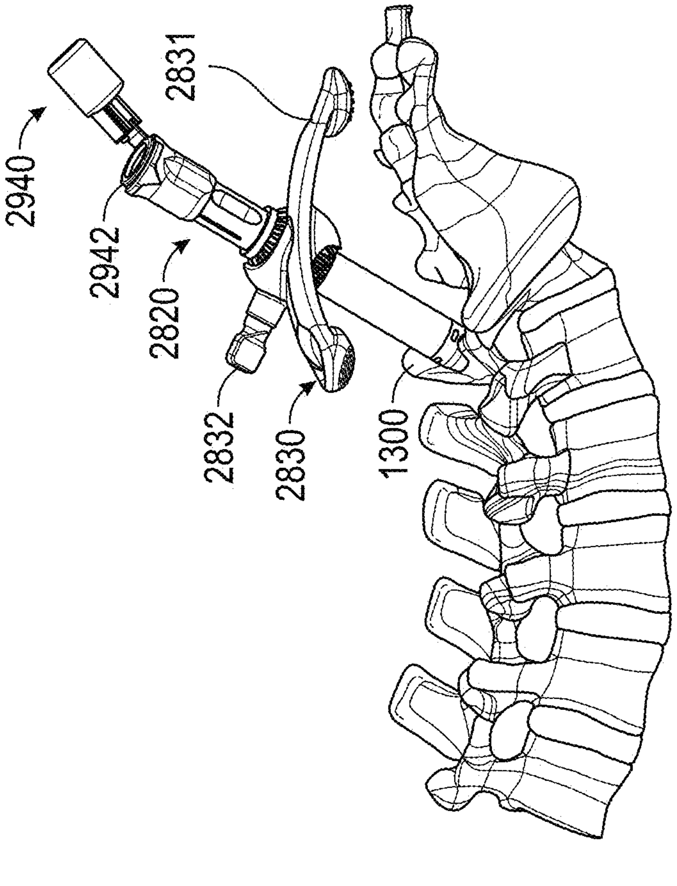

FIGS. 29A-29C show an embodiment of a light 2940 with a bracket 2942. As shown, the light 2940 and bracket 2942 can be coupled to the cannula 2820. In some embodiments, the light 2940 can be removably coupled to the bracket 2942.

The light source 2940 can be disposable or non-disposable. The light source 2940 may be clipped on, slid on, or otherwise attached to a proximal end of the cannula 2820 or to the cap 2828 to help a physician visualize the anatomical elements that have to be removed to decompress the spine. The light source 2940 can be actuated by pulling a tag, pressing a button, or any other actuation mechanism. The light source 2940 can include a bracket 2942 that can couple with a proximal end of the cannula 2820. For example, the bracket 2942 can couple with the cap 2828 and/or socket of the cannula 2820. For example, the bracket 2942 may include one or more protrusions 2943 or other coupling features that may couple to one or more slots 2945 or other coupling features of the cap 2828 or the proximal end of the cannula 2820. The light source 2940 may include a light-emitting diode (LED) light, a halogen light, or any other suitable light. In some embodiments, the light source 2940 may include an internal power source so that additional wiring through the operating room is not needed to provide power to the light source 2940.

In some embodiments, after the cannula 2820 is docked to the target anatomy 1300, an instrument guide (e.g., a drill guide) may be advanced through the lumen 2821 of the cannula 2820. The drill guide may be used to narrow the path (e.g., provide a more narrow lumen than the cannula 2820) for advancing and using an instrument (e.g., a drill) at the target anatomy 1300.

FIG. 30A-30F show an embodiment of an instrument guide 3050. The instrument guide 3050 may be part of a system for laminectomy, laminotomy, or decompression. As shown in FIGS. 30A-30F, the instrument guide 3050 can be positioned within the cannula 2820. The instrument guide 3050 can be advanced through the cannula 2820 to the target anatomy.

An instrument guide 3050 (e.g., a drill guide) may be inserted into the cannula 2820 to allow a drill bit, Kerrison, pituitary, or other bone removing instrument to remove different regions of the lamina, bone, or target anatomy 1300.

The instrument guide 3050 may include one or more lumens that may form a path to guide an instrument to a desired location of the target anatomy 1300. The one or more lumens of the instrument guide 3050 can be smaller (e.g., in circumference) than the lumen of the cannula 2820 to guide any instruments to a more precise location than if advanced solely through the lumen of the cannula 2820 in the absence of the drill guide. In certain embodiments, as described in further detail herein, instrument guide 3050 can provide multiple paths (e.g., via multiple lumens or a single lumen that is movable within the cannula 2820) to multiple locations of the target anatomy. In this way, the lumen of the cannula 2820 can at least partially define an overall working area of the target anatomy over which instruments may be guided by the instrument guide 3050, and the instrument guide 3050 can be used to guide the instruments to more precise locations within the overall working area. This can advantageously allow a user to perform a more precise decompression procedure and/or avoid areas that may harm a patient. For example, in some procedures drilling or reaming down the center of the lumen of the cannula could potentially harm the patient by injuring the nerves, nerve root, or the spinal cord. The instrument guide 3050 can provide one or more narrower paths that can prevent the drill or other instrument from traveling straight down the center of the lumen of the cannula.

The instrument guide 3050 can include a stop member 3058 that extends radially outward from a shaft 3052 of the instrument guide 3050. The stop member 3058 can contact a proximal end of the cannula 2820 or the cap 2828 of the cannula 2820 to control a depth of the instrument guide 3050 and/or instruments inserted through the instrument guide. In some embodiments, the instrument guide 3050 can include one or more protrusion 3053 or other coupling features that can couple with the one or more recesses or slots 2945 of the cap 2828. In certain embodiments, the coupling between the protrusions 3053 and the slots 2945 can prevent rotation of the instrument guide 3050 relative to the cannula 2820.

Figure 30B:
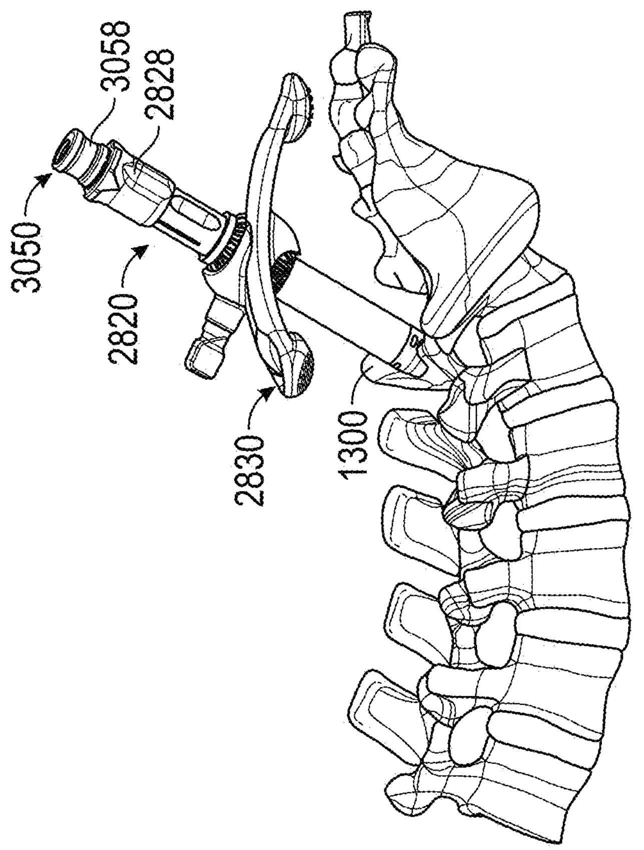
FIG. 30A-30F show an example of a drill guide being positioned in the cannula of FIG. 28L.
Figure 30A:
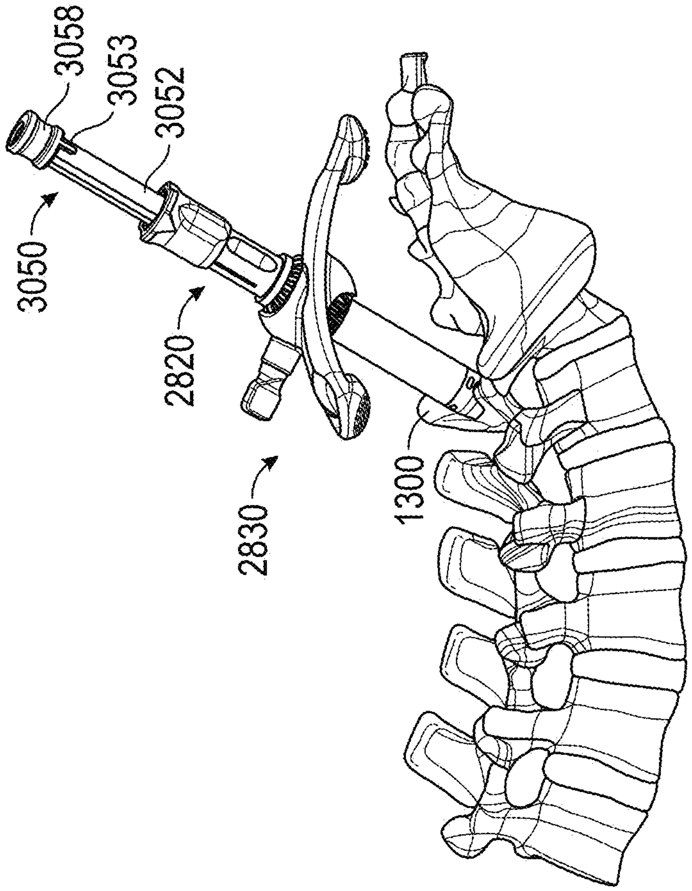
Figure 30C:
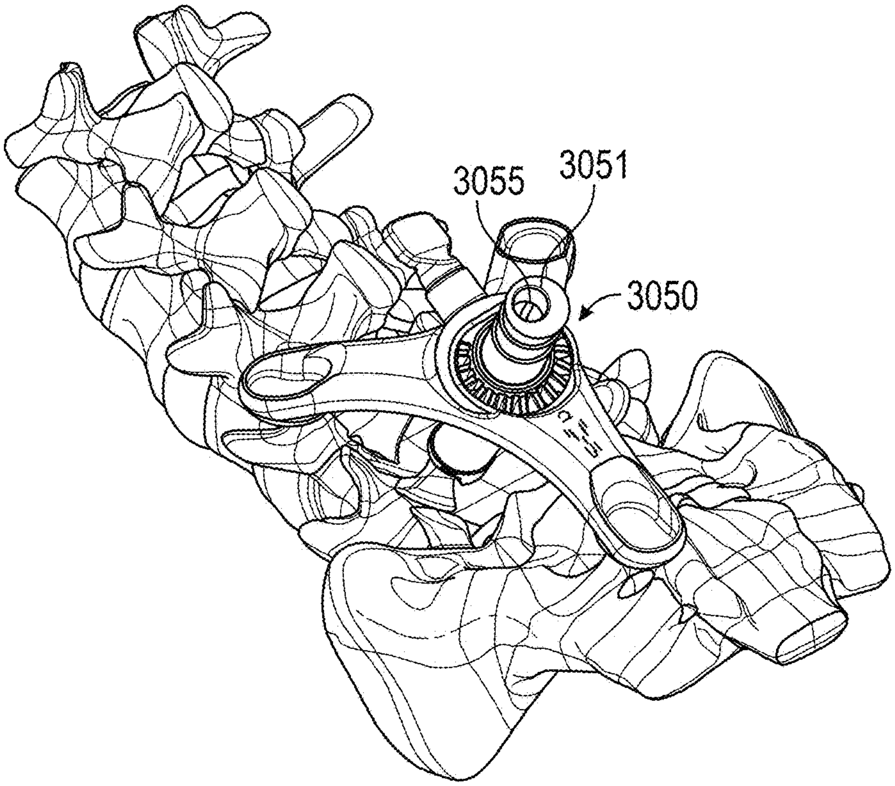
Figure 30D:
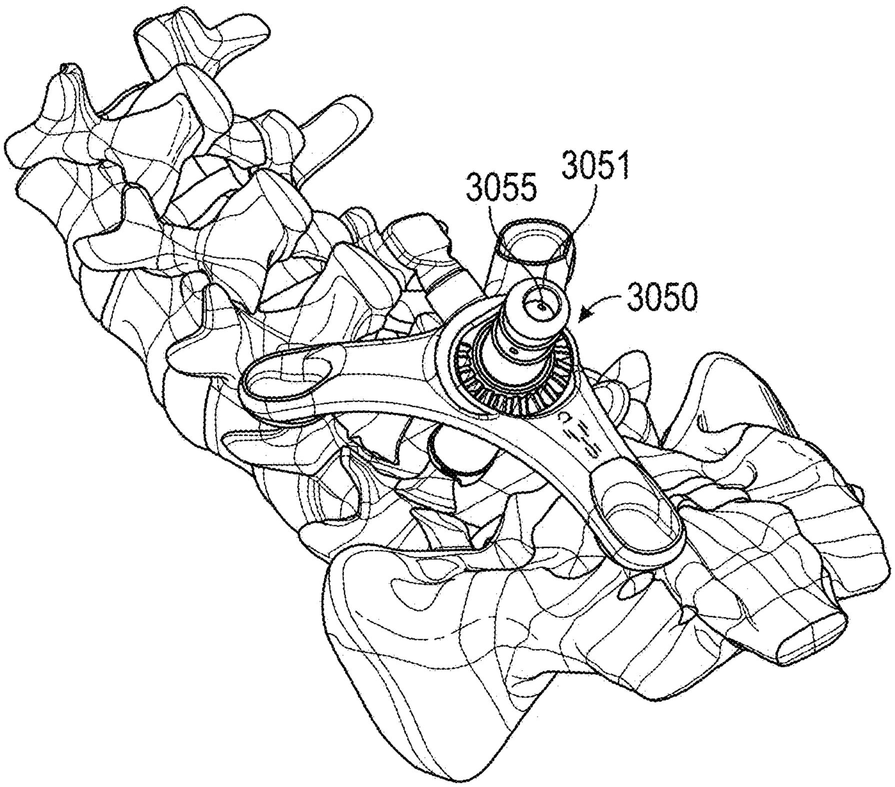
Figure 30E:
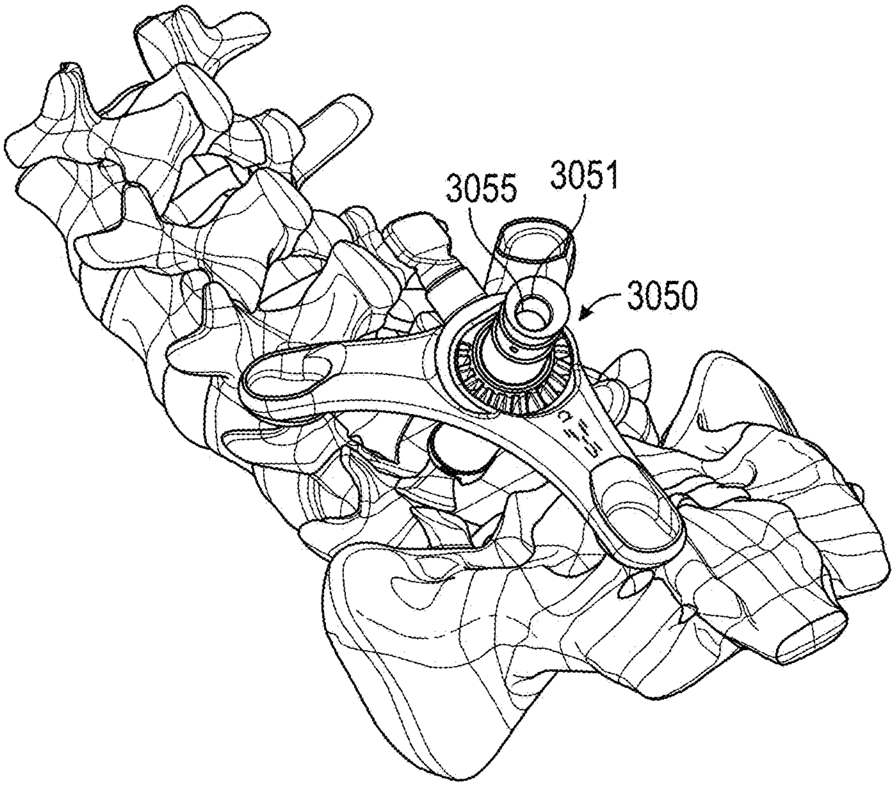
Figure 30F:
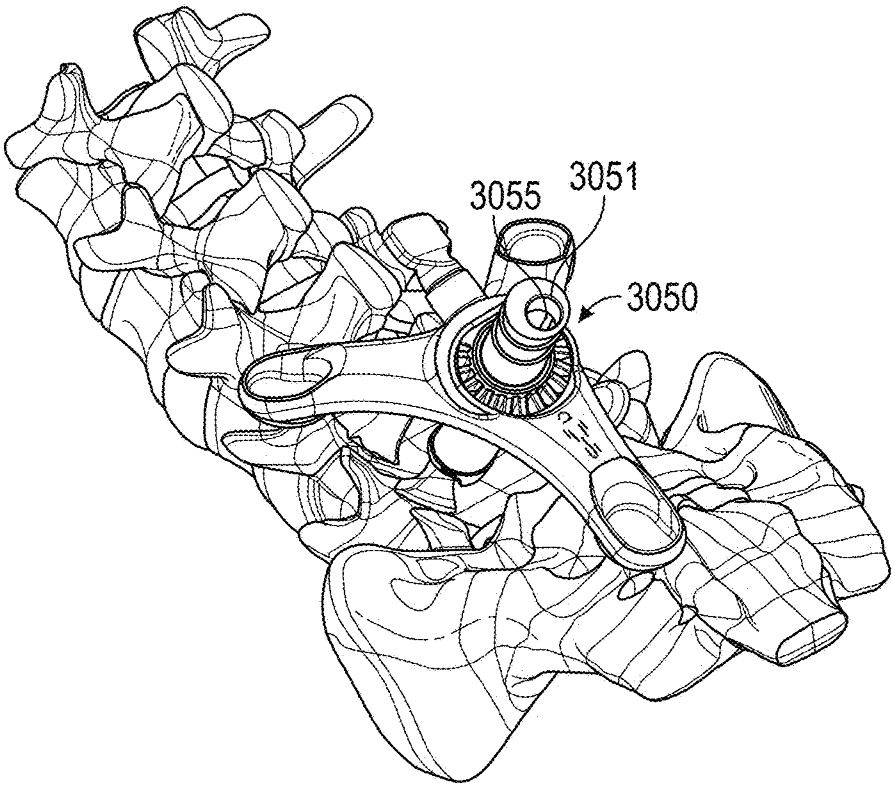

As shown in FIG. 30C-30F, the instrument guide 3050 can include an aperture 3051. The aperture 3051 can lead to a guide lumen 3055 extending through the instrument guide 3050. The aperture 3051 and guide lumen 3055 can be offset from the center of the longitudinal axis of the instrument guide 3050. The aperture 3051 and guide lumen 3055 of the instrument guide 3050 may be rotated into different positions relative to the cannula 2820 and/or target anatomy 1300 to provide for different paths to the target anatomy and/or to provide for access to different sections of the target anatomy. For example, in certain embodiments, the aperture 3051 and guide lumen 3055 can be positioned at a first orientation, as shown in FIG. 30C, to allow an instrument to advance to and operate on a first section of the target anatomy 1300. The aperture 3051 and guide lumen 3055 can be rotated to a second position, as shown in FIG. 30D to allow an instrument to advance to and operate on a second section of the target anatomy 1300. The aperture 3051 and guide lumen 3055 can be rotated to a third position, as shown in FIG. 30E to allow an instrument to advance to and operate on a third section of the target anatomy 1300. The aperture 3051 and guide lumen 3055 can be rotated to a fourth position, as shown in FIG. 30E to allow an instrument to advance to and operate on a fourth section of the target anatomy 1300. In some embodiments, at each position, the guide lumen 3055 of the instrument guide 3050 can be positioned along a distinct longitudinal axis parallel with and offset from the longitudinal axis of the cannula 2820.

During a procedure, bone can be removed at one position, and then the aperture 3051 and guide lumen 3055 can be rotated to allow for removal of bone at another position. This process can be repeated for additional positions depending on the procedure. In some embodiments, this process may be used to remove bone at multiple locations while avoiding harming the nerves, nerve root, or the spinal cord. Bone may be removed at multiple locations to form a larger combined laminar hole or recess (for example, as shown in FIG. 31C). This can be particular advantageous when performing a laminotomy from an inferior approach as described herein in which the instruments approach along a path that is generally parallel with the lamina or generally parallel with a plane that bisects the inferior edge of the lamina between the anterior side and posterior side of the lamina. As shown, for example in FIG. 31C, a laminar hole or recess may desirably be wider along the laminar edge than it is tall (between the anterior and posterior sides). Using a single path large enough to form a laminar hole or recess having such a width may risk harm to the anatomy above the posterior side of the lamina and above the posterior side. The present system can advantageously allow for removing bone at more than one location along the inferior edge of the lamina while maintaining access to the target area by keeping the cannula docked to the lamina while moving the guide to adjust the position of the guide lumen.

In some embodiments, the aperture 3051 and guide lumen 3055 can be rotated by rotating the guide 3050 relative to the cannula 2820. In some embodiments, the guide 3050 can be releasably rotationally secured relative to the cannula 2820 at each position of the aperture 3051 and guide lumen 3055. In some embodiments, one or more protrusions 3053 can couple with different slots 2945 at each position to prevent rotation of the instrument guide 3050 at each position when the protrusions 3053 are positioned within the slots 2945.

In some embodiments, the instrument guide 3050 can have between 2 and 4 positions. In some embodiments, the instrument guide 3050 can have between 1 and 5 positions. In some embodiments, the instrument guide 3050 can have between 1 and 10 positions. In some examples, the instrument guide 3050 can rotate to any position along the rotational axis. In some examples, there may be markings on the instrument guide 3050 to indicate alignment at different positions. In some embodiments, the markings can indicate a sequential arrangement for removing certain areas of bone before others. The markings may be pad printed, engraved, or another means of identifying the positions. Once the instrument guide 3050 is inserted and secured at a particular position, a drill or reamer may be placed through the instrument guide in that position to remove bone. In some embodiments, a suction tube or suction tip may be utilized to remove bone, dust, fragments, or pieces that remain after removing bone. In some embodiments, a Kerrison or pituitary may also be used to remove bone fragments, or other bone or ligament left in. The light source 2940 described with respect to FIGS. 29A-29C may be utilized to help visualize remaining bone or fragments left, or other regions of bone that need to be removed to create enhanced or optimal decompression. In some embodiments, the light source 2940 can be coupled to the instrument guide 3050.

Figure 31B:
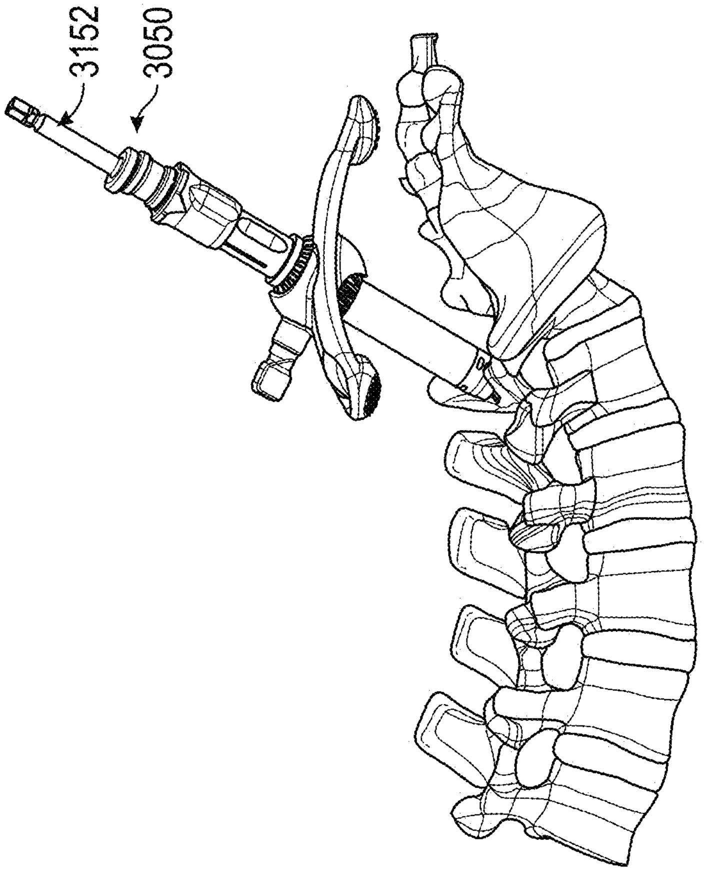
FIGS. 31A-31B show an example of a drill bit being inserted in the drill guide of FIG. 30A.
Figure 31A:
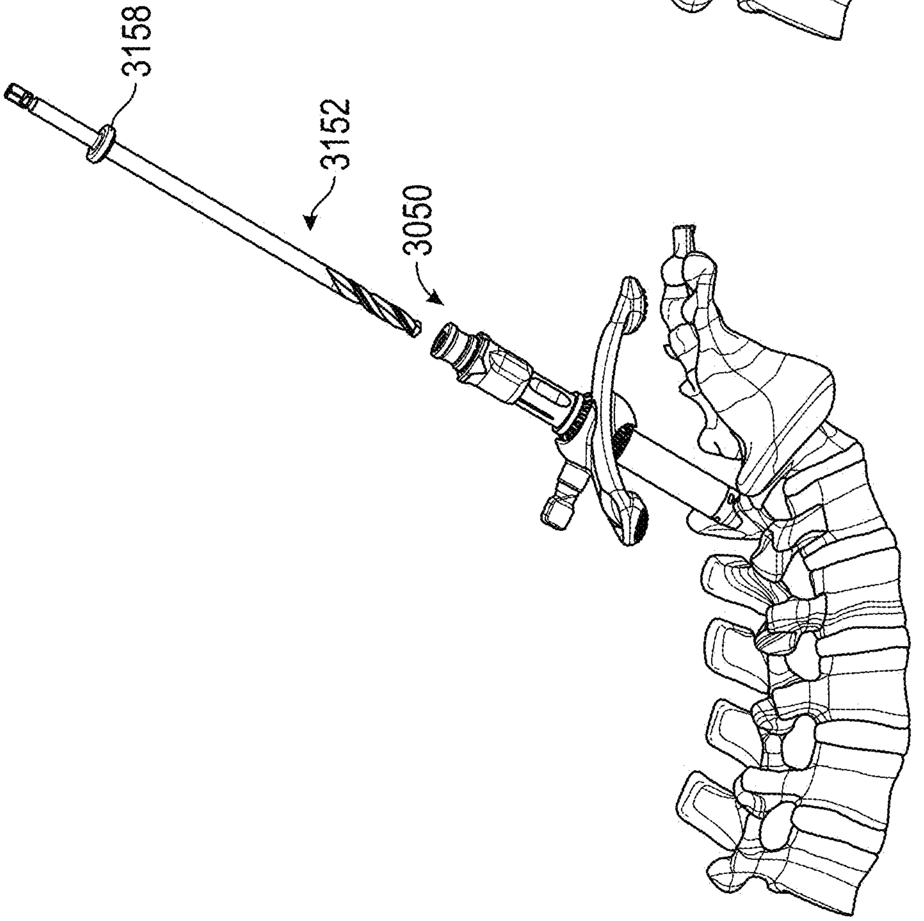
Figure 31C:
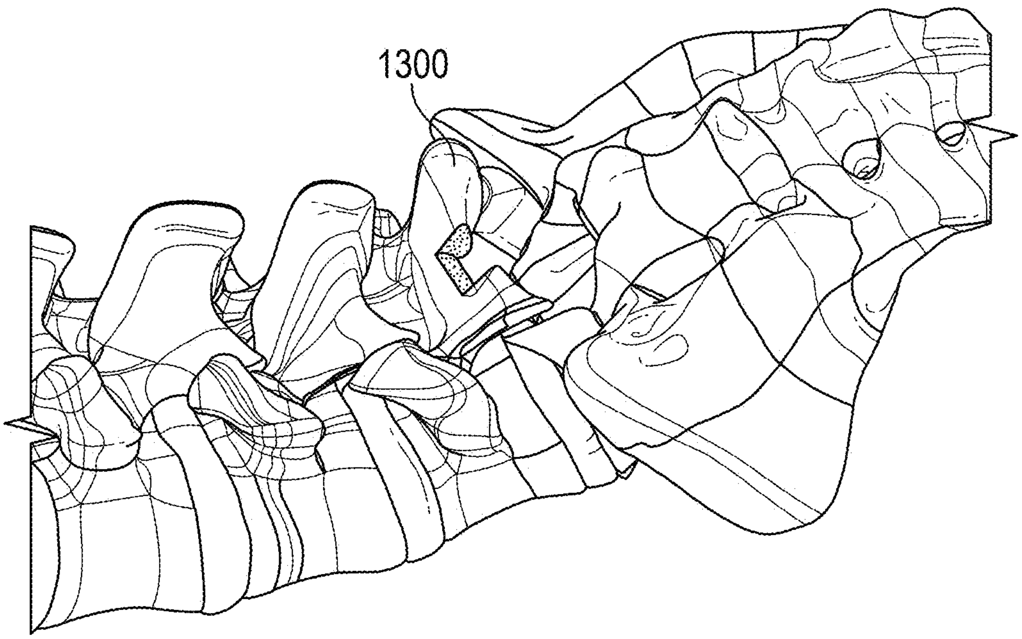
FIG. 31C shows an example of a target anatomy after bone has been removed.

FIGS. 31A-31B show an embodiment of a drill bit 3152. The drill bit 3152 can be part of a system for laminectomy, laminotomy, or decompression. As shown in FIGS. 31A-31B, the drill bit 3152 can be inserted in the instrument guide 3050. FIG. 31C shows an example of a target anatomy 1300 after bone has been removed to form a laminotomy hole or recess. In certain embodiments, the systems and devices described herein can form a laminotomy hole or recess between 3 mm and 20 mm, or more preferably between 5 mm and 14 mm. Formation of the hole or recess can decompress the spinal cord and minimize stenosis symptoms.

A drill bit 3152 may also come in a kit with the instruments described herein. The drill bit 3152 may be used with a hand drill or power drill. The drill bit 3152 can have a drill stop 3158 configured to contact the instrument guide 3050. In some examples, the drill bit 3152 can have a diameter of between around 5 mm and around 15 mm. In some examples, the drill bit 3152 can have a diameter of between around 8 mm and around 12 mm. A reamer or trephine may be utilized to remove bone in a similar manner to the drill bit 3152.

Once the adequate decompression is performed, the instruments may be removed. Advantageously, the procedure may be used to create a minimally invasive decompression to avoid large incisions and long recovery times. This devices and systems described herein may also be utilized to remove disk material. Different approaches to the target anatomy 1300 can be used depending on where tissue or bone removal needs to occur to provide decompression. For example, as described above, the instruments may advance to the lamina from a position inferior to the inferior edge of the lamina. In some embodiments, the instruments may advance to the lamina from a position inferior and posterior to the inferior edge of the lamina and can advance in superior and anterior directions. Alternatively, the instruments may follow a direct lateral trajectory to remove disc material from a lateral approach. The methods described herein may also be utilized to remove bone, cartilage, and tissue from the sacroiliac joint, or facet joint, and/or to post-pack bone graft to create a bony fusion.

Figure 32A:
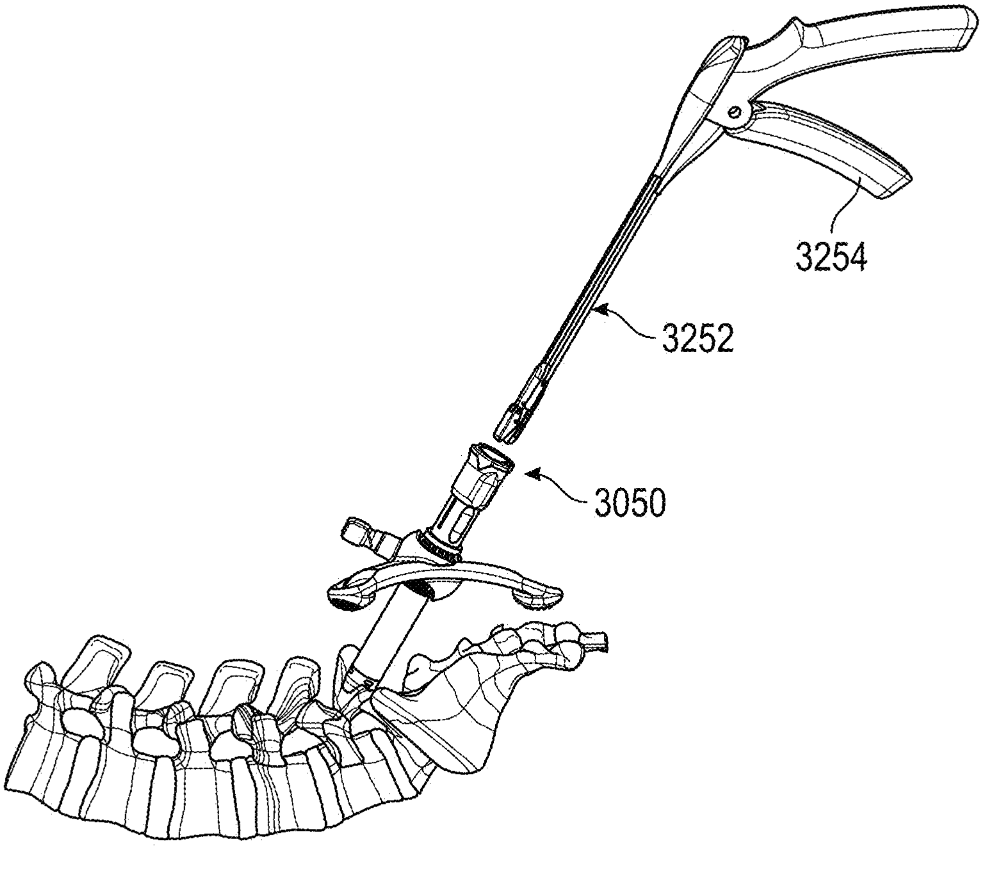
FIGS. 32A-32B show an example of a pituitary rongeur being inserted in the drill guide of FIG. 30A.
Figure 32B:
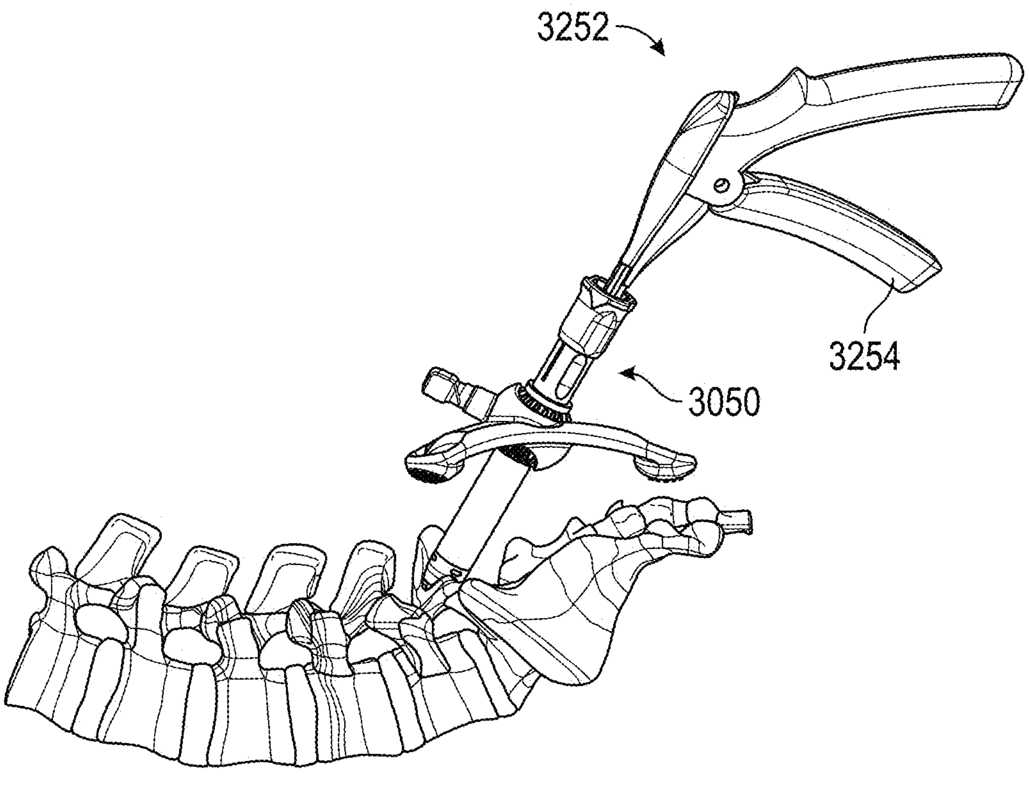

FIGS. 32A-32B show an embodiment of a pituitary rongeur 3252. The pituitary rongeur 3252 can be part of a system for laminectomy, laminotomy, or decompression. As shown in FIGS. 32A-32B, the pituitary rongeur 3252 can be inserted in the instrument guide 3050.

The pituitary rongeur 3252 can be used to remove bone using a similar method as the drill bit described with respect to FIGS. 31A-31C. The pituitary rongeur 3252 can have a trigger 3254 to actuate the distal end for bone removal. The pituitary rongeur 3252 or Kerrison may include a dead stop near the handle to prevent the instrument from plunging and provide safety from nerve root injury or spinal cord injury. The pituitary rongeur 3252 or Kerrison can be made to be reusable or formed of disposable materials, including metals, plastics, or other polymers that can allow for sterilization and autoclaving.

The dilators, working channels, or cannulas (e.g., cannula 2820) described herein may also be adjustable to allow for reaching greater depth. The dilators and/or working channels can include top knobs or caps to allow for adjustability. Advantageously, this can incrementally allow for removing bone at a greater depth to achieve a greater decompression The methods described herein can include malleting one or more of the instruments described. A mallet can be included in the kit that can help push instruments through tissue. The kit can be sterilized, using ethylene oxide, gamma, or e-beam, radiation, or any other means of sterilization.

In some embodiments, a laminectomy, laminotomy, or decompression procedure may be performed without using a guide that provides for multiple paths to the target anatomy as described herein. Instead, a user may pass a laminar locator 2800 to the lamina, position a dilator 2810 and/or cannula 2820 under the lamina, and drill into the inferior edge or border of the lamina through the lumen of the dilator 2810 or the cannula 2820. In some examples, the decompression can occur without positioning the drill or other bone removal device in multiple positions, but instead advancing the instruments along a single path to the target anatomy.

Figure 33B:
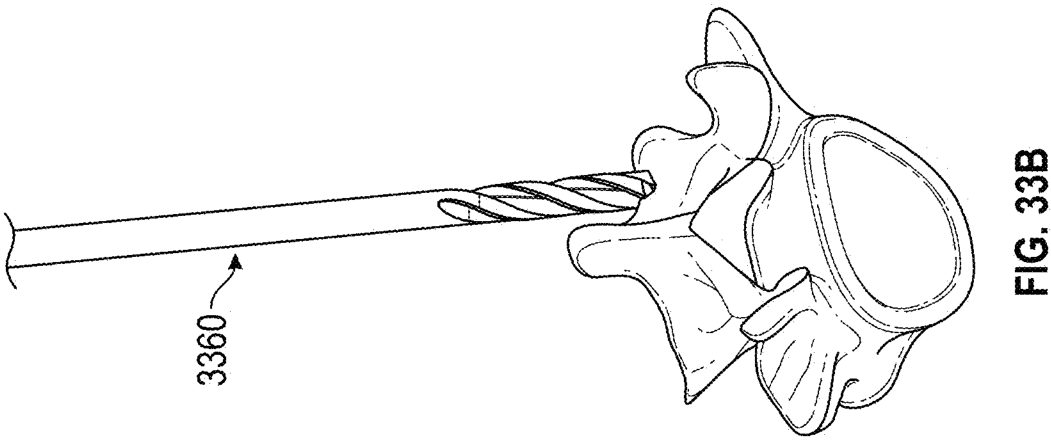
FIG. 33B shows a drill bit drilling into the inferior border or edge of a lamina.
Figure 33A:
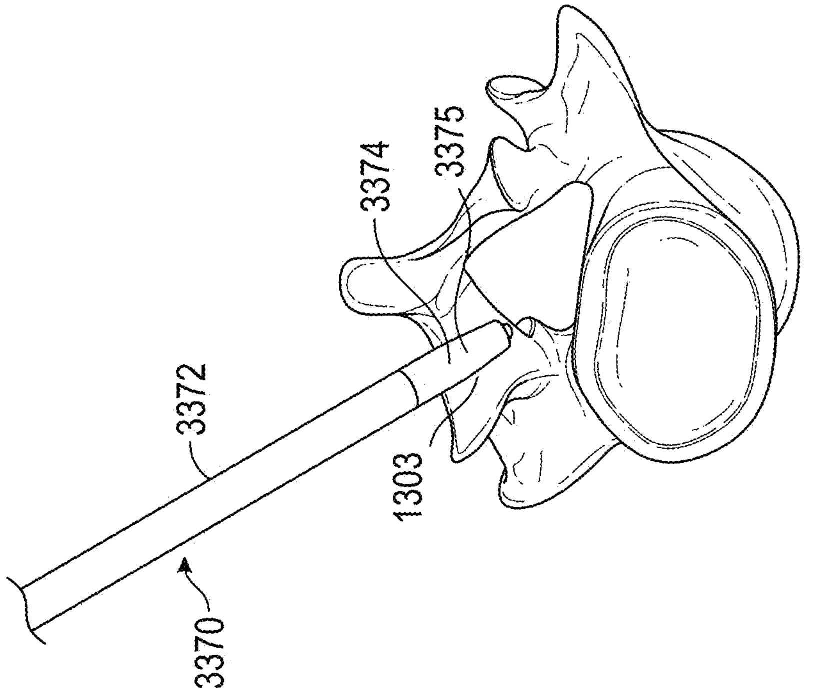
FIG. 33A shows an example of a reamer for decorticating bone.

FIG. 33A shows an embodiment of a reamer 3370 for decorticating bone. The reamer 3370 may be part of a system for laminectomy, laminotomy, or decompression.

Figure 33D:
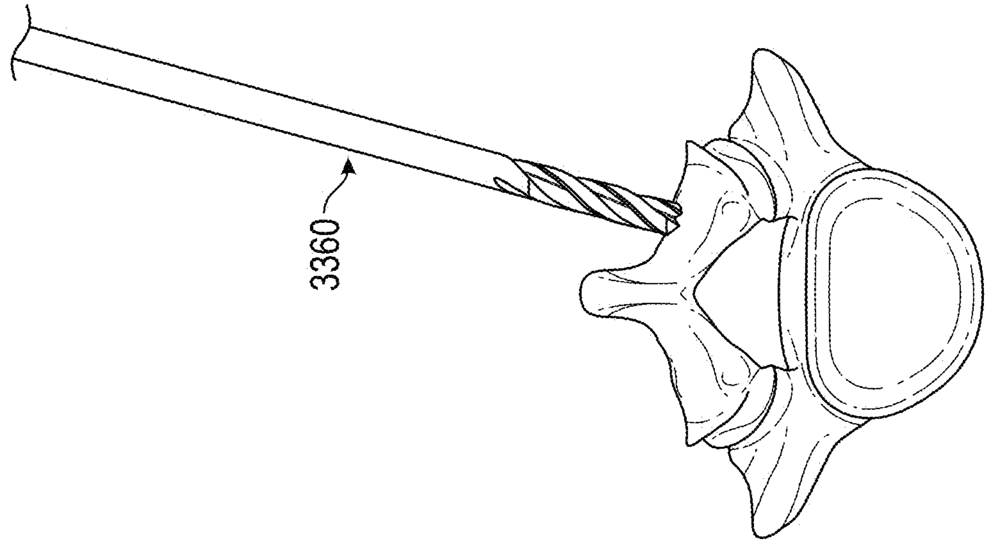
FIG. 33D shows the drill bit of FIG. 33B coming in from an inferior angle, somewhat parallel to the lamina aimed at the inferior border or edge of the lamina.

At least a portion of a distal tip or distal end 3374 of the reamer 3370 can include surface features, such as serrations or ribs, that can be used to decorticate overgrown bone and/or tissue. In some embodiments, surface features may extend only over a portion of the circumference of the distal end 3374 to limit the area being decorticated and avoid nerve damage or spinal cord damage. For example, in some embodiments, the distal end 3374 can include a smooth inferior surface 3375 to prevent nerve damage or spinal cord damage. In some embodiment, the distal end 3374 can be at least partially conical in shape to prevent nerve damage or spinal cord damage. The distal end 3374 can further include a serrated or ribbed superior surface 3377, as shown in FIG. 33F to decorticate overgrown bone and tissue. When a patient ages, spinal stenosis can shrink the spinal canal and overgrow bone and soft tissue. It can be difficult to gain access to the inferior border or edge of the lamina to create a laminotomy or remove bone from the lamina, which can create space for the nerve or spinal cord and decrease pain or dysfunction. By utilizing a reamer 3370 with a smooth inferior surface 3375, the user can decrease the risk of neural damage while creating access to the inferior border or edge of the lamina. In some examples, the smooth inferior surface 3375 can extend along the body 3372 of the reamer 3370. The distal most tip of the distal end 3374 can also be smooth, and the reamer 3370 can be tapered so that the user can enter the space around the target anatomy at a small diameter. As the reamer 3370 is advanced, the reamer 3370 can open up the space by rotating back and forth to shave the bone and disrupt the soft tissue. This can create a space for other instruments, for example instruments of the decompression systems described herein. The reamer 3370 can be advanced below the inferior edge of the lamina from an inferior position and can be advanced along the anterior surface of the lamina with the superior surface 3377 facing towards the anterior surface of the lamina and the smooth surface 3375 facing away from the anterior surface of the lamina. The reamer 3370 can be made from metal or other durable materials that resist breaking or falling apart.

FIG. 33B shows an embodiment of a drill bit 3360 drilling into the inferior border or edge of a lamina.

Other examples of laminotomies or laminectomies are performed using a posterior to anterior approach from a different direction. In examples of the methods described herein, a drill bit, pituitary, kerrison, or other instrument can be used to remove bone and soft tissue from an inferior approach.

Figure 33C:
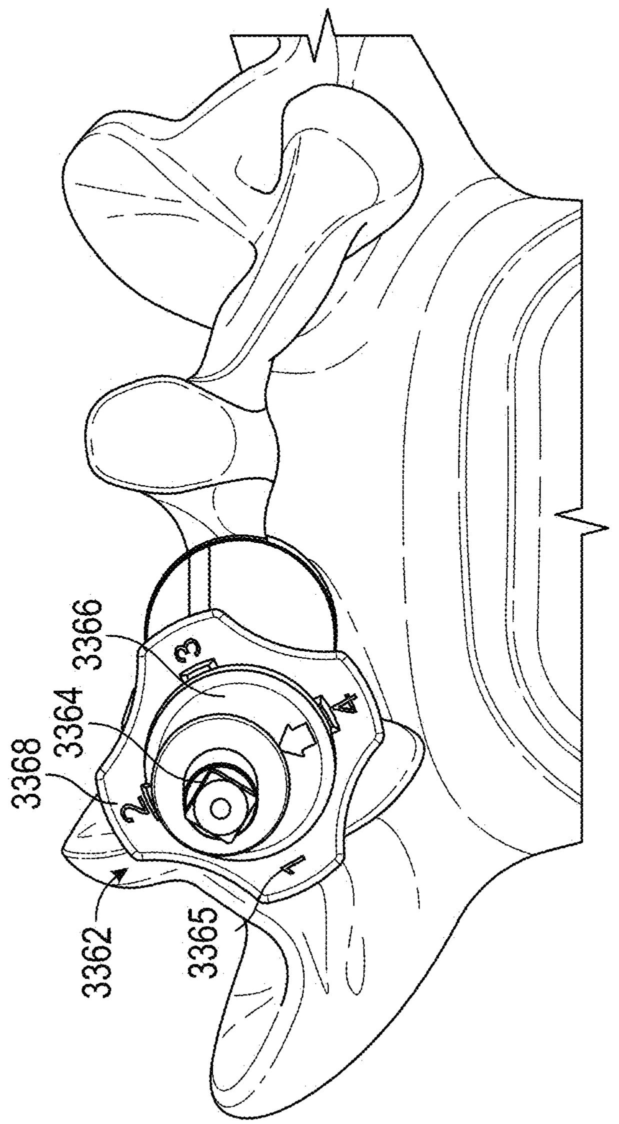
FIG. 33C shows a guide for a decompression system set up from an inferior approach, focused on the inferior border or edge of the lamina.
Figure 33F:
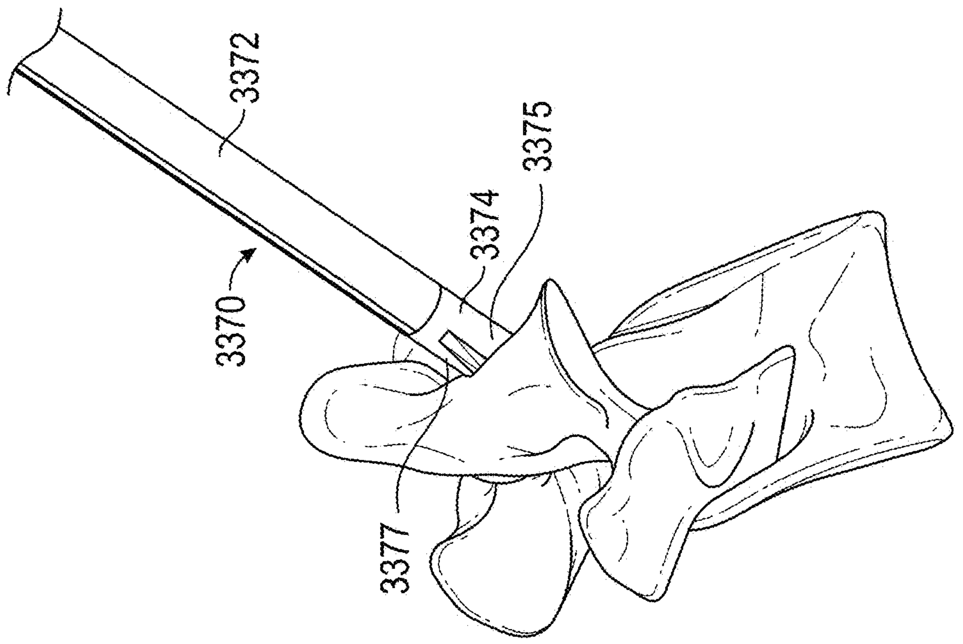
FIG. 33F shows a reamer with a serrated or ribbed area at the distal end.

FIG. 33C shows another embodiment of a guide 3362 for a decompression system. As shown in FIG. 33C, the guide is set up from an inferior approach, focused on the inferior border or edge of the lamina. The guide 3362 can include any of the same and/or similar features and/or functions as the guide 3050 and vice versa.

A drill or other bone removal device can be placed through the guide 3362 at a position of a plurality of positions to remove bone. As shown, the guide 3362 can include a plurality of markings 3365 to indicate alignment at different positions. In some embodiments, the markings 3365 can indicate a sequential arrangement for removing certain areas of bone before others. The markings 3365 may be pad printed, engraved, or another means of identifying the positions. In some embodiments, each marking 3365 on the guide 3362 can signify a different region of the target anatomy, so that a full laminotomy or laminate removal can be performed. In some embodiments, the markings can be in the form of numbers.

The guide 3362 can include a rotatable portion 3366 that can rotate with respect to a dial 3368. The dial 3368 of the guide 3362 has four positions identified via the markings 3365. In some examples, the dial 3368 of the guide 3362 can have 1-8 positions identified. In some examples, the dial 3368 of the guide 3362 can have 1, 2, 3, 4, 5, 6, 7, or 8 positions identified. Each position may be utilized, such that when instruments are used at every position, the entire procedure can be completed. In some examples, only certain positions are used to complete the procedure. In some examples, smaller drill bits or bone removal devices may be utilized at a higher number of positions. The instruments can be inserted into the aperture 3364 and lumen of the guide 3362. The position of the aperture 3364 and lumen with respect to the dial 3368 can change when the rotatable portion 3366 is rotated.

FIG. 33D shows the drill bit 3360 of FIG. 33B coming in from an inferior angle, somewhat parallel to the lamina aimed at the inferior border or edge of the lamina.

The angle of the drill bit 3360 may be directly pointed at the inferior edge 1301. The angle of the drill bit 3360 may come at an angle from plus or minus 5°, plus or minus 10°, plus or minus 15°, or plus or minus 20° relative to a plane of that bisects the inferior edge 1301 of the lamina between the posterior surface 1305 and the anterior surface 1303, depending on a patient's anatomy or the surgical approach that is needed to complete the lamina removal or decompression.

Figure 33E:
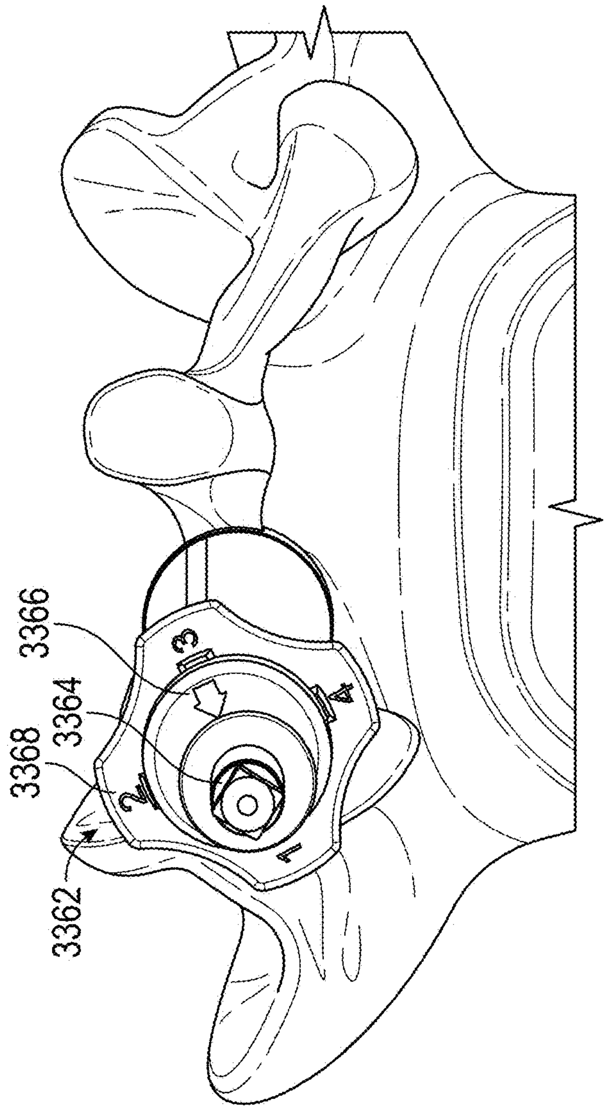
FIG. 33E shows the guide of FIG. 33C set up with the arrow on the rotatable portion 3366 aligned with the number three on the dial.

FIG. 33E shows the guide 3362 of FIG. 33C set up with the arrow on the rotatable portion 3366 aligned with the number three on the dial 3368.

The numbers on the dial 3368 can signify different regions of the lamina that may be removed to complete a laminotomy or lamina removal the amount of numbers may decrease or increase. In some examples, a user can perform the procedure with the arrow of the rotatable portion 3366 aligned with each of the numbers on the dial 3368 in order, for example from the first number to the last number. Depending on the level of the spine that is being operated on, such as L1, the procedure may require less positions of the guide 3362 being used. Less numbers can be used for L1 because the size of the lamina is smaller, and more numbers can be used for L5 because of the greater size of the lamina.

FIG. 33F shows a reamer 3370 with a serrated or ribbed area at the distal end 3374.

The reamer 3370 can go under the inferior border or edge of the lamina (e.g., adjacent anterior surface 1303) to open up the space and remove bone and/or soft tissue.

Figure 33G:
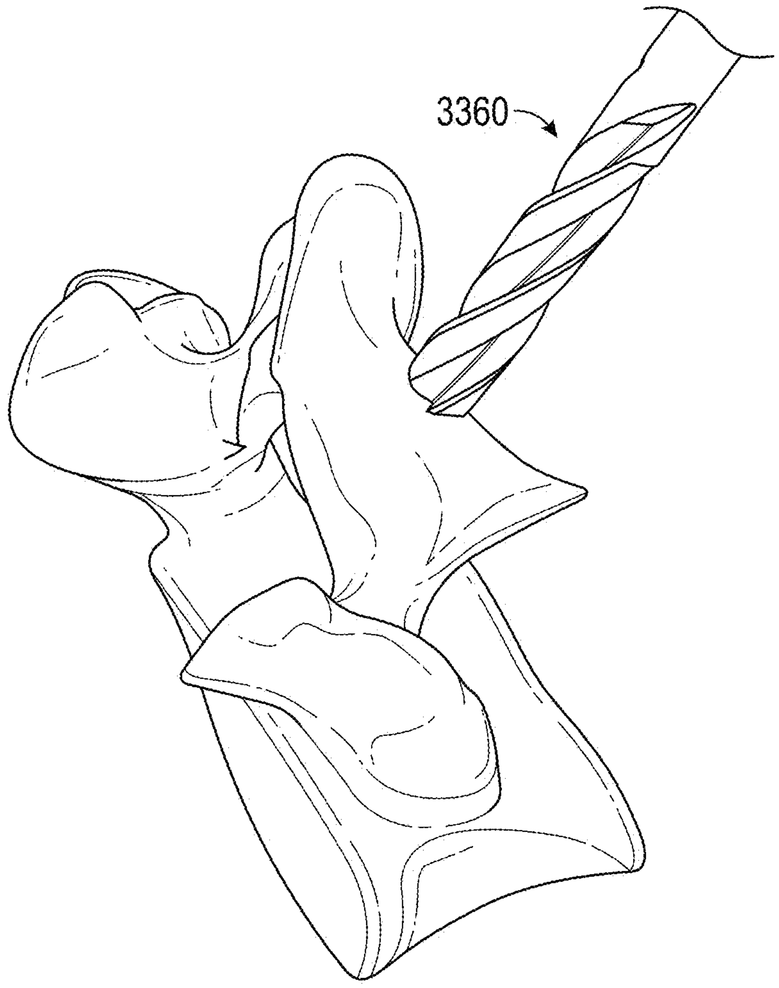
FIG. 33G shows the drill bit of FIG. 33B reaming along the inferior edge or border of the lamina.

FIG. 33G shows the drill bit 3360 of FIG. 33B reaming along the inferior edge or border of the lamina.

In some embodiments, the drill bit 3360 may approach the inferior border or edge of the lamina at an angle that is generally parallel with the lamina. In other embodiments, the drill bit 3360 can be positioned at an angle that is not a direct parallel angle of the inferior border or edge of the lamina. The drill bit 3360 or bone removal device may be angled at 20° or less (e.g., from a plane that bisects the edge of the lamina between the posterior and anterior surfaces). In some examples, the drill bit 3360 or bone removal device may be angled at 10° or less (e.g., from a plane that bisects the edge of the lamina between the posterior and anterior surfaces). In some examples, the drill bit 3360 or bone removal device may be angled at 30° or less (e.g., from a plane that bisects the edge of the lamina between the posterior and anterior surfaces).

Figure 34B:
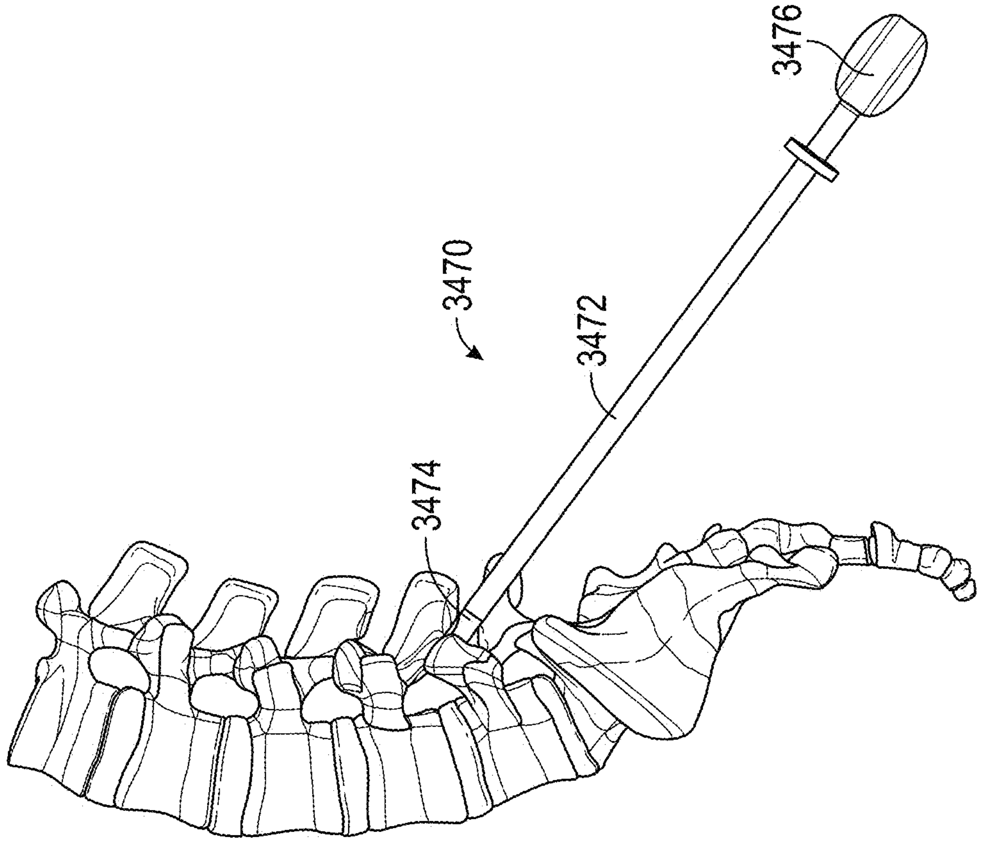
FIGS. 34A and 34B show the reamer underneath the inferior edge or border of the lamina removing bone and soft tissue to make room for the decompression system.
Figure 34A:
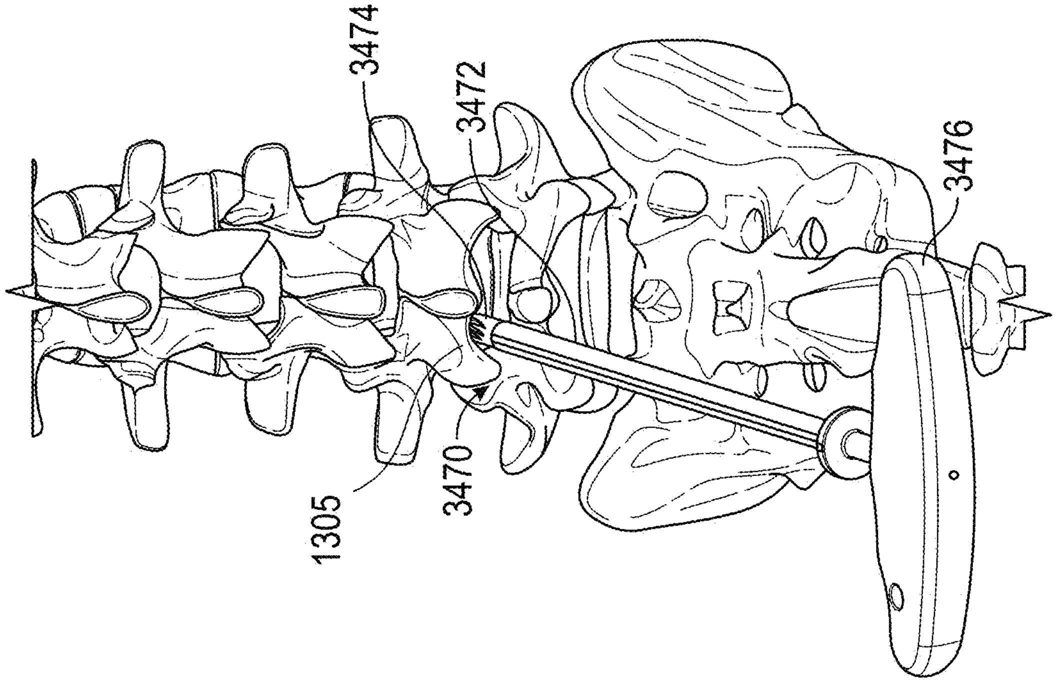
Figure 34C:
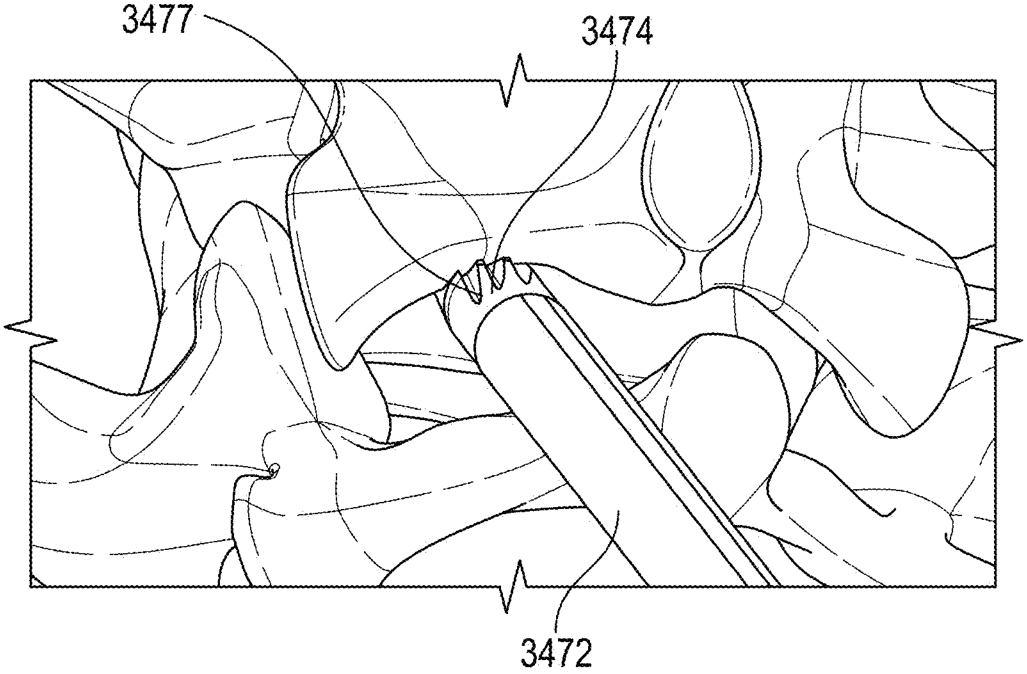
FIGS. 34C and 34D show the reamer of FIG. 34A underneath the inferior border edge of the lamina.
Figure 34D:
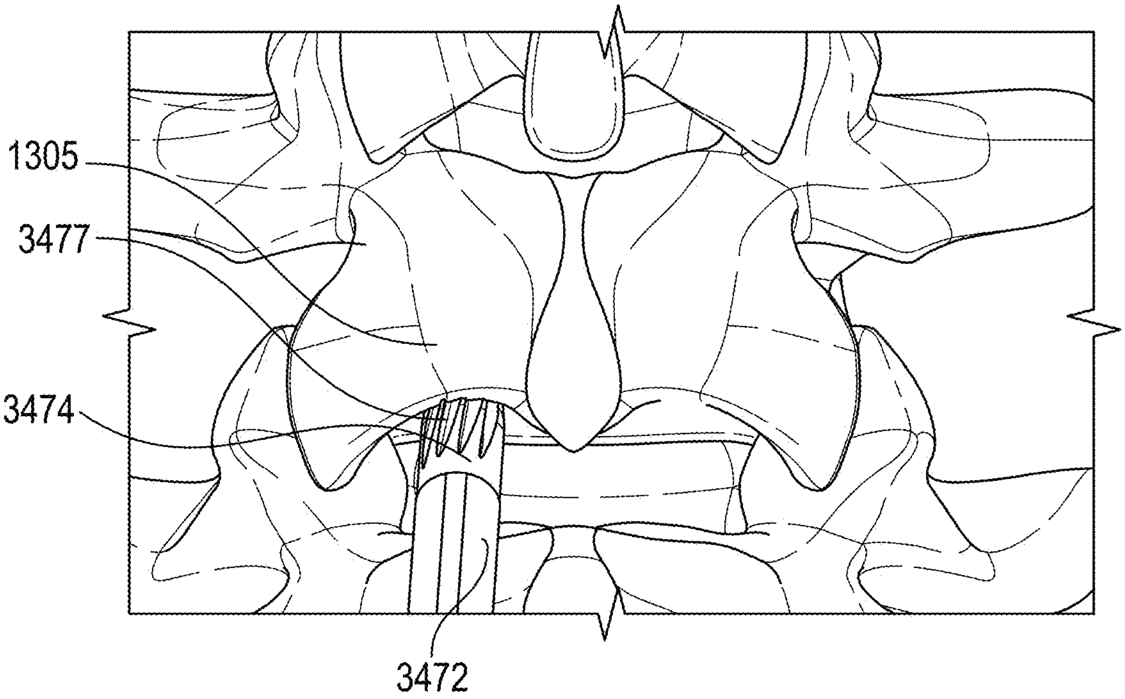
Figure 35A:
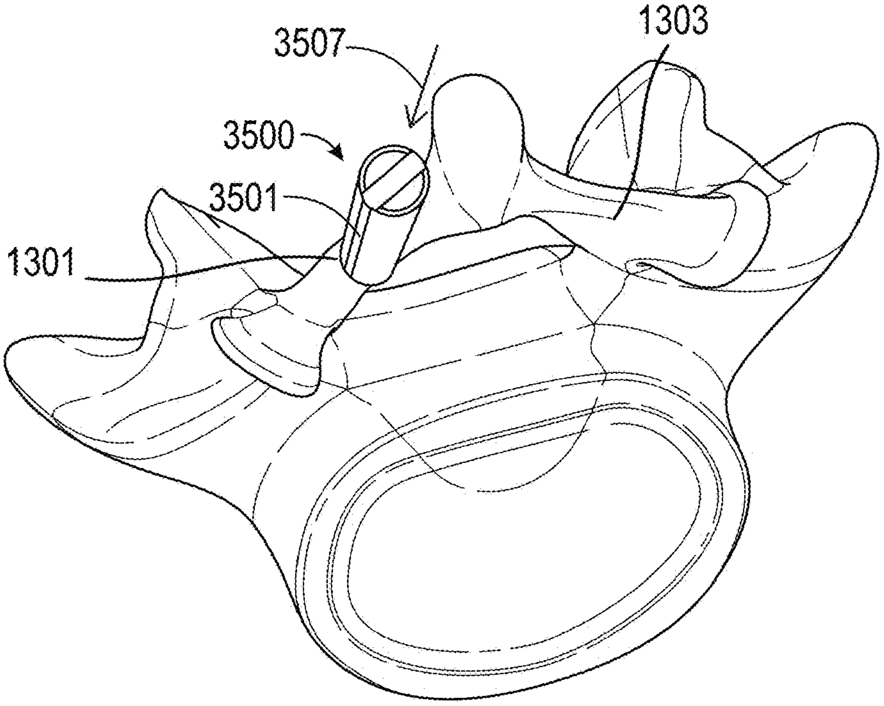
FIG. 35A shows an example of a laminar locator.

FIGS. 34A and 34B show the reamer 3470 underneath the inferior edge or border of the lamina removing bone and soft tissue to make room for the decompression system. FIGS. 34C and 34D show the reamer 3470 of FIG. 34A underneath the inferior border or edge of the lamina (e.g., adjacent the anterior surface 1303).

The reamer 3470 can include any and/or all the features of the reamers described with respect to FIGS. 33A-33G. The reamer 3470 may be attached to a handle 3476. In some examples, the handle 3476 may be a stationary handle or a monolithic handle. In some examples, the handle 3476 may be T handle or straight handle, or any other shape that can help maneuver or force the reamer 3470 into the space underneath the inferior edge or border of the lamina and allow for it to grind the bone and soft tissue by rotating it back and forth. The serrated edge or sharp edges of the distal end 3474 can be on the superior surface 3477 of the reamer to remove the bone and soft tissue. The inferior side of the body 3472 and/or distal end 3474 may be smooth to prevent neural injury. The serrated or sharp superior surface 3477 can include around 75% of the surface area of the distal end 3474 of the reamer 3470. The superior surface 3477 can face the anterior surface 1303 of the lamina from a position anterior to the lamina. In some examples, the serrated or sharp superior surface 3477 can include around 50% to 100% of the surface area of the distal end 3474 of the reamer 3470. In some examples, the serrated or sharp superior surface 3477 can include around 10% to 100% of the surface area of the distal end 3474 of the reamer 3470. Advantageously, less surface area that is serrated or sharp can help prevent nerve damage.

The body 3472 and/or the distal end 3474 of the reamer 3470 can be moved toward the lamina from under the lamina. The distal end 3474 of the reamer 3470 can enter the inferior edge or border and go up to the middle anterior surface of the lamina to debride and remove bone and soft tissue.

Figure 35B:
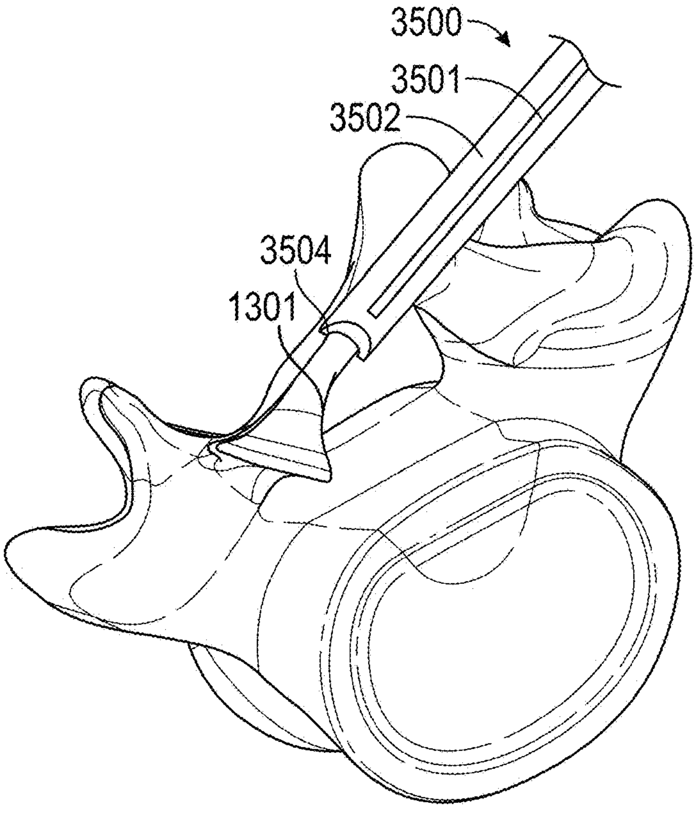
FIG. 35B shows the laminar locator of FIG. 35A docked on the inferior portion of the lamina.
Figure 35C:
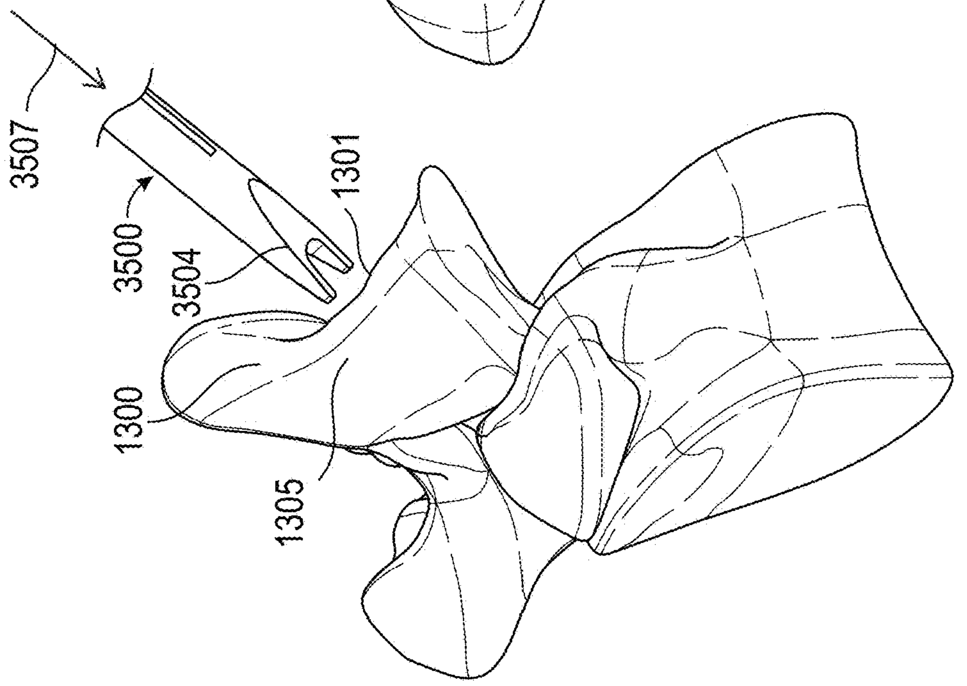
FIG. 35C shows the laminar locator of FIG. 35A before it is placed on the inferior border or edge of the lamina.
Figure 35D:
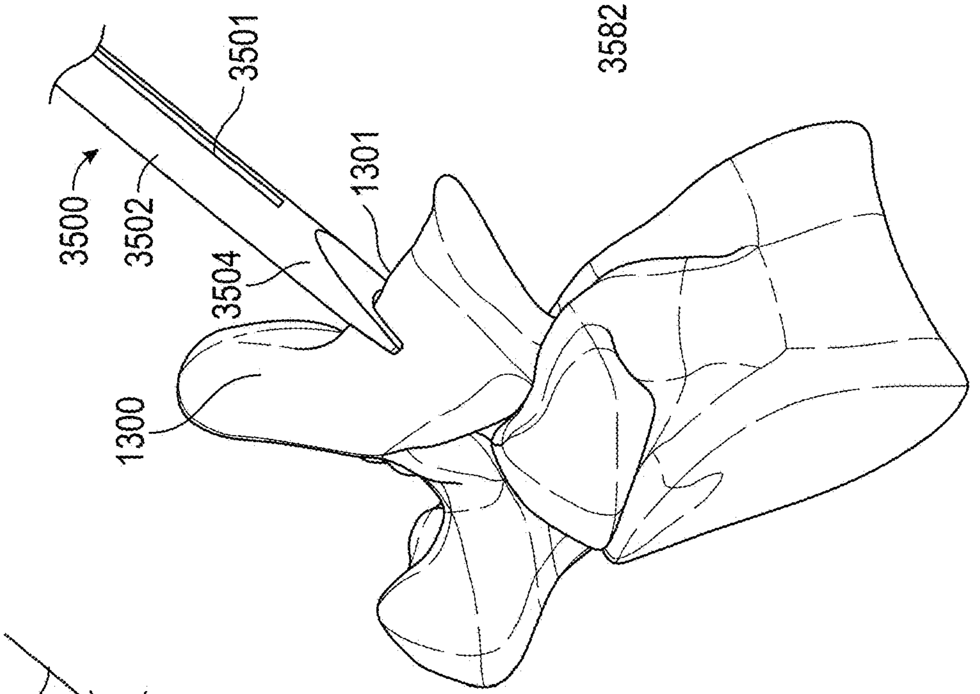
FIG. 35D shows the lamina locator of FIG. 35A docked on the inferior border or edge of the lamina.
Figure 35E:
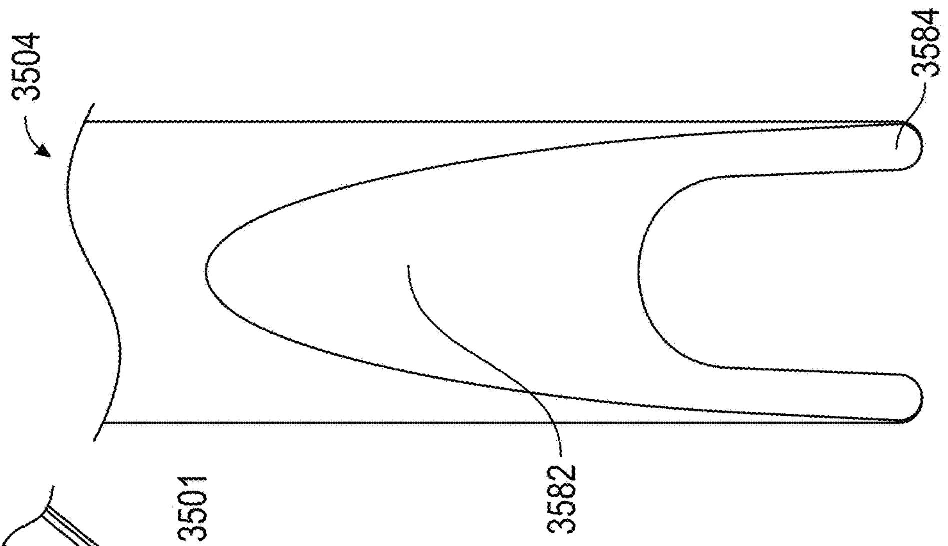
FIG. 35E shows the distal end of the lamina locator of FIG. 35A.

FIG. 35A shows another embodiment of a laminar locator 3500. FIG. 35B shows the laminar locator 3500 of FIG. 35A docked on the inferior edge of the lamina. FIG. 35C shows the laminar locator 3500 of FIG. 35A before it is placed on the inferior border or edge 1301 of the lamina. FIG. 35D shows the lamina locator 3500 of FIG. 35A docked on the inferior border or edge 1301 of the lamina. FIG. 35E shows the distal end 3504 of the lamina locator 3500 of FIG. 35A.

The laminar locator 3500 can include any of the same and/or similar features and/or functions as the laminar locator 2800. The laminar locator 3500 can include a line 3501 on a proximal portion of the instrument to show an orientation (e.g., a rotational position about a longitudinal axis) of the laminar locator 3500 to the user. This can allow a user to know which way the lamina locator 3500 is docking on the inferior portion or edge 1301 of the lamina. In some examples, the line 3501 can run down the length of the laminar locator 3500. For example, the body 3502 of the laminar locator 3500 may have lines 3501 on the side that are laser etched or notched to show the user the orientation of the distal end of the lamina locator 3500 if the instrument is buried in the patient's tissue. In some embodiments, the line may indicate an angular orientation of the lamina.

As shown in FIG. 35B, once docked, the laminar locator 3500 can prevent movement, and allow for other instruments to advance over the laminar locator to the position desired. The laminar locator 3500 can have a U-shaped design at the distal end 3504 that can engage the inferior surface or edge 1301 of the lamina, for example, as described with respect to the laminar locator 2800. The laminar locator 3500 can be blunt or sharp at the edges of the distal end 3504. In some examples, a sharp end of the laminar location 3500 can be moved back-and-forth to remove soft tissue to allow docking on the lamina. In some examples, each side of the distal end 3504 may be tapered and come to an edge to allow it to become sharp. In some examples, the distal end 3504 can be blunt, which can minimize injury if the instrument is accidentally passed through the interlaminar space between the lamina and the spinal cord.

In some examples, fluoroscopy can be used to place the laminar locator 3500 in the appropriate position. In some examples, a larger incision may be made, and the anatomy may be directly visualized, and the laminar locator 3500 placed directly on the inferior edge or border of the lamina.

Other instruments can be passed over the laminar locator 3500 safely so there is no migration. The other instruments may be placed in their appropriate positions over the laminar locator 3500. The laminar locator 3500 can be the first instrument that is passed through the muscle skin and other soft tissue during the procedure. The laminar locator 3500 may be made of metal or other durable, plastics, or surgical materials that are strong enough to withstand passing through tissue and muscle. The laminar locator 3500 may be made of materials that allow for docking on the inferior edge or border of the lamina.

As shown in FIG. 35E, the distal end 3504 can be U-shaped to hug or dock on the inferior lamina border. The distal end 3504 can include an angled or beveled surface 3582 on one or both sides of the distal end 3504. The distal end 3504 can include two prongs 3584 extending distally. One of the prongs may engage a posterior surface of the lamina while the other prong engages the anterior surface of the lamina. The edge of the lamina may be received between the two prongs 3584. The prongs 3584 may be blunt to prevent injury, or may be manufactured as sharp to pierce muscle and soft tissue. The beveled surface 3582 can streamline tissue passing by the instrument. At the base of the arch of the distal end 3504, the beveled surface 3582 can remove bone when swiped side to side, acting as a blade.

Figure 36A:
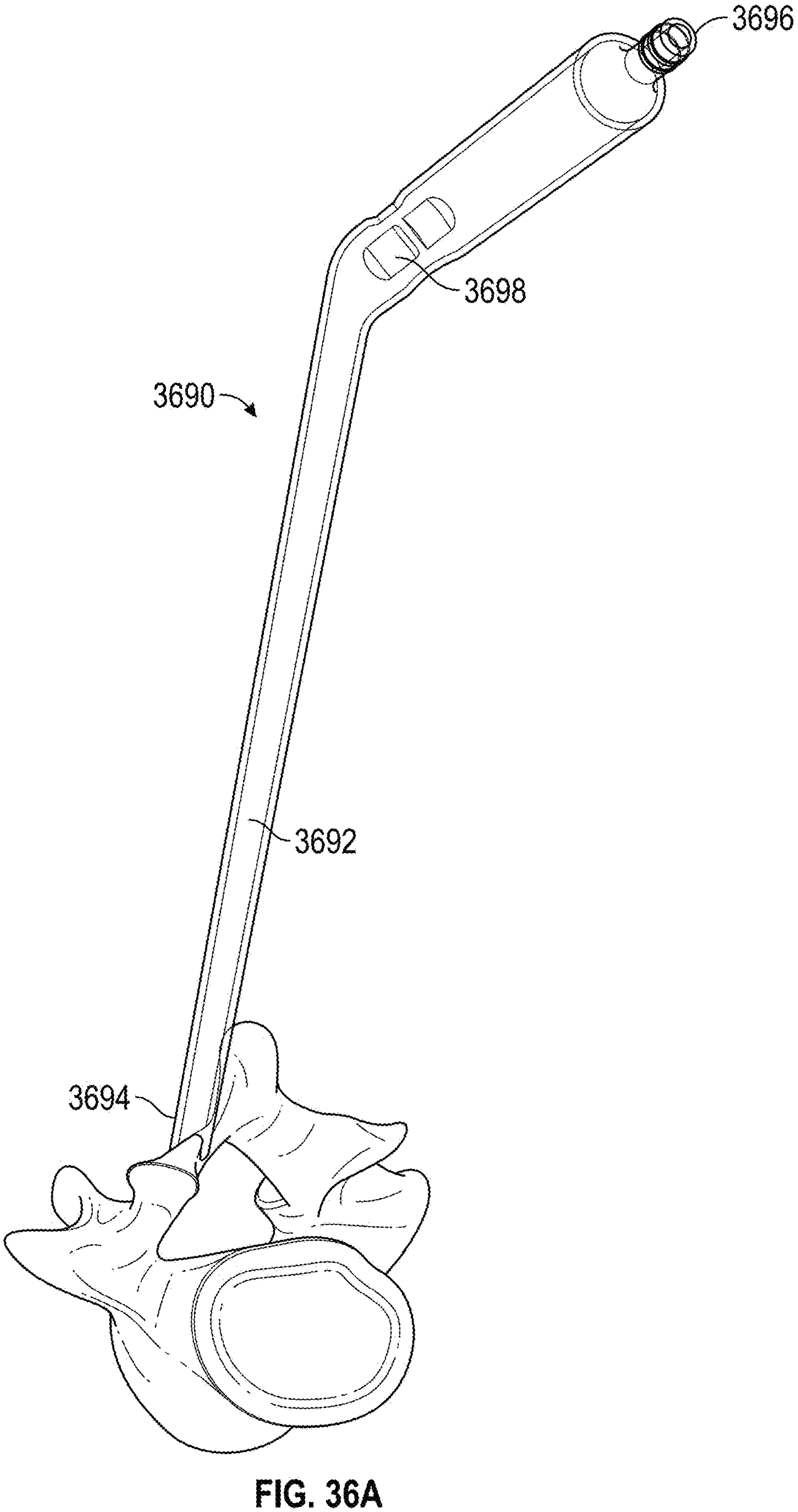
FIG. 36A shows a suction tube to evacuate or clean bone from using a drill, Kerrison, or pituitary.
Figure 36B:
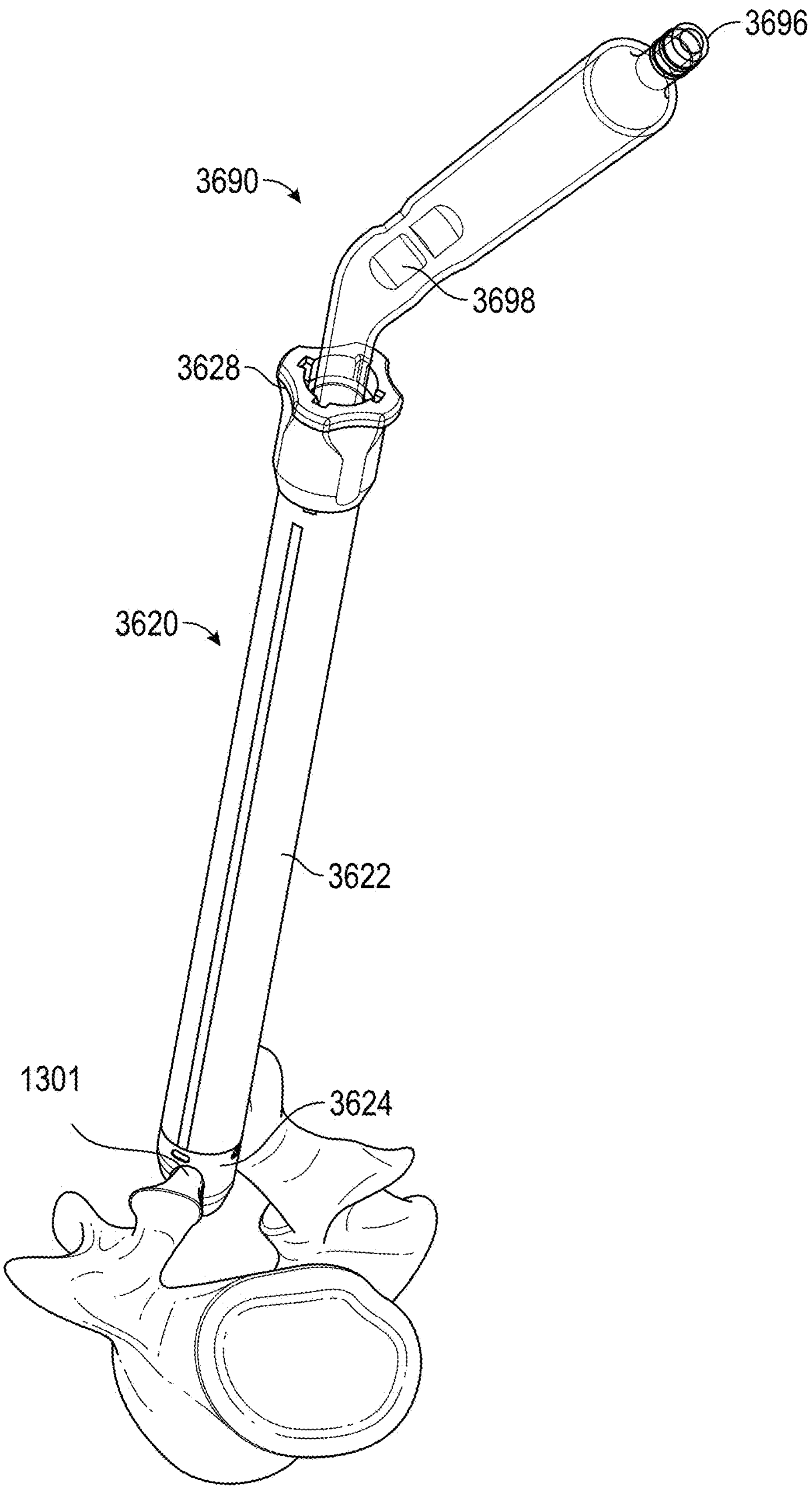
FIG. 36B shows the distal end of the suction tube being positioned in an outer cannula to remove bone fragments or dust out of a canal region in which a laminotomy or lamina removal has been performed.

FIG. 36A shows an embodiment of a suction tube 3690 to evacuate or clean bone from using a drill, Kerrison, or pituitary. FIG. 36B shows the distal end 3694 of the suction tube 3690 being positioned in an outer cannula 3620 to remove bone fragments or dust out of a canal region in which a laminotomy or lamina removal has been performed.

There may be fragments left in a cannula that can be removed utilizing a suction tube 3690. The suction tube 3690 may be disposable or made of polymer or metallic. The suction tube 3690 may be featured in the disposable kit with other instruments. The suction tube 3690 may come in different designs, such as Yankauer or Frazier style. The suction tube 3690 may come in other geometric shapes and angles. The suction tube 3690 may include a narrow proximal end 3696, for example for connecting to a suction source (e.g., a vacuum pump). The suction tube 3690 may include indentations 3698 along the body 3692. The suction tube 3690 may have a distal end 3694, or suction tip, sized and shaped to fit in a target area, for example a removed portion of a lamina. If bone is left in the spinal canal region it could cause trauma or pain.

As shown in FIG. 36B, the suction tube 3690 can be positioned within the cannula 3620. The cannula 3620 can include any and/or all of the features of cannulas described with respect to FIGS. 28A-28H. For example, the cannula 3620 may have a distal end 3624, a body 3622, indents 3626, and/or a cap 3628.

The vertebrae between the lower thoracic spine and the upper lumbar spine are smaller than other vertebrae and do not require as large of a recess to be formed for a laminotomy. For such vertebrae (e.g., L2 and L3) the procedures described herein may be performed without using a separate cannula and guide. Instead, the cannula may function as a guide by allowing instruments to pass therethrough. In some embodiments, the procedures described herein may be performed without having a separate dilator and cannula. For example, in some embodiments, the cannula may operate as the dilator or vice versa. In some embodiments, a single instrument (e.g., a dilator or cannula) may operate as the dilator, cannula, and guide as described herein. For example, a laminar locator may be docked to the lamina, and the single dilator or cannula may be advanced over the lamina locator to provide for dilation and to provide a lumen for one or more instruments to be advanced through for removal of bone.

Figure 37A:
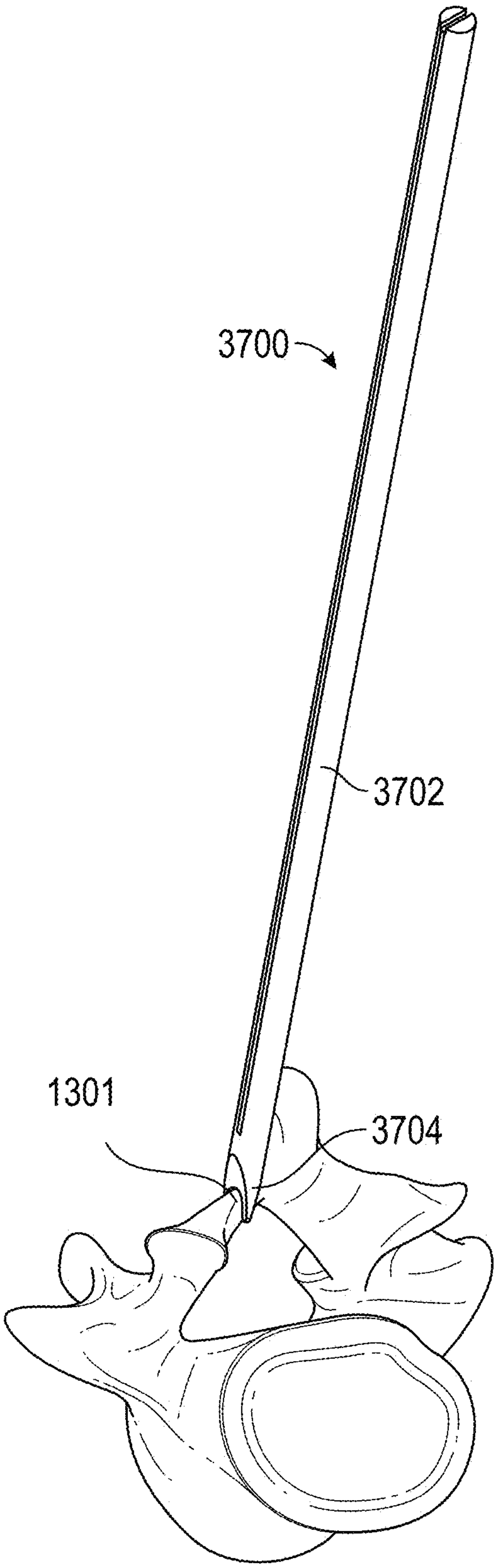
FIG. 37A shows an example of the laminar locator.
Figure 37B:
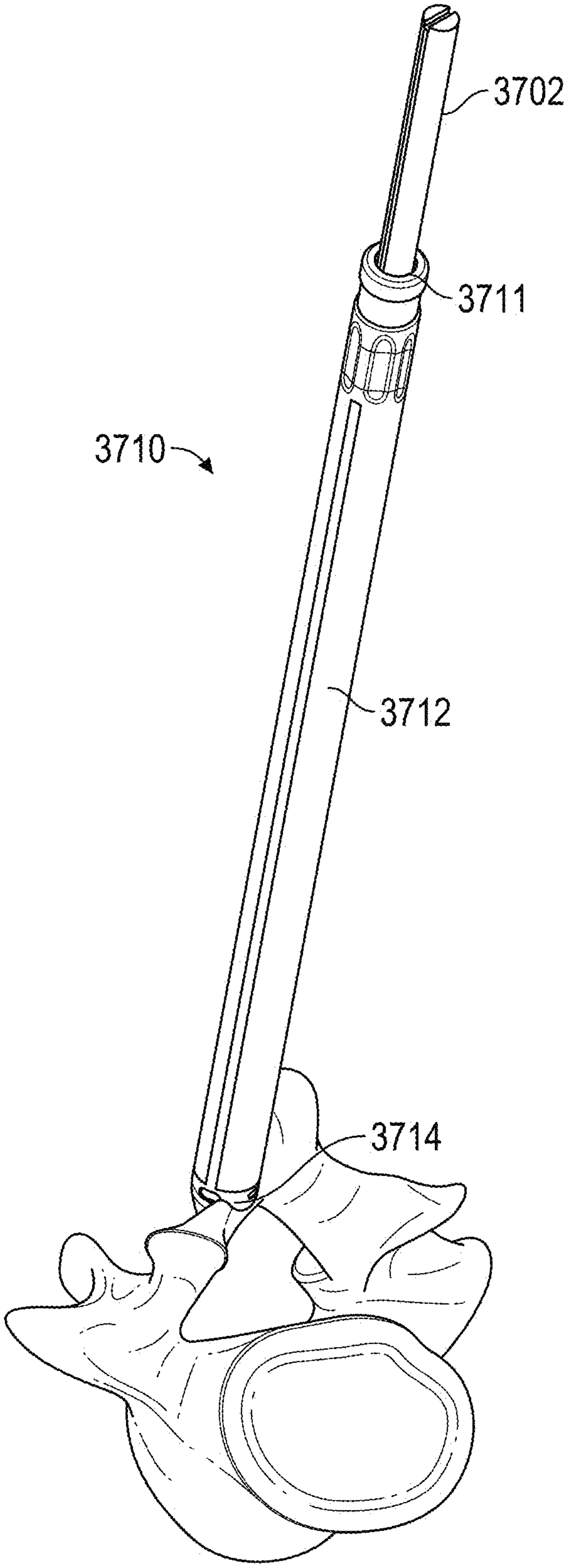
FIG. 37B shows a dilator that is passed over the lamina locator of FIG. 37A.
Figure 37C:
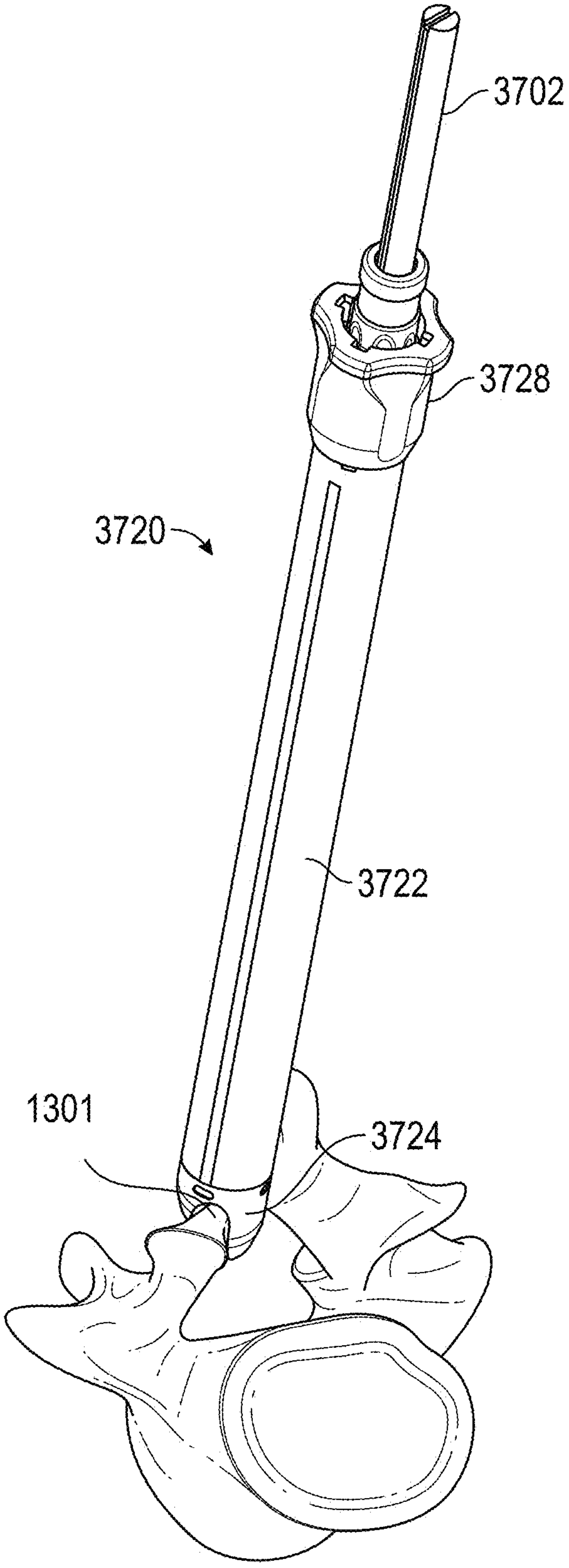
FIG. 37C shows a cannula passed over the dilator of FIG. 37B.

FIGS. 37A-37C show an example procedure in which instruments are advanced to the target anatomy through a cannula 3720 without using a guide 3050 or guide 3362.

Figure 37D:
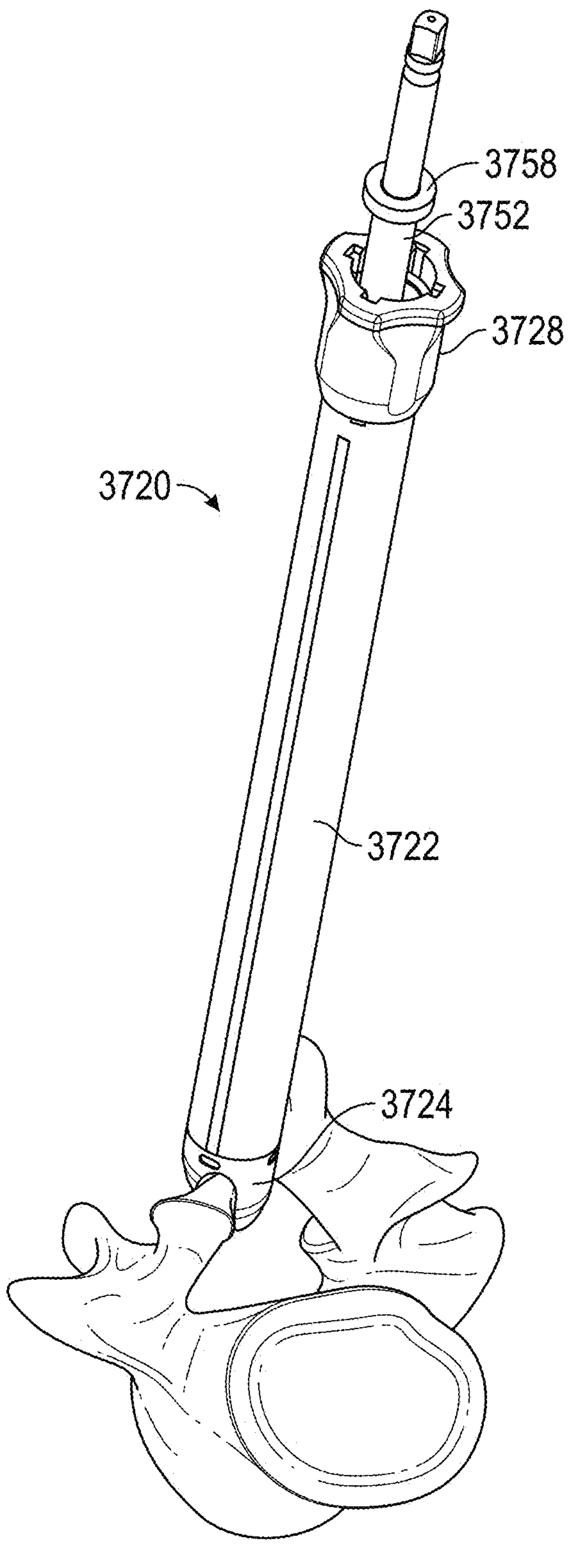
FIG. 37D shows a drill bit positioned in the cannula and the outer cannula of FIG. 37C.

FIG. 37A shows the laminar locator 3700 docket at the target anatomy. FIG. 37B shows a dilator 3710 that is positioned over the lamina locator 3700 of FIG. 37A. FIG. 37C shows a cannula 3720 positioned over the dilator 3710 of FIG. 37B. FIG. 37D shows a drill bit 3752 positioned in the cannula and the 3720 outer cannula of FIG. 37C.

In certain embodiments, the laminar locator 3700 can be advanced to and docket to the target anatomy as shown in FIG. 37A. The dilator 3710 can be advanced over the laminar locator 3700 as shown in FIG. 37B. The cannula 3720 can be advanced over the dilator 3710 as shown in FIG. 37C. The laminar locator 3700 and dilator 3710 can then be removed from the cannula 3720, and the drill bit 3752 can be advanced through the cannula 3720 to the target anatomy actuated to drill bone. The drill bit 3752 can have a drill stop 3758 configured to contact the cannula 3720.

The laminar locator 3700 can include any of the same or similar features and/or functions as any of the laminar locators described herein and vice versa. The laminar locator 3700 can be aimed at the inferior border or edge of the lamina. The laminar locator 3700 can have a U-shaped at the distal end that is meant to engage or dock on the inferior border of the lamina. The laminar locator 3700 can prevent migration of instruments from the target surgical site. The laminar locator can include a body 3702. The laminar locator 3700 can have a U-shape, V-shape, or other shape at the distal end 3704 that allows for anchoring or docking safely on the inferior border or edge of the lamina. The laminar locator 3700 may be made of metal, plastic, polymer, or a combination thereof. Once the laminar locator 3700 is docked safely, other instruments may be passed over to the target surgical site.

The dilator 3710 can include any of the same or similar features and/or functions as any of the dilators described herein. The dilator 3710 may be plastic, metal, polymer, or a combination thereof. The dilator 3710 may be disposable or autoclavable. The dilator 3710 may include a metallic distal end 3714. The dilator 3710 can have a lumen 3711 extending therethrough. The dilator 3710 may include a polymer-based distal end 3714 to allow for imaging during surgery. A metallic distal end 3714 may allow for visualization when docking. The dilator 3710 may include a guard on each side of the distal end 3714 to allow for safe passing of the instrument. A bottom guard of the distal end 3714 can be longer than the top guard to hug the lamina and prevent migration of the instrument. The dilator 3710 may also be flat at the distal end 3714 without protrusions if necessary. The dilator 3710 may have top and the bottom protrusions of the same length. The body 3712 and/or distal end 3714 may be rounded and circular or nearly circular around its circumference and within the instrument. There may be more than one dilator 3710 to accommodate a dilation tube. There may be 1, 2, 3, or 4 dilation tubes depending on how much tissue needs to be dilated.

As shown in FIG. 37C, a cannula 3720 can be placed over the dilator 3710. The cannula 3720 can be an outer dilator. The cannula 3720 can include any of the same or similar features and/or functions as any of the cannulas described herein and vice versa. The cannula 3720 may be made of metal, polymer, or a type of durable medical plastic. The cannula 3720 may be comprised of one material or two materials, for example with a metallic distal end 3724 in plastic tube forming the body 3722. The cannula 3720 with a metallic distal end 3724 can allow the user a better visualization in surgery, yet still allow for visualization under fluoroscopy. The metallic distal end 3724 can allow for durability when placing over the lamina. An inferior portion of the distal end 3724 can be longer than the superior portion of the extended protrusions. The inferior protrusion can act as a guard to prevent spinal cord injury when drilling or removing bone from the lamina. The inferior protrusion may engage the anterior surface of the lamina and the superior protrusion may engage the posterior surface of the lamina. The drill bit can be positioned proximal to the distal end of the guard. In some examples, a drill bit may be placed directly through the cannula 3720, which can act as a guide. In some examples, an internal instrument guide may not be utilized. For example, in the upper lumbar or lower thoracic spine, an inner guide may not be needed, and the user may drill directly through the outer cannula 3720. A single drill bit hole, Kerrison, or pituitary may be utilized or needed to create a lamina defect or laminotomy to provide relief to the patient. The cap 3728 can be an adjustable portion of the cannula allow control of the drill bit or other bone removal device. The cap 3728 can act as a depth stop to allow a user to create a larger deeper defect when adjusted. The cap 3728 may be moved or operated by twisting, snapping, sliding, or other means of operation.

Figure 38A:
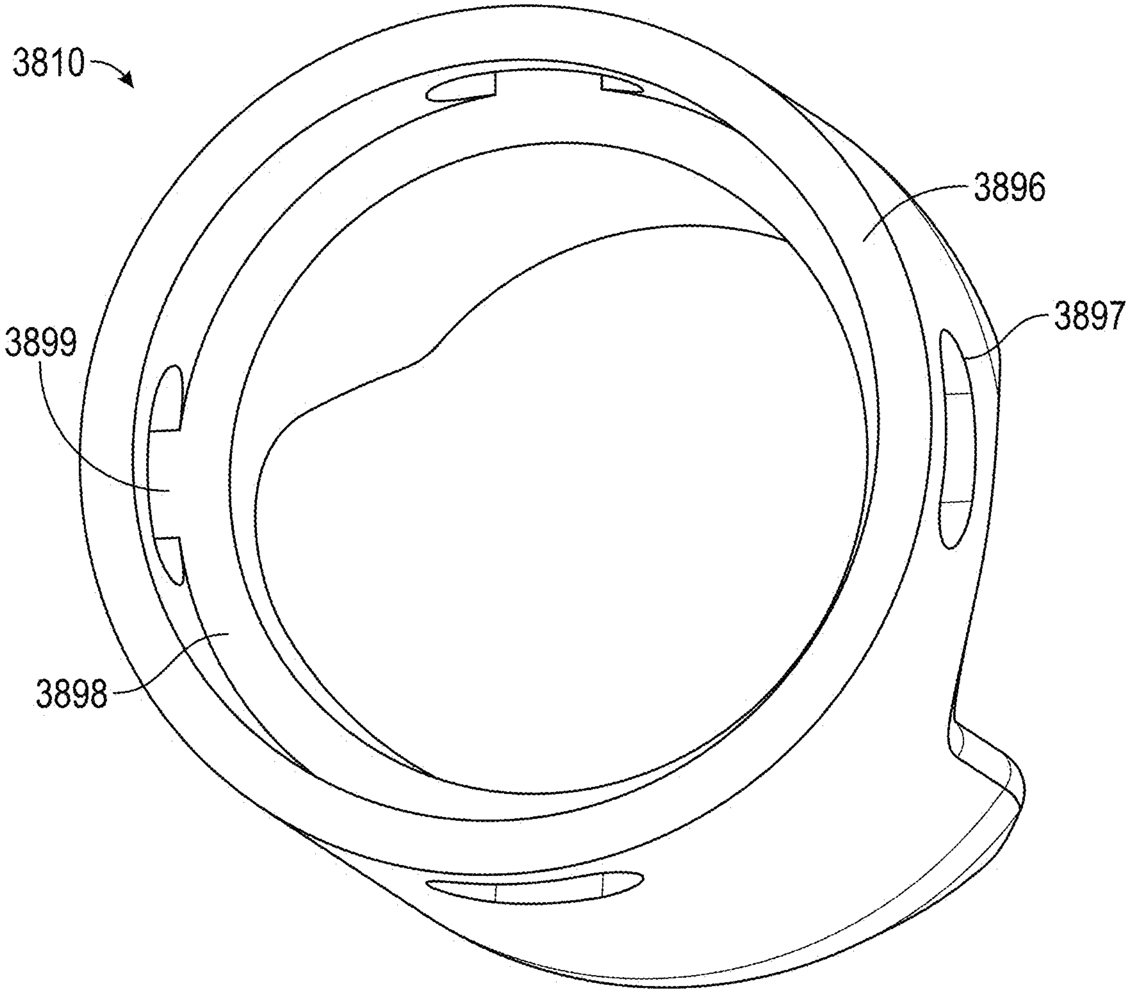
FIGS. 38A and 38B show an example of a distal end of a cannula.
Figure 38B:
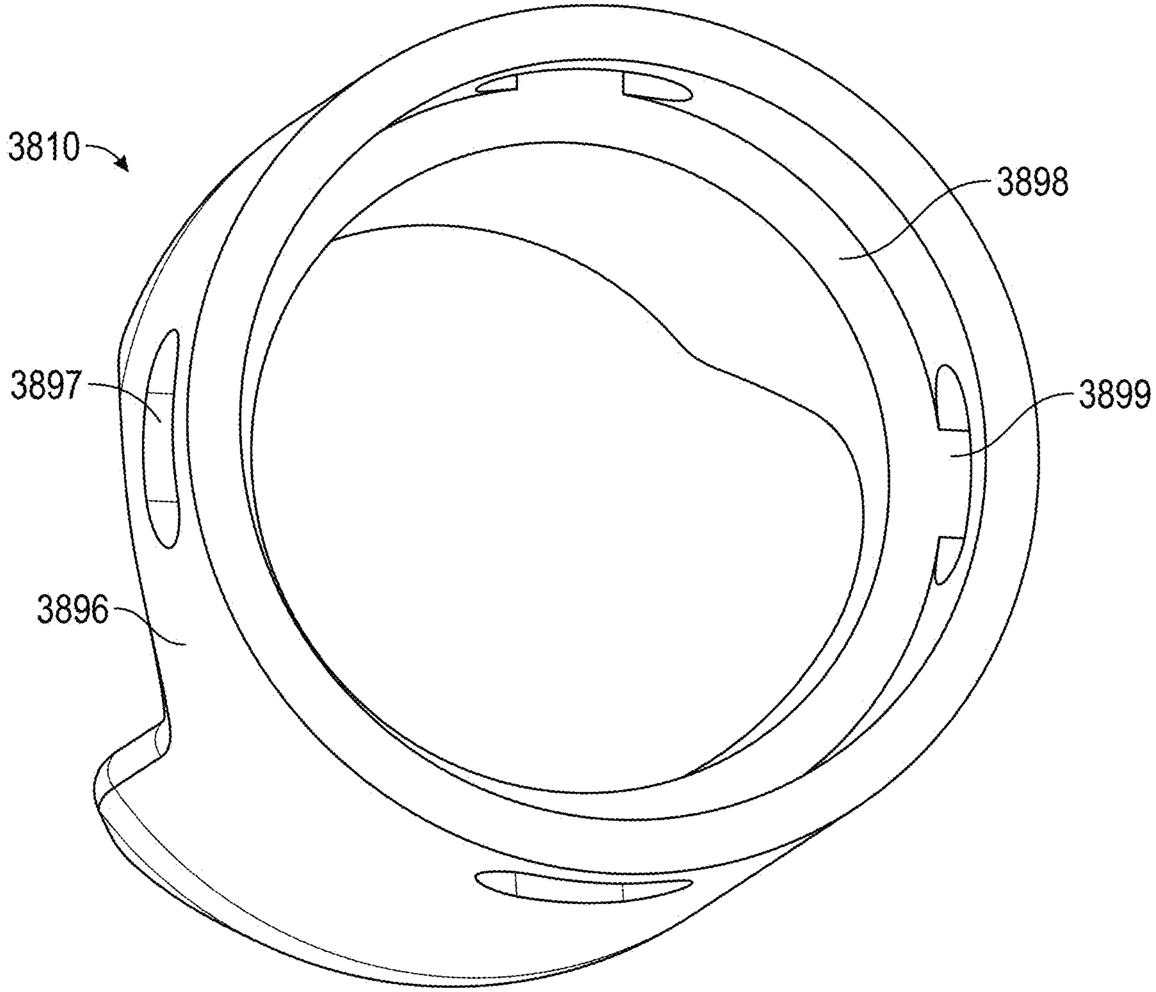

FIGS. 38A and 38B show an embodiment of a distal end of a cannula 3810. The cannula 3810 may act as an outer dilator and/or instrument guide (e.g., in procedure in which a separate instrument guide is not used). The cannula 3810 may include any of the same or similar features and/or functions as any of the other cannulas described herein and vice versa. In some embodiments, a guide may include a distal end that is the same as and/or similar to the distal end of the cannula 3810.

The distal portion of the cannula 3810 can be metallic. The distal portion of the cannula 3810 may be over molded into plastic or other polymer. In some embodiments, the distal portion includes a metallic outer portion 3896 and a plastic internal portion 3898. The internal portion 3898 and/or the outer portion 3896 can be cylindrical. The outer portion 3896 can have holes 3897 where the over molded plastic portions 3899 flow into to prevent a disjunction of the metallic piece or the plastic piece. The outer portion 3896 can have a distal portion that extends out and acts as a guide to prevent spinal cord or nerve damage.

Figure 38C:
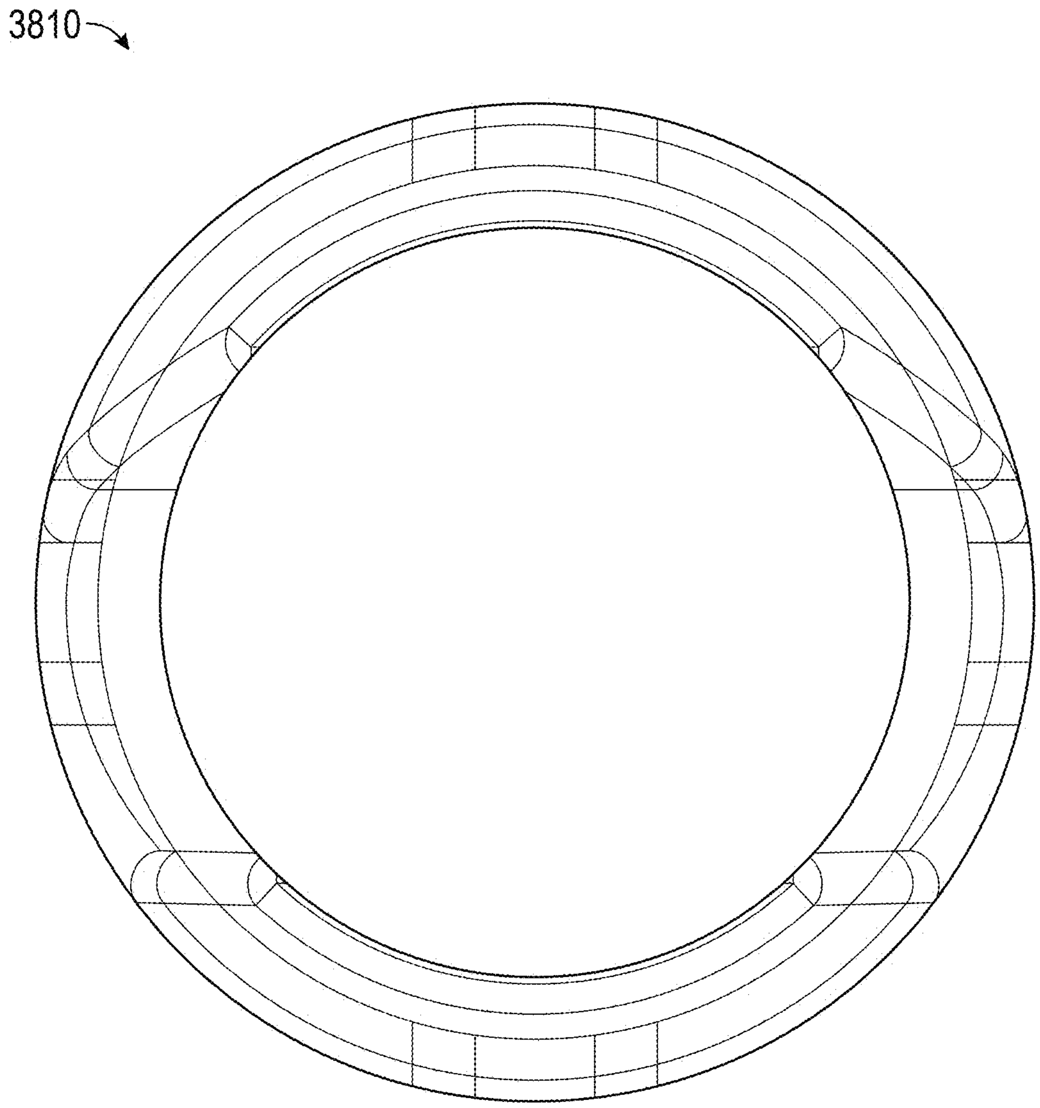
FIG. 38C shows a front view of the cannula.

FIG. 38C shows a front view of the cannula 3810. As shown in FIG. 38C, the lumen of the cannula can be circumferential. Similarly, the lumen of an instrument guide or dilator as described herein can be circumferential.

Figure 38D:
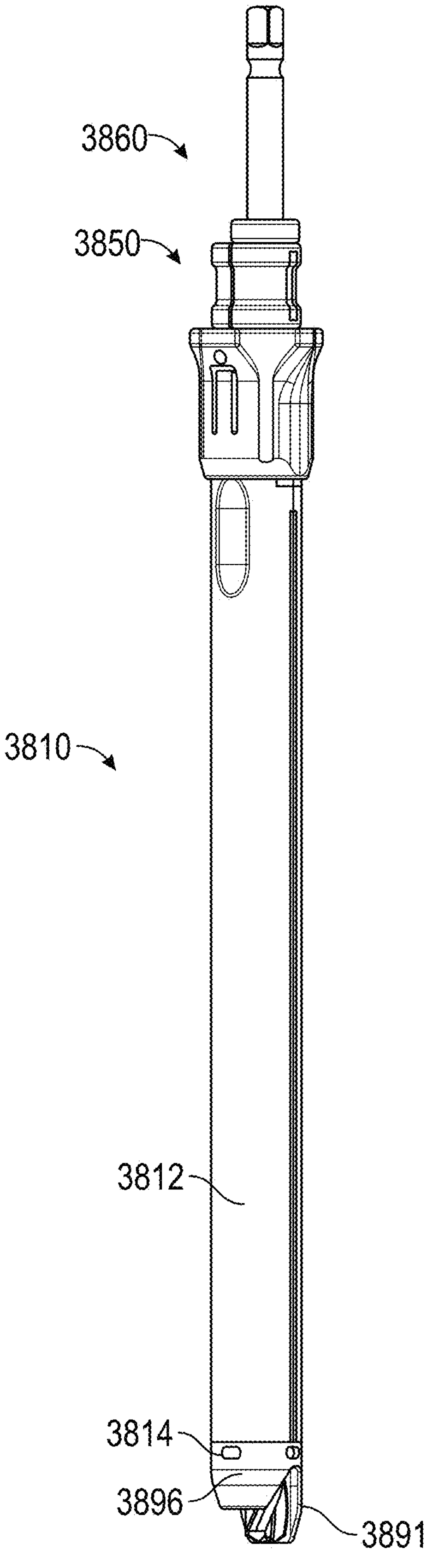
FIG. 38D shows the cannula, a guide, and a drill bit placed through the guide.

FIG. 38D shows the cannula 3810 with a guide 3850 positioned therein, with a drill bit 3860 placed through the guide.

The cannula 3810 can include a body 3812. The drill bit 3860 can extend through the guide 3850 or through the cannula 3810 if a guide 3850 is not used. In some examples, when positioned as distally as possible, the drill bit 3860 may not extend further than the bottom guard on the distal end 3814 of the cannula 3810 or instrument guide 3850. A user can safely drill until the positive stop on the drill bit 3860 contacts a proximal portion or another bone removing device is used. Advantageously, the dimensions can minimize the risk of spinal cord or nerve damage.

Figure 38E:
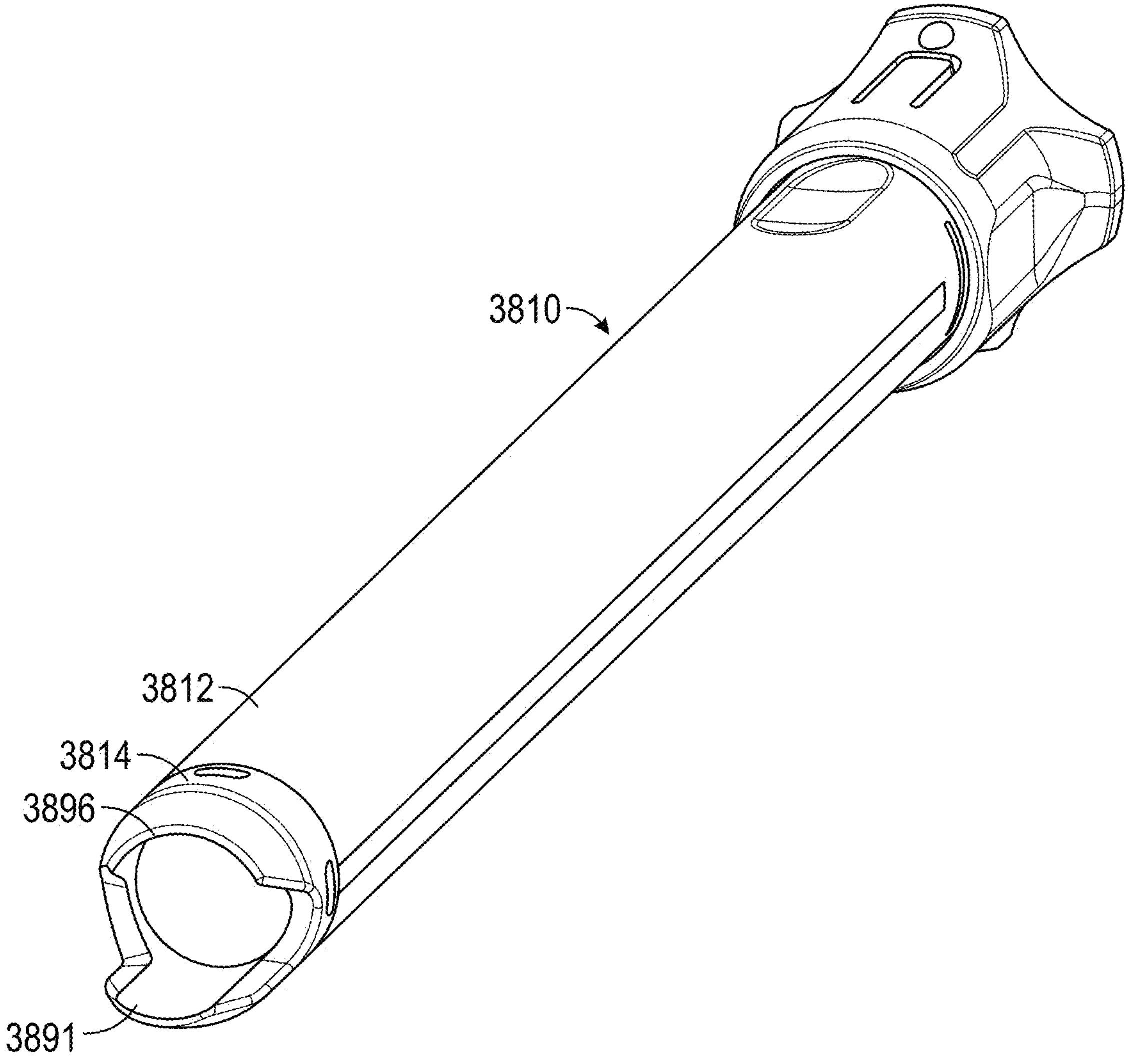
FIG. 38E shows a perspective view of the cannula of FIG. 38D.

FIG. 38E shows a perspective view of the cannula 3810 of FIG. 38D.

The distal end 3814 may be smooth or have teeth on it to prevent migration of the cannula 3810 (and any guide positioned therein) while drilling, or removing bone. The superior portion may be shorter than the inferior portion. The superior portion may not have to extend it as far as the inferior portion, as it does not have to protect neural elements. The inferior distal end of the outer portion 3896 may also be notched or grooved to accommodate the passing of drill bit or other bone removing instruments. This may allow an internal guide to be moved to numerous positions to accommodate a drill bit or bone removing instrument.

There may be a pad printed line that goes down the side of the cannula 3810 or guide to show the user the orientation of the lamina. The line may also be embossed or engraved or machined to indicate a visual line when the instrument is buried in the tissue so a user can see it from above.

Figure 38F:
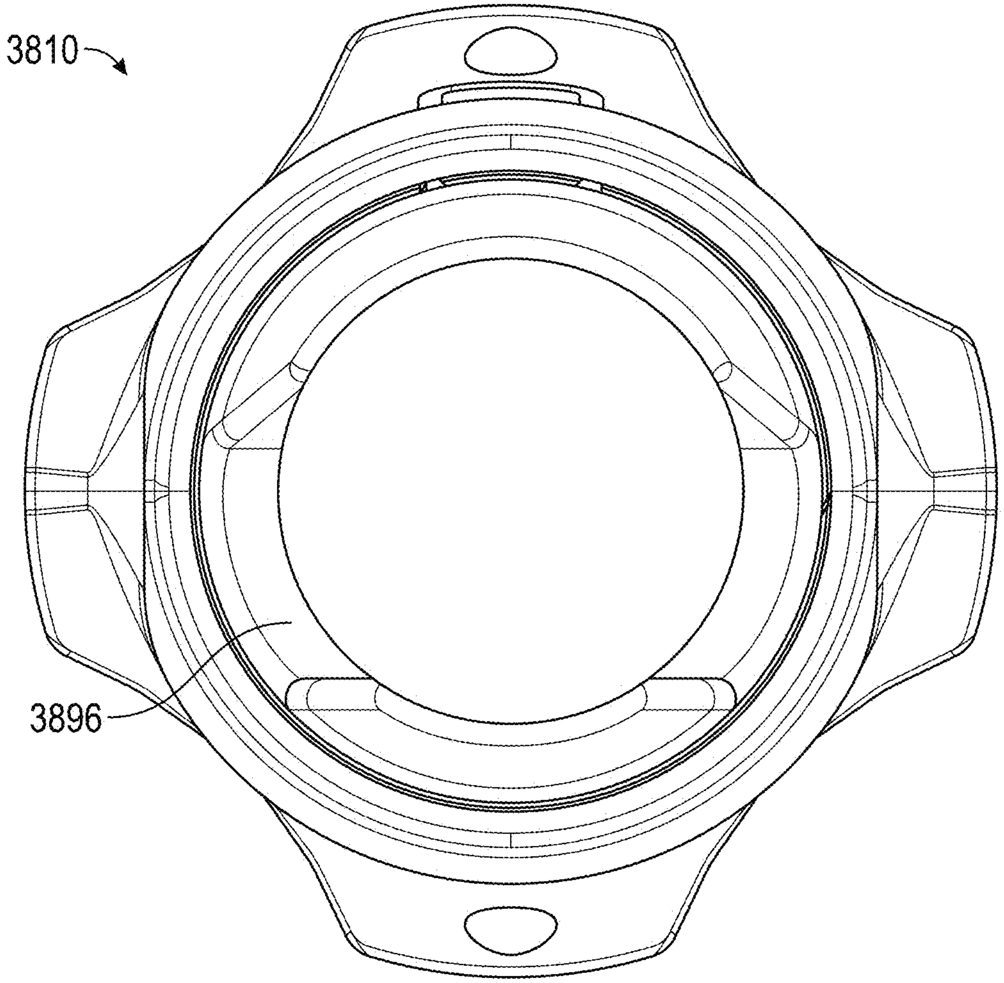
FIG. 38F shows a front view of the cannula of FIG. 38D.

FIG. 38F shows a front view of the cannula 3810 of FIG. 38D.

The cannula 3810 can be entirely circumferential, including the distal end of the instrument guide or outer portion 3896. In some examples, the cannula 3810 may not be fully circumferential and may have a flat portion at the bottom or top of the distal end that docks on the lamina. The distal end of the cannula 3810 may be sized and shaped to dock on a target area of the anatomy as it changes going from the thoracic spine to the lumbar spine.

Figure 38G:
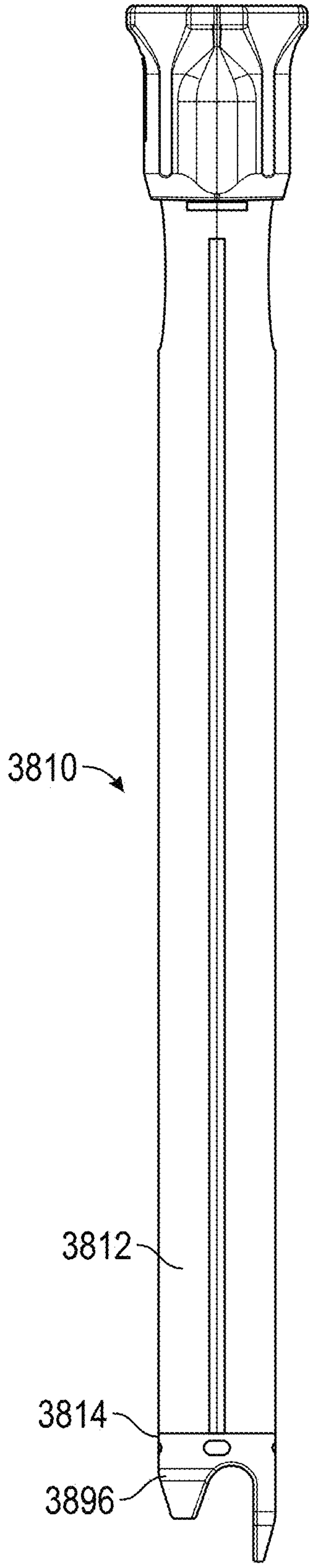
FIG. 38G shows a side view of the cannula of FIG. 38D.

FIG. 38G shows a side view of the cannula 3810.

The distal superior portion of the distal end 3814 can be shorter than the inferior distal portion. The distal superior portion can be configured to engage a posterior surface of the lamina and the inferior distal portion can be configured to engage an anterior surface of the lamina. The distal inferior portion can be curved with a blunt edge to protect the nerve structures while passing under the lamina, decreasing risk to the patient. Having the inferior portion pointed can allow the user to slide the distal end 3814 under the lamina (e.g., to the anterior surface of the lamina), minimizing the risk to the patient. The guards 3891 protruding from the distal end 3814 may also be flat to pass-through tissue more easily at different levels. The shape of the distal end 3814 can vary depending on the region of the spine because laminas vary at different levels of the spine.

Instruments described herein may come in a disposable or reusable kit. The disposable kit may be sterilized using EO gamma, or e-beam sterilization. Certain instruments may be autoclaved. There may be different kits for different levels of the spine because different anatomies require different shaped instruments. A fluoroscopy device or a light source that may be disposable can be in the kit to allow for direct visualization.

In certain conventional procedures laminotomies are performed along with debulking of the ligamentum flavin. Examples of the procedure described herein may not focus on the ligamentum flavin, but may focus on bone removal and removal of other soft tissues in the region. In comparison to previous laminotomies, the approaches described herein (e.g., inferior approaches) can minimize soft tissue disruption while decreasing the chances of cord or nerve root injuries.

In some embodiments, some or all of the instruments within a spinal decompression set or kit may be reusable instruments, such as titanium or stainless steel instruments, which may be auto claved and cleaned after use. In some examples, the instruments can be provided as a fully sterile disposable kit with instruments made of different types of polymers, metals, or other materials. The instruments can be engineered for case-of-use and decreased costs that may benefit in a surgery center or even hospitals. The fully sterile kit may also decrease the risk of infection by having the kit and instruments remain sterile and clean to minimize the risk of improper cleaning or sterilization.

Any of the devices or systems described herein can be used with navigation, robotics, and/or augmented reality to visualize placement of the devices or systems, including the scalpel 106, the guard 300, instrument shuttle 310, the guard plate 305, the hook 311, hook 2311, the guide 1104, the trephine 1110, trephine 2600, the drill burr 1111, the drill bit 1112, rongeurs, pituitarys, decompression system 2151, ligament probe 2300, skin stop 2588, instrument shuttle 2110, working channel 2200, light source 2220, and/or any other instruments which contribute to decompression and/or the placement of any of the aforementioned instruments. For example, any of the instruments may attach to one or more navigation markers (e.g., spheres or navigation registers) to allow for visualization or other tracking of the position of the instruments in space relative to the patient to allow for precise placement and/or prevent injury. In some embodiments, the instrument(s) may attach to the navigation markers via clips either on the instruments or on the markers. In some embodiments, the instrument(s) may attach to a navigation guide having one or more navigation markers attached thereto.

In some embodiments, any of the working channel 700, working channel 2200, guide 1104, or dilator tubes may be radiolucent. In some embodiments, a portion of any of the working channel 700, working channel 2200, guide 1104, or dilator tubes (e.g., a distal end portion) may be radiolucent (e.g., to provide a target for navigation). In other embodiments, any of the working channel 700, working channel 2200, guide 1104, or dilator tubes may be non-radiolucent e.g., to avoid obscuring other radiolucent materials in x-ray or fluoroscopy.

In some embodiments, one or more of the instruments described herein can be provided in a kit. A kit may include one or more of a scalpel guide 100, blade 201, a scalpel 106, a guide wire 200, a guard 300, a guard 1100, a working channel 700, a working channel 2200, a dilator, an instrument shuttle 310, an instrument shuttle 2110, a trephine 1000, a trephine 1110, a trephine 2600, a drill bur 1111, a drill bit 1112, a kerrison, a reamer, a pituitary, a rongeur, a light, a loupes, a microscope, a navigation marker, a hook 2311, a ligament probe 2300, a skin stop 2588, a light source 2220, and a navigation guide. In some embodiments, a kit may include multiple of any of the foregoing, such as, for example, multiple guards. For example, a kit may include a guard 300 and a guard 1100 for approaching different anatomies. In some embodiments, a kit may include multiple guards 300 or multiple guards 1100 having guard plates with different fixed angles. In some embodiments, a kit may include multiple upper clamp members 2162 and/or lower clamp member 2164 for different anatomies. In some embodiments, a kit may include multiple upper clamp members 2162 and/or lower clamp member 2164 with different fixed angles.

In certain embodiments, a decompression procedure can include one or more of the following steps. In some embodiments, an incision can be made, for example, using a scalpel such as scalpel 106. After the incision is made, one or more dilators may be advanced to a target area, such as a lamina. After dilation, a guard 300 can be advanced to the target area. After the guard 300 is advanced to the target area, a working channel 700 can be coupled to the guard 300 and advanced to the target area. The target area can be secured between a guard plate 305 of the guard 300 and a distal end 901 of the working channel 700. Then, one or more instruments can be advanced through the working channel to the target area and used to ream, drill, or otherwise cut away or remove bone to cause decompression.

In certain embodiments, a decompression procedure can include one or more of the following steps. In some embodiments, an incision can be made, for example, using a scalpel such as scalpel 106. After the incision is made, one or more dilators may be advanced to a target area, such as a lamina. After dilation, an instrument shuttle 310 can be advanced to the target area. The instrument shuttle 310 can engage the target area. After the instrument shuttle 310 engages the target area, a working channel 700 can be coupled to the instrument shuttle 310 and advanced to the target area. A guard 1100 can be advanced through or outside of the working channel 700. The target area can be secured between a guard plate 1103 of the guard 1100 and a distal end 901 of the working channel 700. Then, one or more instruments can be advanced through the working channel to the target area and used to ream, drill, or otherwise cut away or remove bone to cause decompression. Alternatively, after the target area is secured between the guard plate 1103 and the distal end 901 of the working channel 700, a guide 1104 can be inserted into the working channel 700. One or more instruments can be advanced down one or more channels of the guide 1104 to the target area and used to ream, drill, or otherwise cut away or remove bone to cause decompression.

The decompression systems and devices described herein can be used for an approach parallel to or perpendicular to a target anatomical area, such as a lamina. For example, FIG. 16 shows a perpendicular approach in which a longitudinal axis of the working channel 700 (and/or any instruments advanced therethrough) and/or guard body 304 can be perpendicular or generally perpendicular to a top surface of the lamina. FIGS. 17B, and 18C-18D show a parallel approach in which a longitudinal axis of the instrument shuttle 310, working channel 700 (and/or any instruments advanced therethrough), guide 1104 (and/or any instruments advanced therethrough), and/or guard handle 1102 can be parallel or generally parallel to a top surface of the lamina.

While decompression at a lamina is described herein in certain examples, one of skill in the art would understand that the devices, systems, and methods described herein can be used for other anatomical locations and/or other procedures. For example, the guards described herein may be used to provide a safety stop and/or otherwise protect anatomical areas adjacent to a treatment area at which instruments are passed through or used for cutting, removing, and/or otherwise manipulating tissue.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible.

What is claimed is:

1. A method for performing decompression surgery, the method comprising:

engaging a cannula with a lamina of a patient, the cannula comprising a lumen;

positioning a guide within the lumen of the cannula in a first position, the guide comprising a guide lumen offset from a central longitudinal axis of the guide;

advancing an instrument through the guide lumen to the lamina and removing a first portion of the lamina using the instrument;

moving the guide to a second position within the cannula so that the guide lumen aligns with a second portion of the lamina; and advancing the instrument through the guide lumen to the lamina and removing the second portion of the lamina using the instrument.

2. The method of claim 1, further comprising:

prior to engaging the cannula with the lamina of the patient, engaging a laminar locator with a lamina of the patient;

advancing a dilator over the laminar locator; and advancing the cannula over the dilator.

3. The method of claim 2, wherein the laminar locator comprises one or more angled edges, wherein the method comprises translating the laminar locator back and forth to shave bone overgrowth by the angled edges.

4. The method of claim 1, further comprising coupling a stabilizer to the cannula, the stabilizer comprising a plurality of legs configured to contact a skin surface of the patient or a drape positioned over the skin surface of the patient.

5. The method of claim 2, wherein the laminar locator comprises one or more angled surfaces shaped to shave bone overgrowth while the laminar locator is advanced to the lamina.

6. The method of claim 4, further comprising rotating the plurality of legs about a plurality of axes.

7. The method of claim 4, wherein each of the plurality of legs of the stabilizer comprises one or more non-slip surface features configured to engage the patient.

8. The method of claim 4, further comprising rotating the plurality of legs of the stabilizer about a central body of the stabilizer.

9. The method of claim 4, further comprising rotating the plurality of legs about a longitudinal axis of the cannula and one or more axes perpendicular with the longitudinal axis of the cannula.

10. The method of claim 4, further comprising actuating a knob of the stabilizer to transition the stabilizer between an unlocked state in which the plurality of legs are rotatable and locked state in which the plurality of legs are locked in position relative to a central body of the stabilizer.

11. The method of claim 4, further comprising securing the stabilizer at multiple axial positions along the cannula to adjust a height of the plurality of legs relative to a body of the patient.

12. The method of claim 1, further comprising positioning at least one protrusion of the guide within at least one first slot of the cannula.

13. The method of claim 12, further comprising positioning the at least one protrusion of the guide within at least one second slot of the cannula to change a rotational position of the guide with respect to the cannula.

14. The method of claim 1, wherein the guide is rotatable between four rotatable positions within the cannula.

15. The method of claim 1, further comprising coupling a light source with a proximal end of the cannula.

16. The method of claim 1, further comprising coupling a cap to a body of the cannula.

17. The method of claim 1, wherein the cannula comprises a superior guard portion configured to contact a posterior surface of the lamina, an inferior guard configured to contact an anterior surface of the lamina, and a recess between the superior guard portion and inferior guard portion configured to receive an inferior edge of the lamina therein.

18. The method of claim 17, wherein the inferior guard portion has a greater length than the superior guard portion.

* * * * *